United States Patent
Guzi et al.

(10) Patent No.: US 7,576,085 B2
(45) Date of Patent: *Aug. 18, 2009

(54) IMIDAZOPYRAZINES AS CYCLIN DEPENDENT KINASE INHIBITORS

(75) Inventors: Timothy J. Guzi, Chatham, NJ (US); Kamil Paruch, Garwood, NJ (US); Michael P. Dwyer, Scotch Plains, NJ (US); Lianyun Zhao, Burlington, MA (US); Patrick J. Curran, Winthrop, MA (US); David B. Belanger, Cambridge, MA (US); Blake Hamann, Cambridge, MA (US); Panduranga A. Reddy, Walpole, MA (US); M. Arshad Siddiqui, Newton, MA (US)

(73) Assignee: Schering Corporation, Kenilworth, NJ (US)

( * ) Notice: Subject to any disclaimer, the term of this patent is extended or adjusted under 35 U.S.C. 154(b) by 475 days.

This patent is subject to a terminal disclaimer.

(21) Appl. No.: 11/272,392

(22) Filed: Nov. 10, 2005

(65) Prior Publication Data

US 2006/0106023 A1    May 18, 2006

Related U.S. Application Data

(60) Continuation-in-part of application No. 11/047,524, filed on Jan. 31, 2005, which is a division of application No. 10/665,005, filed on Sep. 19, 2003, now Pat. No. 6,919,341.

(60) Provisional application No. 60/412,997, filed on Sep. 23, 2002.

(51) Int. Cl.
| | |
|---|---|
| *A01N 43/58* | (2006.01) |
| *A01N 43/60* | (2006.01) |
| *A61K 31/50* | (2006.01) |
| *A61K 31/495* | (2006.01) |
| *C07D 403/00* | (2006.01) |
| *C07D 471/00* | (2006.01) |
| *C07D 487/00* | (2006.01) |
| *C07D 491/00* | (2006.01) |
| *C07D 495/00* | (2006.01) |
| *C07D 497/00* | (2006.01) |

(52) U.S. Cl. ................. 514/249; 544/295; 544/350
(58) Field of Classification Search ............... 514/249
See application file for complete search history.

(56) References Cited

U.S. PATENT DOCUMENTS

| 6,919,341 B2 * | 7/2005 | Paruch et al. ............... 514/249 |
| 2007/0117804 A1 * | 5/2007 | Zhao et al. ............... 514/249 |

OTHER PUBLICATIONS

Vippagunta et. al. Advanced Drug Delivery Reviews 48 (2001) 3-26.*
Dorwald F. A. Side Reactions in Organic Synthesis, 2005, Wiley: VCH, Weinheim p. IX of Preface.*

* cited by examiner

*Primary Examiner*—James O Wilson
*Assistant Examiner*—Jeffrey H Murray
(74) *Attorney, Agent, or Firm*—Palaiyur S. Kalyanaraman

(57) ABSTRACT

In its many embodiments, the present invention provides a novel class of imidazo[1,2-a]pyrazine compounds as inhibitors of cyclin dependent kinases, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with the CDKs using such compounds or pharmaceutical compositions. An illustrative compound of the invention is shown below:

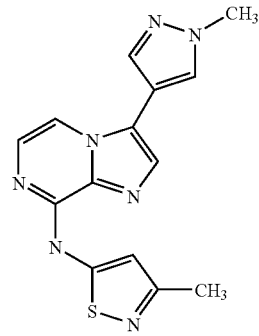

15 Claims, No Drawings

IMIDAZOPYRAZINES AS CYCLIN DEPENDENT KINASE INHIBITORS

REFERENCE TO PRIORITY APPLICATIONS

This application is a continuation-in-part of U.S. patent application Ser. No. 11/047,524 filed Jan. 31, 2005, which is a divisional of patent application Ser. No. 10/665,005 filed Sep. 19, 2003, which claims priority to provisional application 60/412,997, filed Sep. 23, 2002.

FIELD OF THE INVENTION

The present invention relates to imidazo[1,2-a]pyrazine compounds useful as protein kinase inhibitors (such as for example, the inhibitors of the cyclin-dependent kinases, mitogen-activated protein kinase (MAPK/ERK), glycogen synthase kinase 3(GSK3beta) and the like), pharmaceutical compositions containing the compounds, and methods of treatment using the compounds and compositions to treat diseases such as, for example, cancer, inflammation, arthritis, viral diseases, neurodegenerative diseases such as Alzheimer's disease, cardiovascular diseases, and fungal diseases.

BACKGROUND OF THE INVENTION

Protein kinase inhibitors include kinases such as, for example, the inhibitors of the cyclin-dependent kinases (CDKs), mitogen activated protein kinase (MAPK/ERK), glycogen synthase kinase 3 (GSK3beta), and the like. The cyclin-dependent kinases are serine/threonine protein kinases, which are the driving force behind the cell cycle and cell proliferation. Individual CDK's, such as, CDK1, CDK2, CDK3, CDK4, CDK5, CDK6 and CDK7, CDK8 and the like, perform distinct roles in cell cycle progression and can be classified as either G1, S, or G2M phase enzymes. Uncontrolled proliferation is a hallmark of cancer cells, and misregulation of CDK function occurs with high frequency in many important solid tumors. CDK2 and CDK4 are of particular interest because their activities are frequently misregulated in a wide variety of human cancers. CDK2 activity is required for progression through G1 to the S phase of the cell cycle, and CDK2 is one of the key components of the G1 checkpoint. Checkpoints serve to maintain the proper sequence of cell cycle events and allow the cell to respond to insults or to proliferative signals, while the loss of proper checkpoint control in cancer cells contributes to tumorgenesis. The CDK2 pathway influences tumorgenesis at the level of tumor suppressor function (e.g. p52, RB, and p27) and oncogene activation (cyclin E). Many reports have demonstrated that both the coactivator, cyclin E, and the inhibitor, p27, of CDK2 are either over—or underexpressed, respectively, in breast, colon, nonsmall cell lung, gastric, prostate, bladder, non-Hodgkin's lymphoma, ovarian, and other cancers. Their altered expression has been shown to correlate with increased CDK2 activity levels and poor overall survival. This observation makes CDK2 and its regulatory pathways compelling targets for the development years, a number of adenosine 5'-triphosphate (ATP) competitive small organic molecules as well as peptides have been reported in the literature as CDK inhibitors for the potential treatment of cancers. U.S. Pat. No. 6,413,974, col. 1, line 23-col. 15, line 10 offers a good description of the various CDKs and their relationship to various types of cancer.

CDK inhibitors are known. For example, flavopiridol (Formula I) is a nonselective CDK inhibitor that is currently undergoing human clinical trials, A. M. Sanderowicz et al, *J. Clin. Oncol.* (1998) 16, 2986-2999.

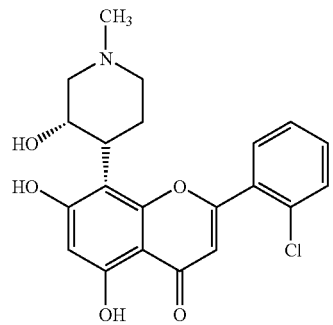

Formula I

Other known inhibitors of the CDKs include, for example, olomoucine (J. Vesely et al, *Eur. J. Biochem.*, (1994) 224, 771-786) and roscovitine (I. Meijer et al, *Eur. J. Biochem.*, (1997) 243, 527-536). U.S. Pat. No. 6,107,305 describes certain pyrazolo[3,4-b] pyridine compounds as CDK inhibitors. An illustrative compound from the '305 patent has the Formula II:

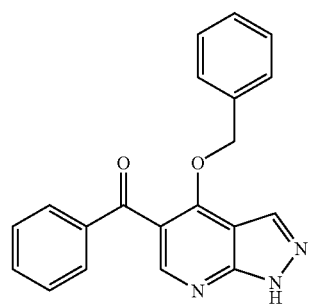

Formula II

K. S. Kim et al, *J. Med. Chem.* 45 (2002) 3905-3927 and WO 02/10162 disclose certain aminothiazole compounds as CDK inhibitors.

Imidazopyrazines are known. For example, U.S. Pat. No. 6,919,341 (the disclosure of which is incorporated herein by reference) and US2005/0009832 disclose various imidazopyrazines. Also being mentioned are the following: WO2005/047290; US2005/095616; WO2005/039393; WO2005/019220; WO2004/072081; WO2005/014599; WO2005/009354; WO2005/005429; WO2005/085252; US2005/009832; US2004/220189; WO2004/074289; WO2004/026877; WO2004/026310; WO2004/022562; WO2003/089434; WO2003/084959; WO2003/051346; US2003/022898; WO2002/060492; WO2002/060386; WO2002/028860; JP (1986)61-057587; J. Burke et al., *J. Biological Chem.*, Vol. 278(3), 1450-1456 (2003); and F. Bondavalli et al, *J. Med. Chem.*, Vol. 45 (22), 4875-4887 (2002).

There is a need for new compounds, formulations, treatments and therapies to treat diseases and disorders associated with CDKs. It is, therefore, an object of this invention to provide compounds useful in the treatment or prevention or amelioration of such diseases and disorders.

SUMMARY OF THE INVENTION

In its many embodiments, the present invention provides a novel class of imidazo[1,2-a]pyrazine compounds as inhibitors of cyclin dependent kinases, methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the CDKs using such compounds or pharmaceutical compositions.

In one aspect, the present application discloses a compound, or pharmaceutically acceptable salts, solvates or esters or prodrugs of said compound, said compound having the general structure shown in Formula III:

Formula III

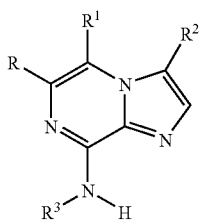

wherein:

R is selected from the group consisting of H, halogen, aryl, heteroaryl, cycloalkyl, arylalkyl, heterocyclyl, heterocyclylalkyl, alkenyl, alkynyl, —C(O)R$^7$,

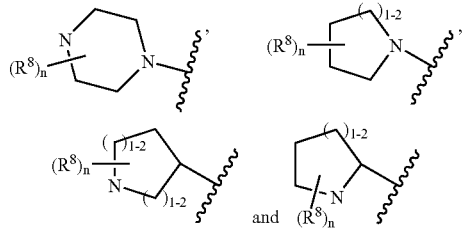

wherein each of said aryl, heteroaryl, cycloalkyl, arylalkyl, alkenyl, heterocyclyl and the heterocyclyl moieties whose structures are shown immediately above for R can be unsubstituted or optionally independently substituted with one or more moieties which can be the same or different, each moiety being independently selected from the group consisting of halogen, alkyl, cycloalkyl, CF$_3$, CN, —OCF$_3$, —OR$^6$, —C(O)R$^7$, —NR$^5$R$^6$, —C(O$_2$)R$^6$, —C(O)NR$^5$R$^6$, —(CHR$^5$)$_n$OR$^6$, —SR$^6$, —S(O$_2$)R$^7$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$;

R$^1$ is H, halogen, or alkyl;

R$^2$ is selected from the group consisting of R$^9$, alkyl, aryl, arylalkyl, heteroaryl, heteroarylalkyl, heterocyclyl, alkenyl, alkynyl, cycloalkyl, cycloalkylalkyl, heterocyclylalkyl, —CF$_3$, —C(O)R$^7$, alkyl substituted with 1-6 R$^9$ groups which groups can be the same or different with each R$^9$ being independently selected,

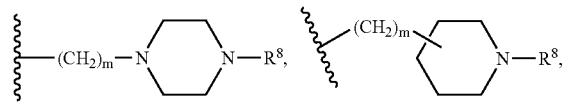

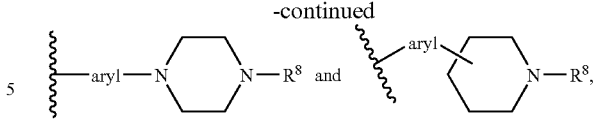

wherein each of said aryl, heteroaryl, cycloalkyl, arylalkyl and heterocyclyl can be unsubstituted or optionally independently substituted with one or more moieties which can be the same or different, each moiety being independently selected from the group consisting of halogen, alkyl, cycloalkyl, CF$_3$, CN, —OCF$_3$, —OR$^6$, —C(O)R$^7$, —NR$^5$R$^6$, —C(O$_2$)R$^6$, —C(O)NR$^5$R$^6$, —SR$^6$, —S(O$_2$)R$^7$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$;

R$^3$ is selected from the group consisting of H, aryl, heteroaryl, heterocyclyl, —(CH R$^5$)$_n$-aryl, —(CH R$^5$)$_n$-heteroaryl, —(CHR$^5$)$_n$-cycloalkyl, —(CHR$^5$)$_n$-heterocycloalkyl, —(CHR$^5$)$_n$—CH(aryl)$_2$,

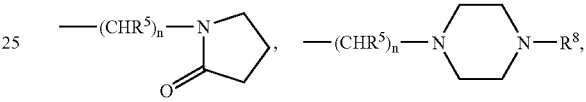

—(CHR$^5$)$_n$—OR$^6$, —S(O$_2$)R$^6$, —C(O)R$^6$, —S(O$_2$)NR$^5$R$^6$, —C(O)OR$^6$, —C(O)NR$^5$R$^6$, cycloalkyl, —CH(aryl)$_2$, —CH(heteroaryl)$_2$, —(CH$_2$)$_m$—NR$^8$, and

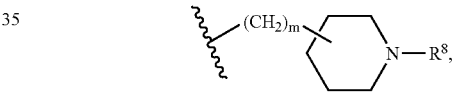

wherein each of said aryl, heteroaryl and heterocyclyl can be substituted or optionally substituted with one or more moieties which can be the same or different, each moiety being independently selected from the group consisting of halogen, alkyl, aryl, cycloalkyl, CF$_3$, CN, —OCF$_3$, —OR$^5$, —NR$^5$R$^6$, —C(O$_2$)R$^5$, —C(O)N R$^5$R$^6$, —SR$^6$, —S(O$_2$)R$^6$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$;

R$^5$ is H or alkyl;

R$^6$ is selected from the group consisting of H, alkyl, aryl, heteroaryl, arylalkyl and heteroarylalkyl, wherein each of said alkyl, heteroarylalkyl, aryl, heteroaryl and arylalkyl can be unsubstituted or optionally substituted with one or more moieties which can be the same or different, each moiety being independently selected from the group consisting of halogen, alkyl, aryl, cycloalkyl, CF$_3$, OCF$_3$, CN, —OR$^5$, —NR$^5$R$^6$, —CH$_2$OR$^5$, —C(O$_2$)R$^5$, —C(O)NR$^5$R$^6$, —SR$^6$, —S(O$_2$)R$^7$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$;

R$^7$ is selected from the group consisting of alkyl, aryl, heteroaryl, arylalkyl and heteroarylalkyl, wherein each of said alkyl, heteroarylalkyl, aryl, heteroaryl and arylalkyl can be unsubstituted or optionally substituted with one or more moieties which can be the same or different, each moiety being independently selected from the group consisting of halogen, alkyl, aryl, cycloalkyl, CF$_3$, OCF$_3$, CN, —OR$^5$, —NR$^5$R , —CH$_2$OR$^5$, —C(O$_2$)R$^5$, —C(O)NR$^5$R$^6$, —SR$^6$, —S(O$_2$)R$^7$, —S(O$_2$)NR$^5$R$^6$, —N(R$^5$)S(O$_2$)R$^7$, —N(R$^5$)C(O)R$^7$ and —N(R$^5$)C(O)NR$^5$R$^6$;

R$^8$ is selected from the group consisting of R$^6$, —C(O)NR$^5$R$^6$, —S(O$_2$)NR$^5$R$^6$, —C(O)R$^7$, —C(O$_2$)R$^6$, —S(O$_2$)R$^7$ and —(CH$_2$)-aryl;

R$^9$ is selected from the group consisting of halogen, CN, NR$^5$R , —C(O$_2$)R$^6$, —C(O)N R$^5$R$^6$, —OR$^6$, —C(O)R$^7$, —SR$^6$, —S(O$_2$)R$^7$, —S(O$_2$)NR$^5$R$^6$, —N(R$^5$)S(O$_2$)R$^7$, —N(R$^5$)C(O)R$^7$ and —N(R$^5$)C(o)NR$^5$R$^6$;

m is 0 to 4;
n is 1-4; and
p is 0-3.

The compounds of Formula III can be useful as protein kinase inhibitors and can be useful in the treatment and prevention of proliferative diseases, for example, cancer, inflammation and arthritis. They may also be useful in the treatment of neurodegenerative diseases such Alzheimer's disease, cardiovascular diseases, viral diseases and fungal diseases.

DETAILED DESCRIPTION

In one embodiment, the present invention discloses imidazo[1,2-a]pyrazine compounds which are represented by structural Formula III, or a pharmaceutically acceptable salt or solvate thereof, wherein the various moieties are as described above.

In another embodiment, R is selected from the group consisting of H, halogen, aryl, heteroaryl, alkenyl and —C(O)R$^7$, wherein each of said aryl and heteroaryl can be unsubstituted or optionally independently substituted with one or more moieties which can be the same or different, each moiety being independently selected from the group consisting of halogen, alkyl, CF$_3$, CN, —OCF$_3$, and —OR$^6$.

In another embodiment, R$^1$ is H or lower alkyl.

In another embodiment, R$^2$ is selected from the group consisting of halogen, alkyl, aryl, heteroaryl, alkenyl and —C(O)R$^7$, wherein each of said alkyl, aryl and heteroaryl can be unsubstituted or optionally independently substituted with one or more moieties which can be the same or different, each moiety being independently selected from the group consisting of halogen, alkyl, CF$_3$, CN, —OCF$_3$, and —OR$^6$.

In another embodiment, R$^3$ is selected from the group consisting of H, aryl, heteroaryl, —(CHR$^5$)$_n$-aryl, —(CHR$^5$)$_n$-heteroaryl, —(CHR$^5$)$_n$—OR$^6$, —C(O)R$^6$, cycloalkyl, —CH(aryl)$_2$,

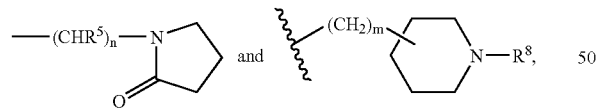

and wherein each of said aryl and heteroaryl can be substituted or optionally substituted with one or more moieties which can be the same or different, each moiety being independently selected from the group consisting of halogen, alkyl, aryl, CF$_3$, CN, —C(O$_2$)R$^5$ and —S(O$_2$)R$^6$.

In another embodiment, R$^5$ is H or lower alkyl.
In another embodiment, m is 0 to 2.
In another embodiment, n is 1 to 3.
In an additional embodiment, R is selected from the group consisting of H, phenyl and heteroaryl.
In an additional embodiment, R$^1$ is H, Br or methyl.
In an additional embodiment, R$^2$ is F, Cl, Br, I, aryl, alkenyl, heteroaryl or CF$_3$.

In an additional embodiment, R$^3$ is phenyl, (pyrid-2-yl)methyl, (pyrid-3-yl)methyl, (pyrid4-yl)methyl, 2-[(pyrid-3-yl)]ethyl, 2-[(pyrid4-yl)]ethyl, 2-ylpropanol, 3-ylpropyl-10pyrrolidin-2-one, or —C(O)CH$_3$, wherein said pyridyl can be unsubstituted or optionally substituted with one or more moieties which can be the same or different, each moiety being independently selected from the group consisting of F, Cl, Br, CF$_3$, lower alkyl, methoxy and CN.

In an additional embodiment, R$^5$ is H.
In an additional embodiment, m is 0.
In an additional embodiment, n is 1 or 2.

An inventive group of compounds is shown in Table 1.

TABLE 1

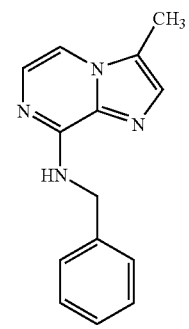

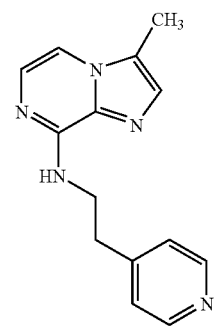

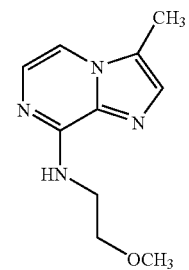

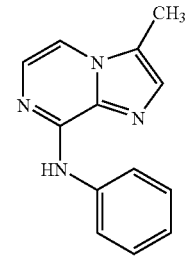

TABLE 1-continued
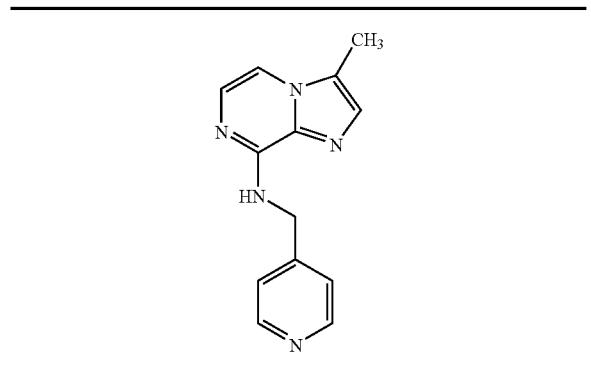
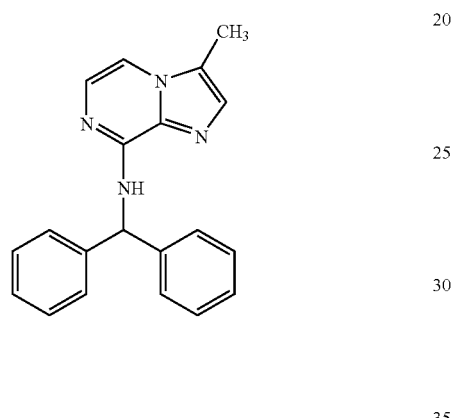
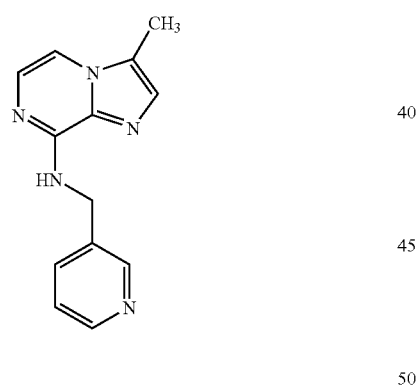
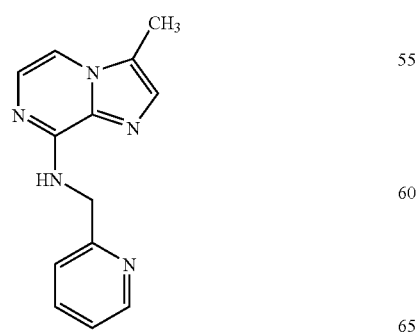
TABLE 1-continued
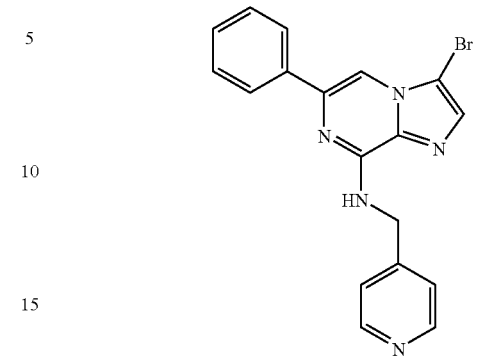
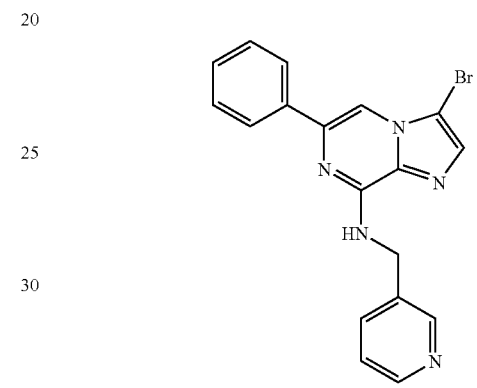
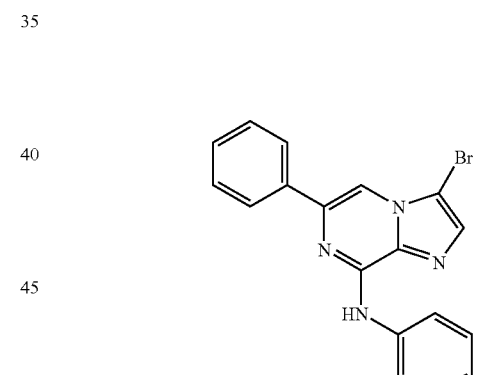
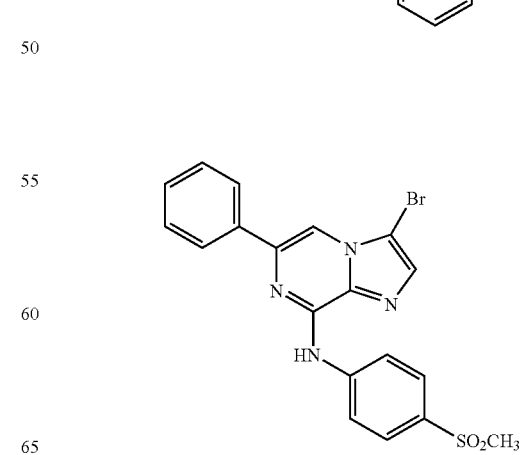

TABLE 1-continued
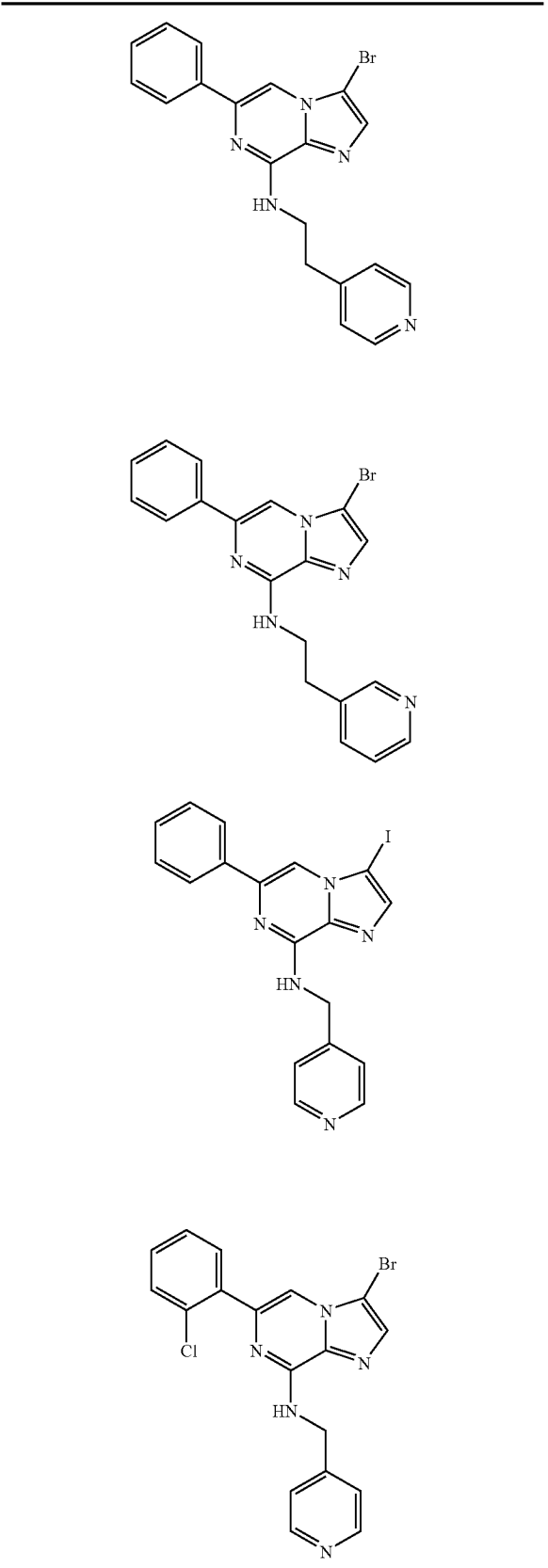
TABLE 1-continued
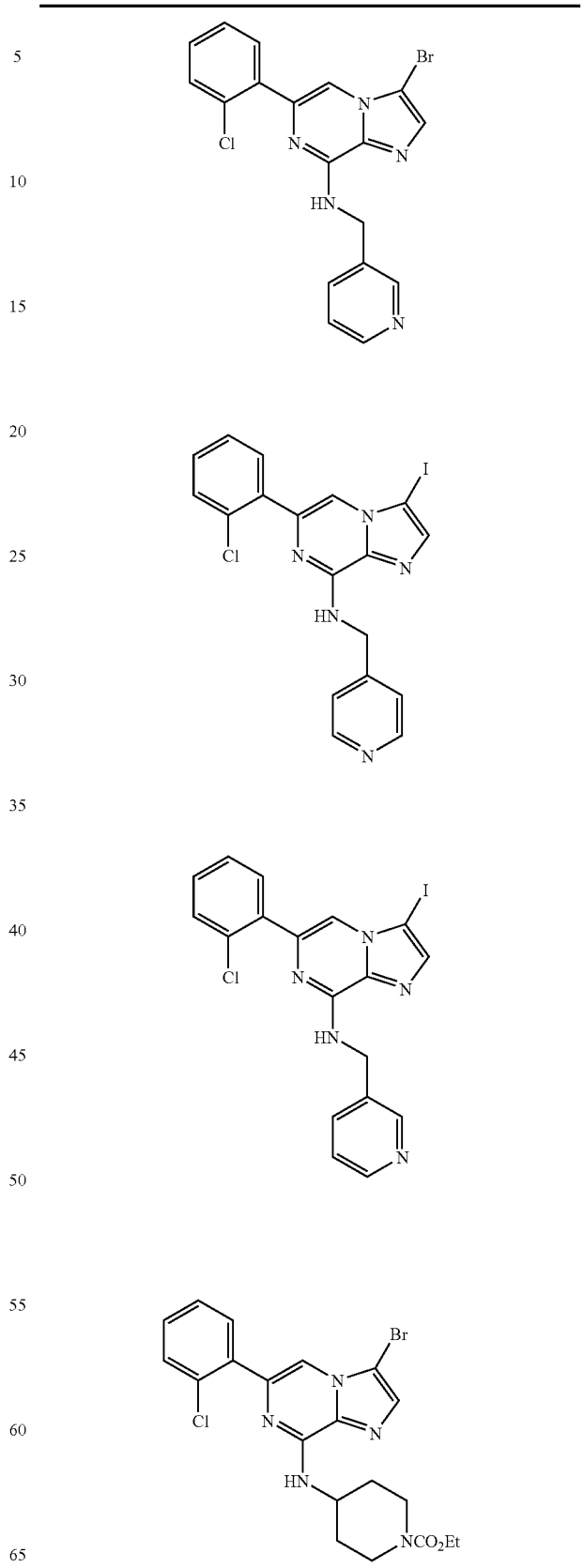

TABLE 1-continued
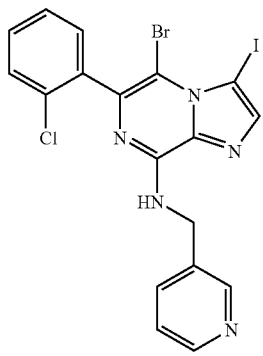
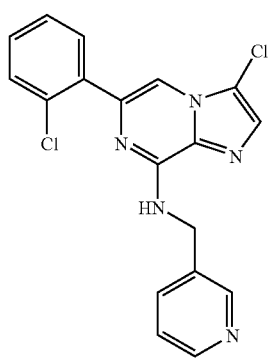
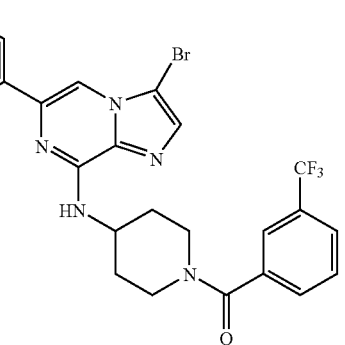
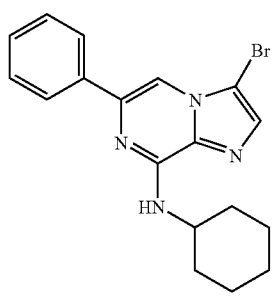
TABLE 1-continued
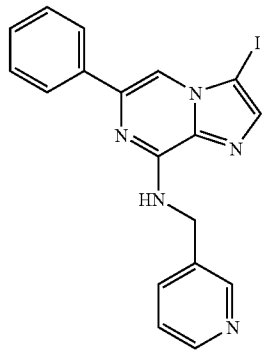
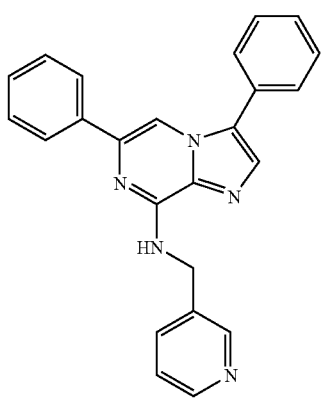
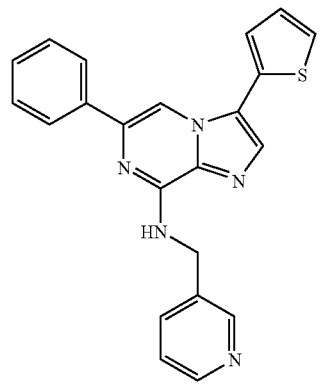
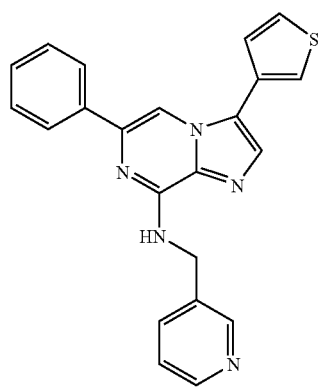

TABLE 1-continued
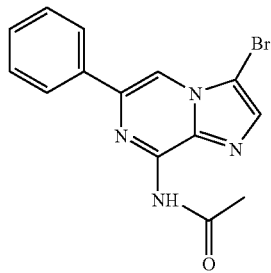
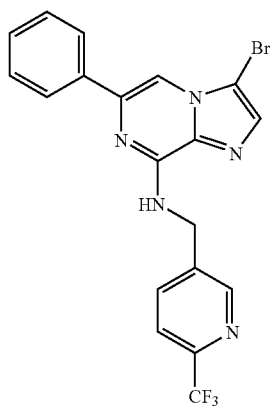
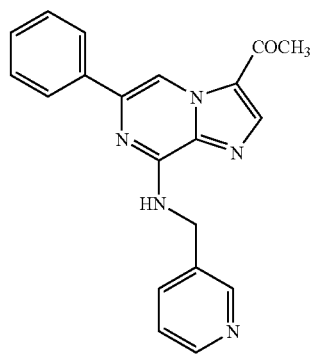
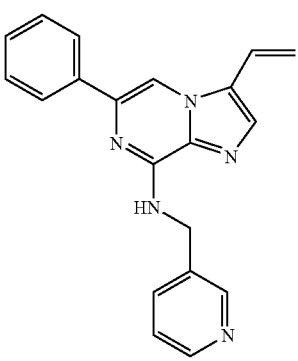
TABLE 1-continued
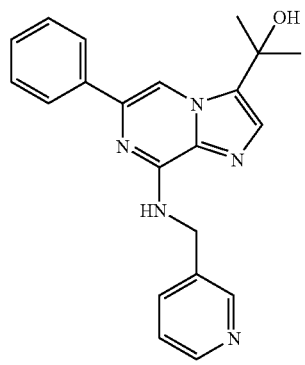
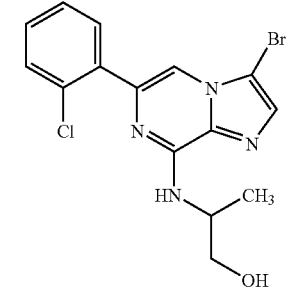
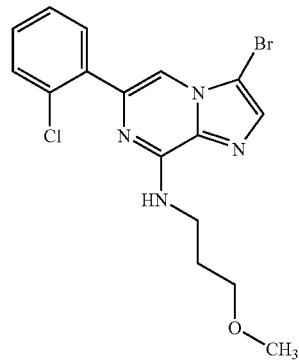
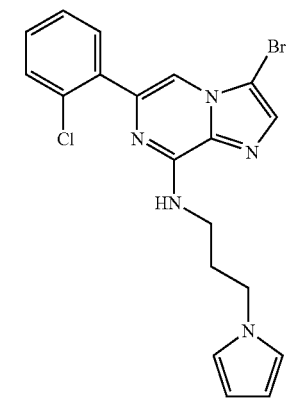

TABLE 1-continued
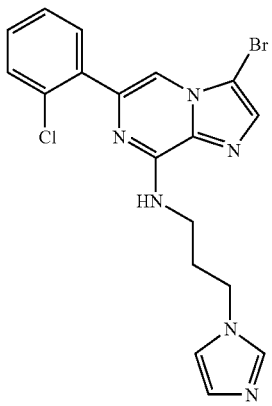
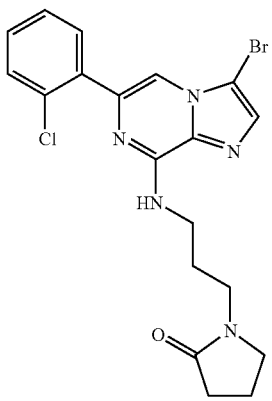
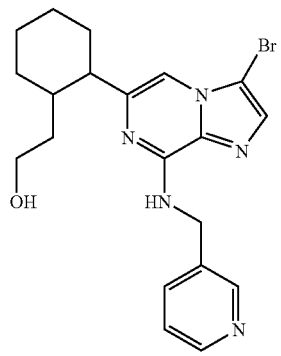
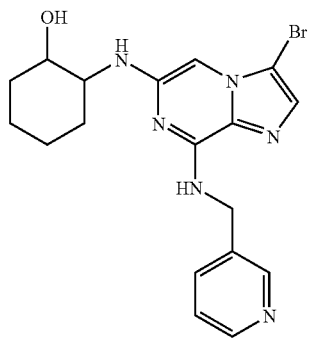
TABLE 1-continued
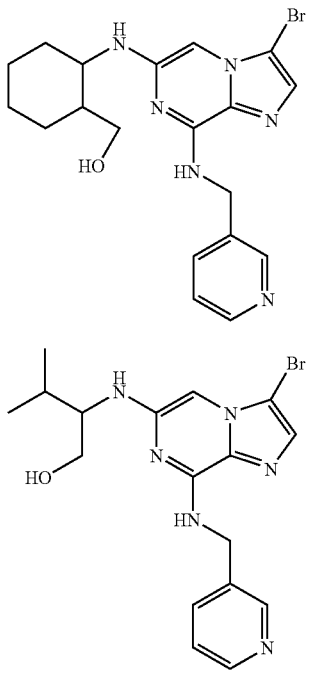
or a pharmaceutically acceptable salt, solvate or ester thereof.
Another embodiment discloses compounds of the formula in Table 1A:
TABLE 1A
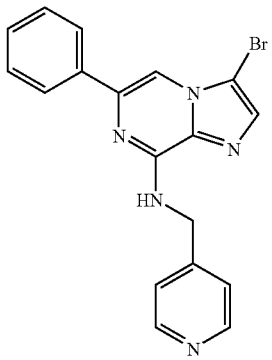
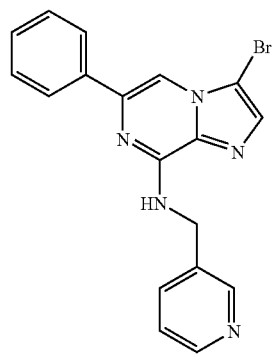

TABLE 1A-continued
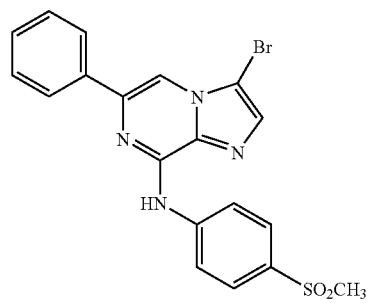
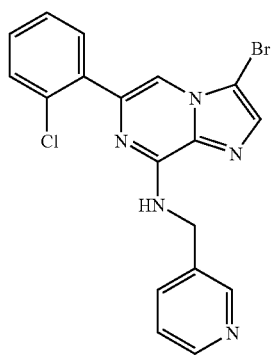
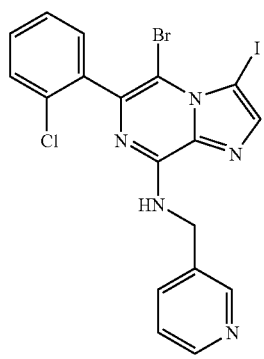
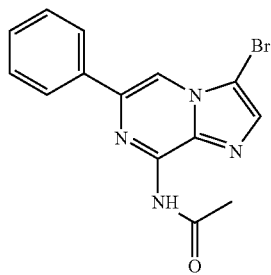
TABLE 1A-continued
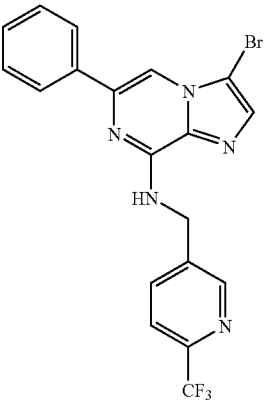
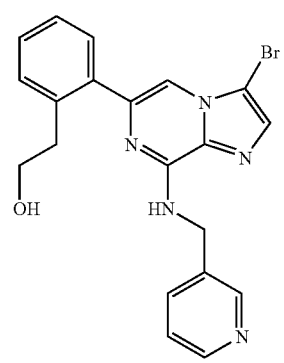
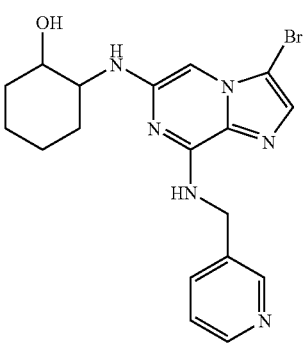
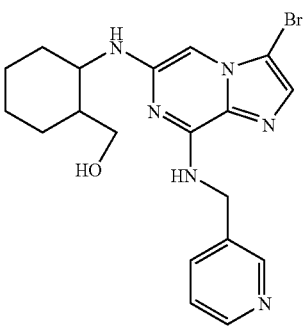
and

TABLE 1A-continued
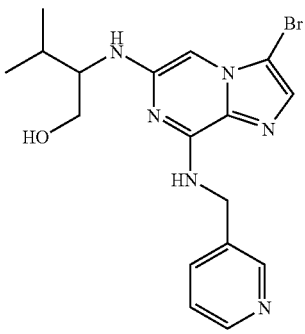
or a pharmaceutically acceptable salt, solvate or ester thereof.
Yet another group of inventive compounds are listed below in Table 1B:
TABLE 1B
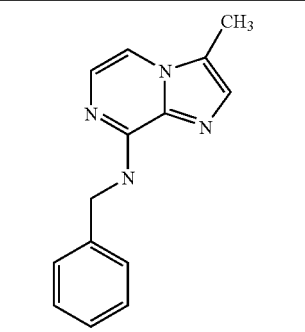
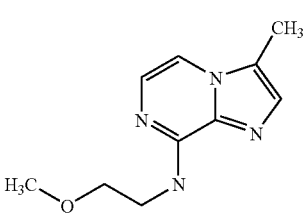
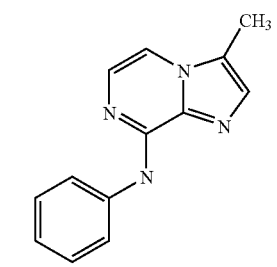
TABLE 1B-continued
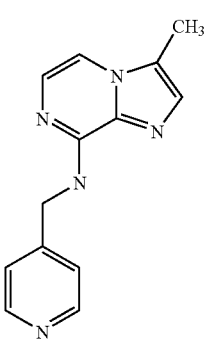
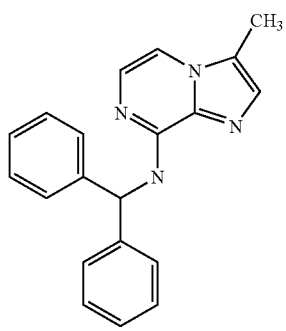
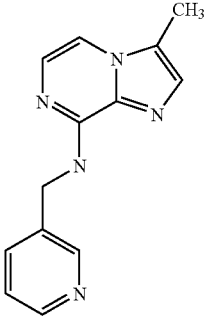
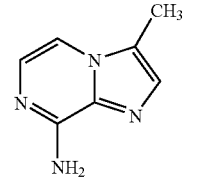
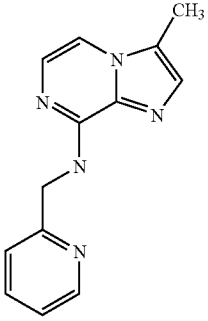

TABLE 1B-continued
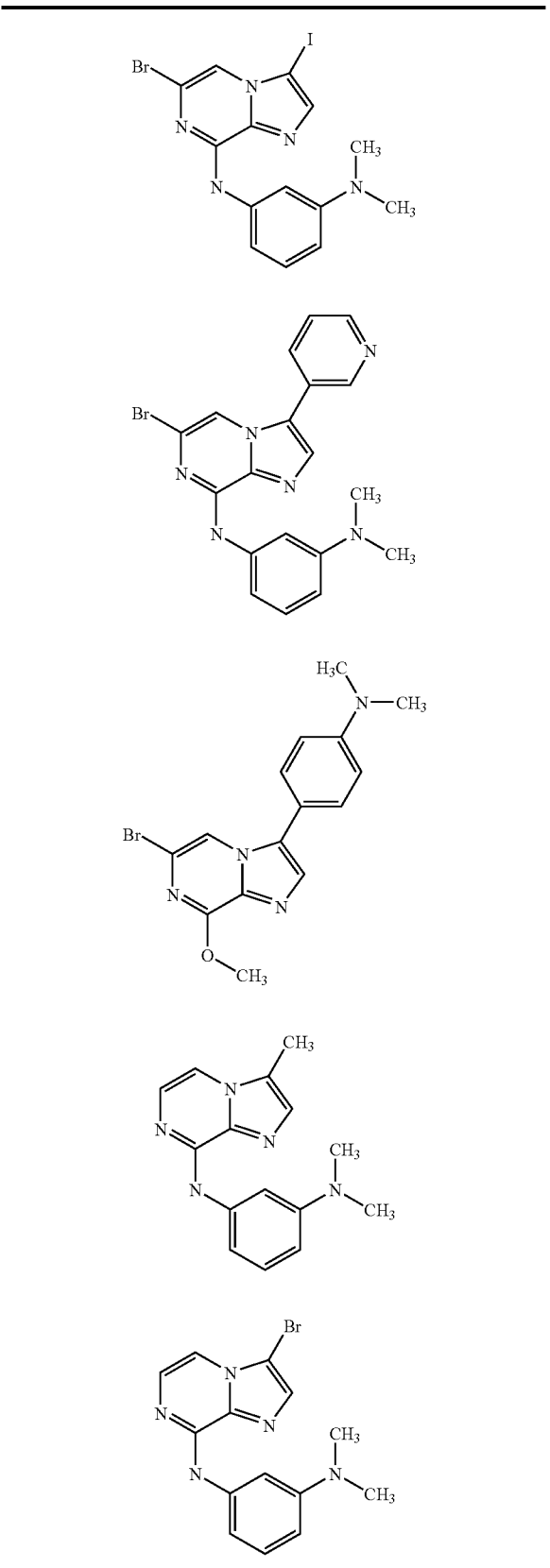
TABLE 1B-continued
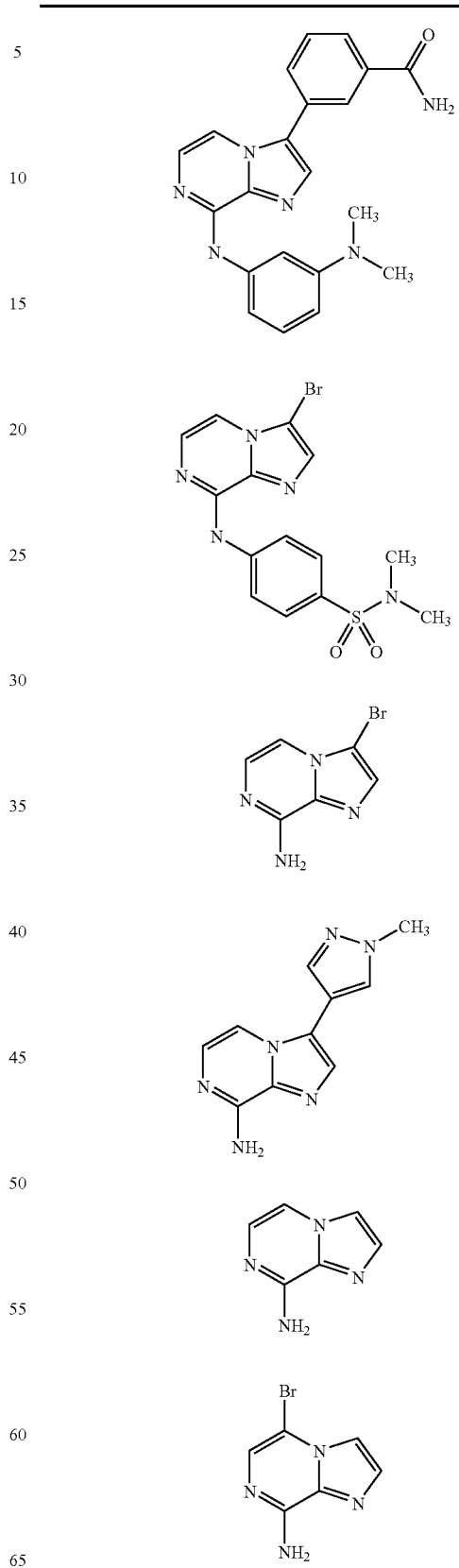

TABLE 1B-continued
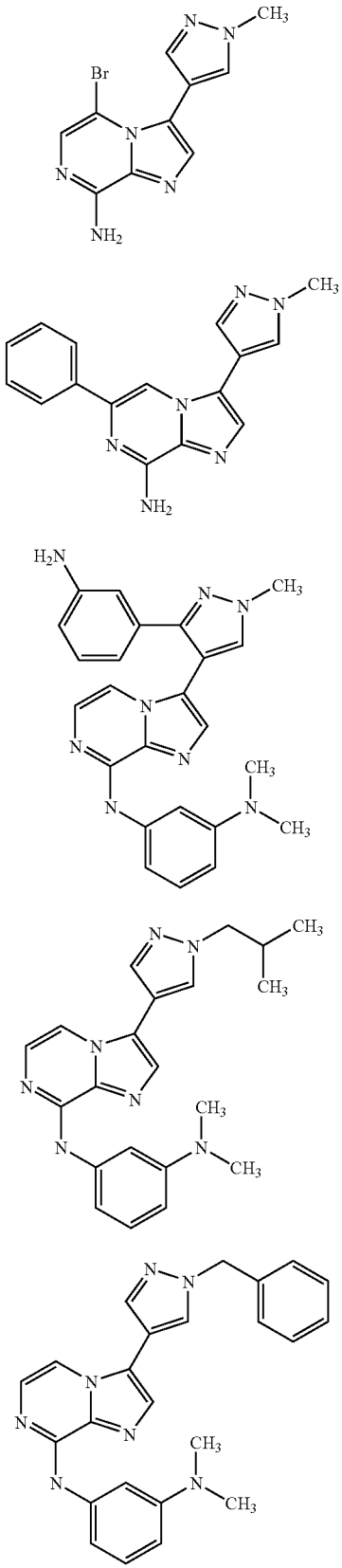
TABLE 1B-continued
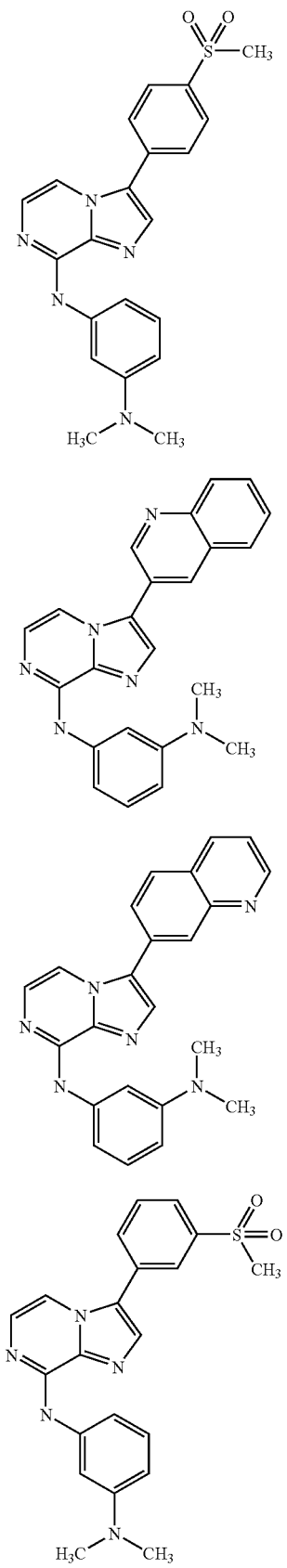

TABLE 1B-continued
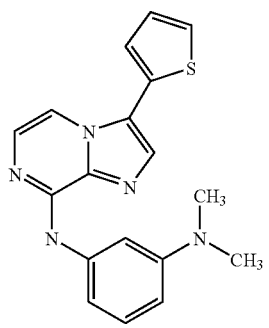
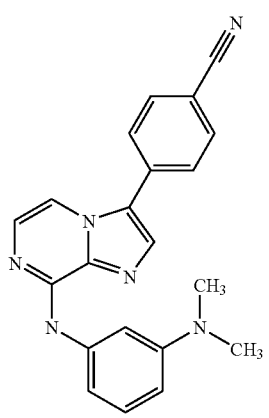
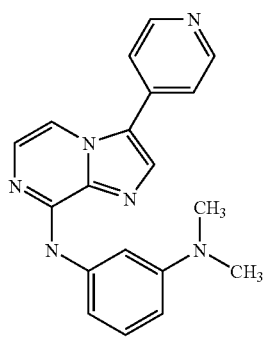
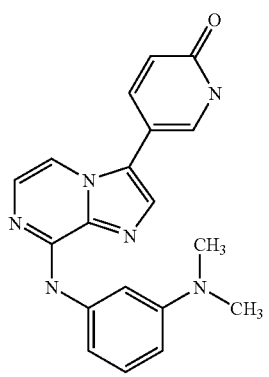
TABLE 1B-continued
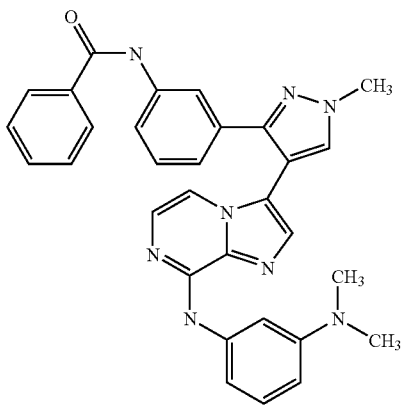
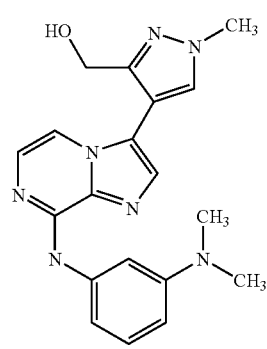
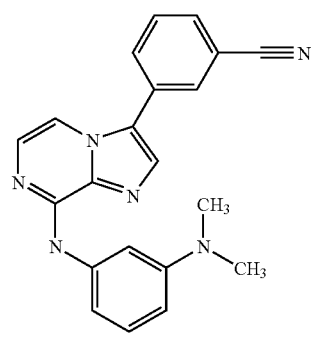
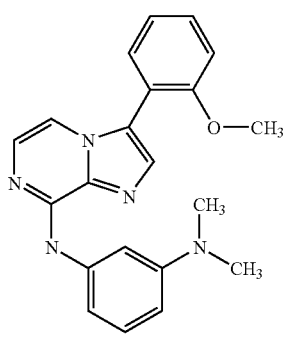

TABLE 1B-continued
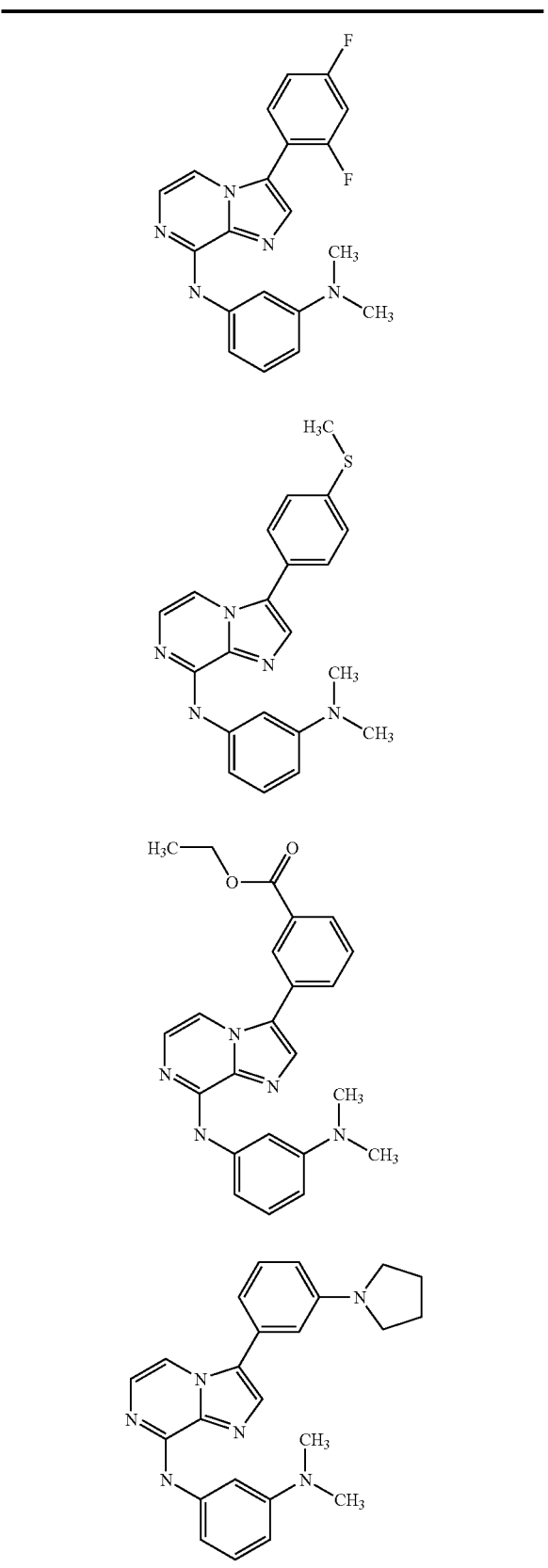
TABLE 1B-continued
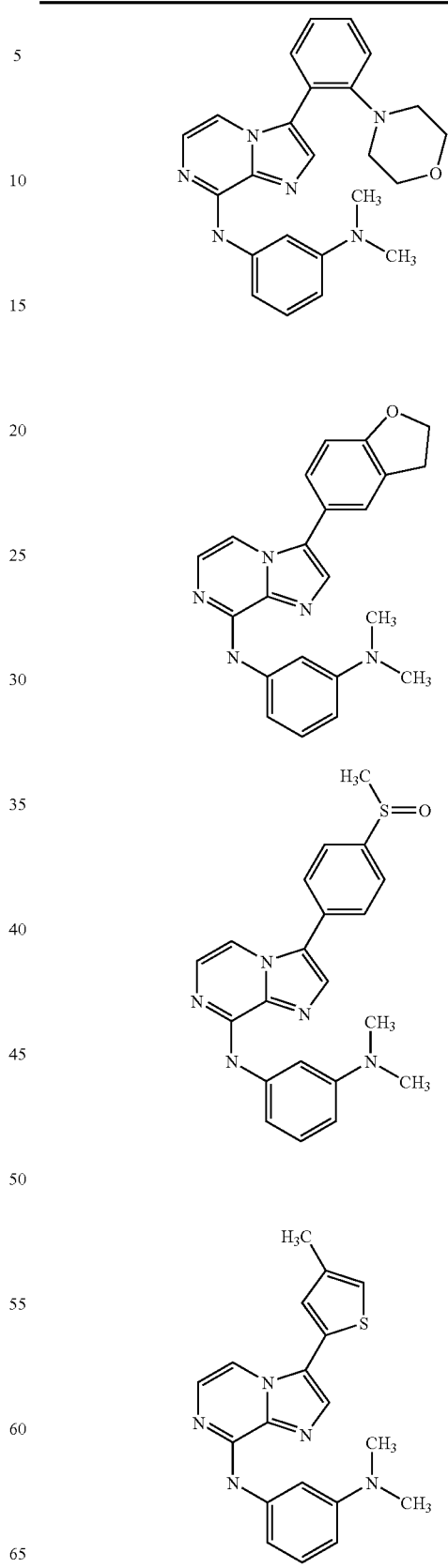

TABLE 1B-continued
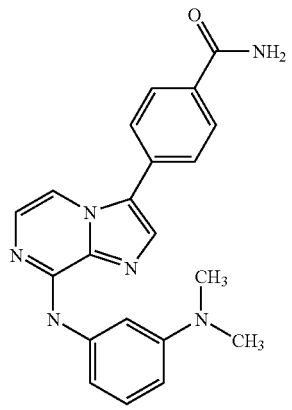
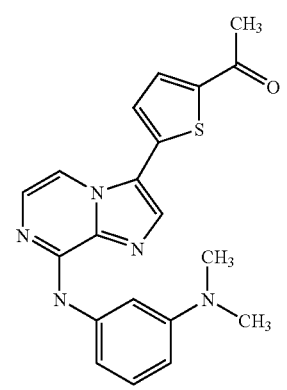
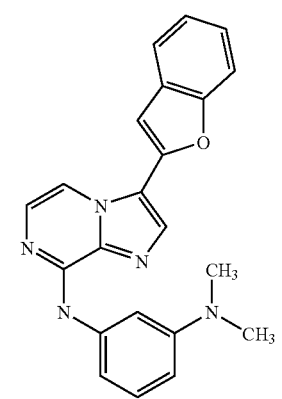
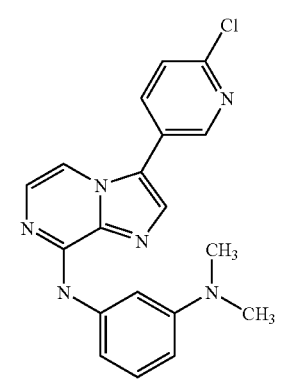
TABLE 1B-continued
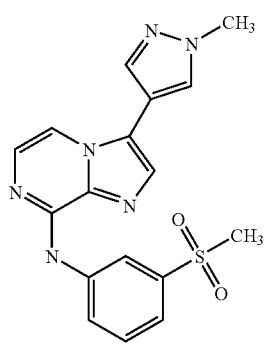
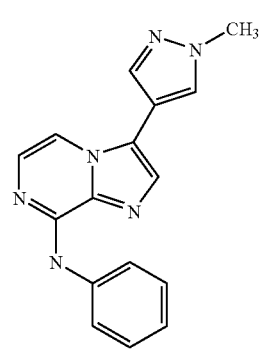
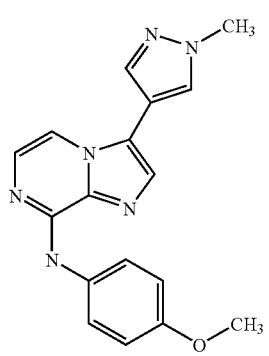
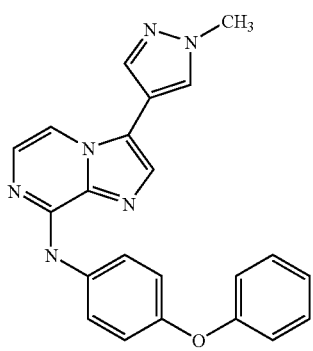

TABLE 1B-continued
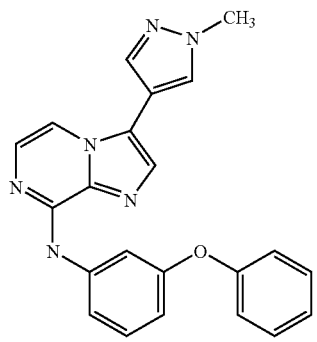
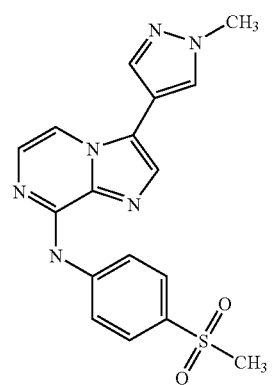
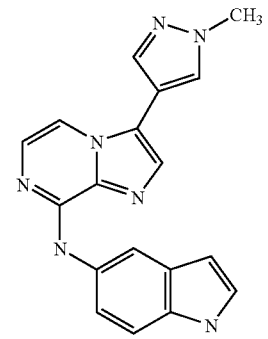
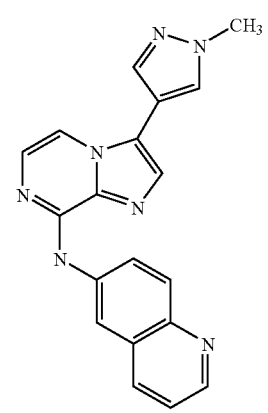
TABLE 1B-continued
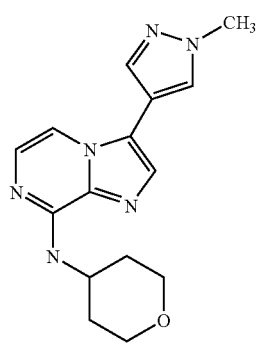
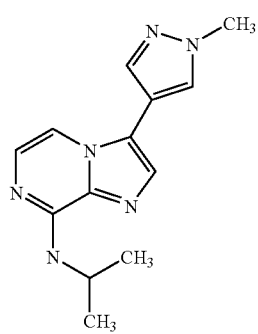
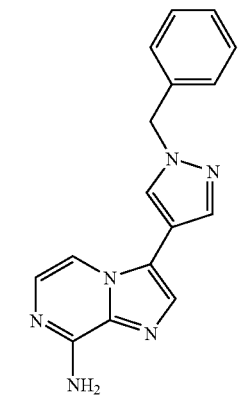
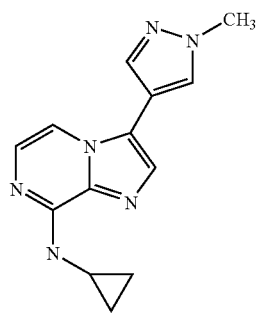

TABLE 1B-continued
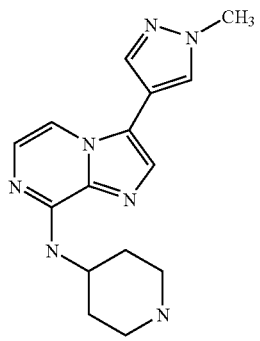
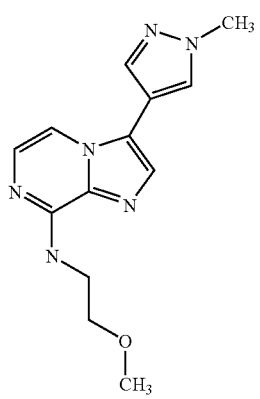
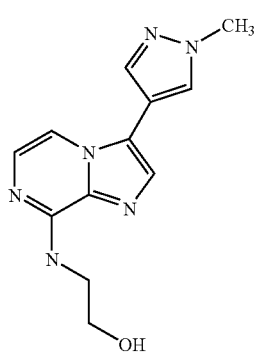
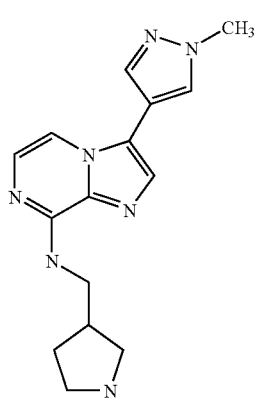
TABLE 1B-continued
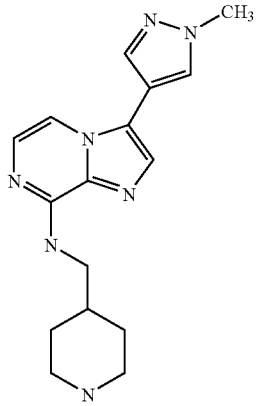
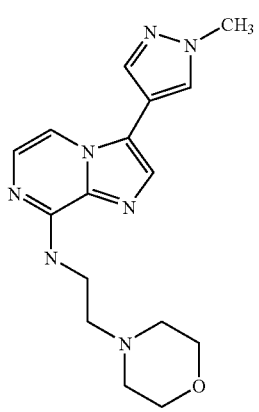
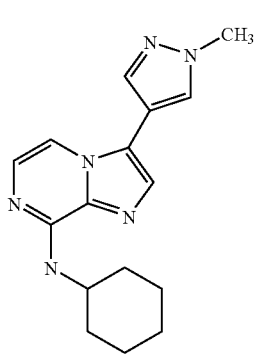
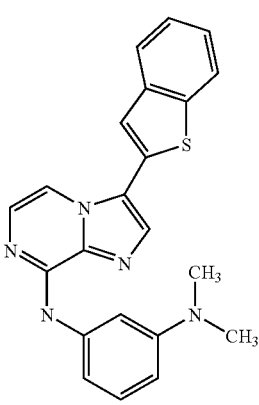

TABLE 1B-continued
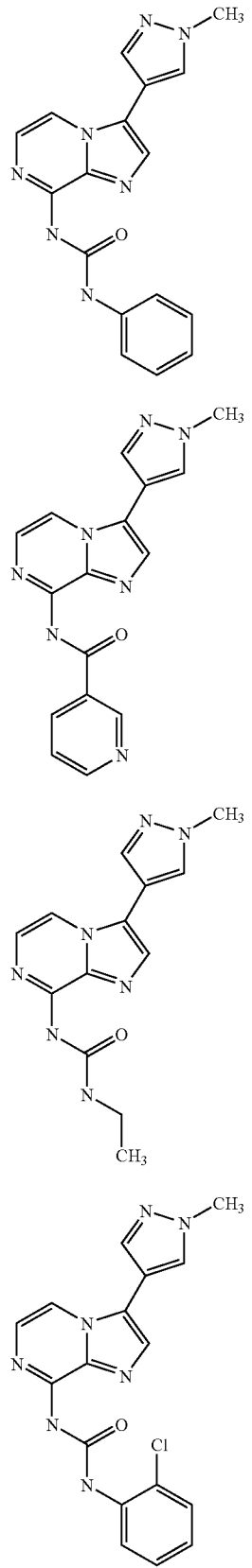
TABLE 1B-continued
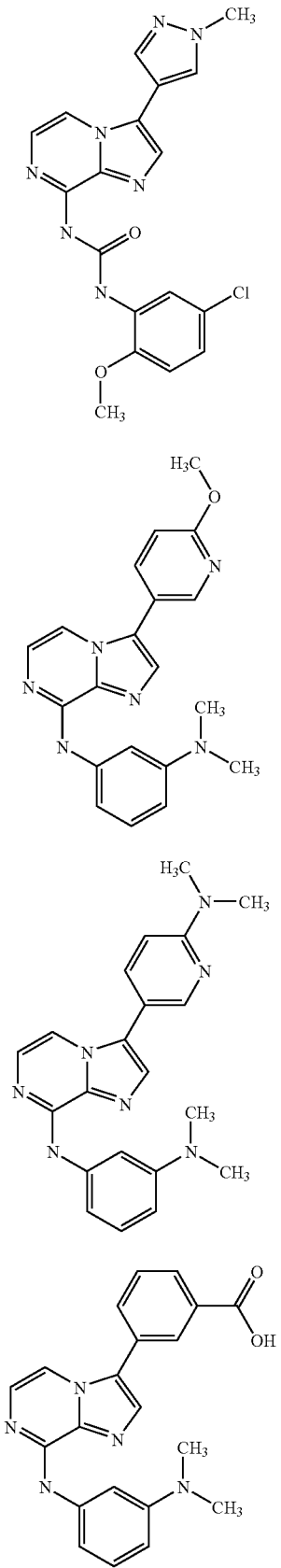

TABLE 1B-continued
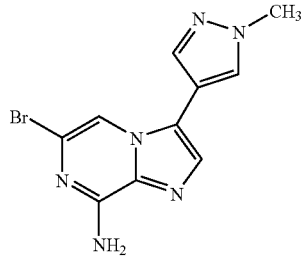
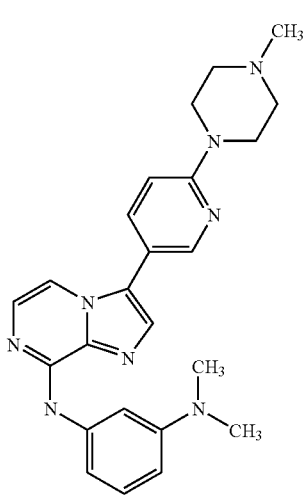
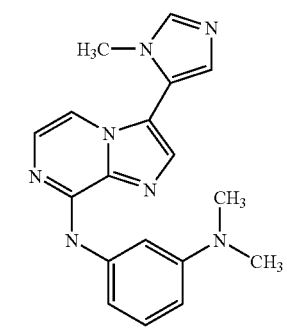
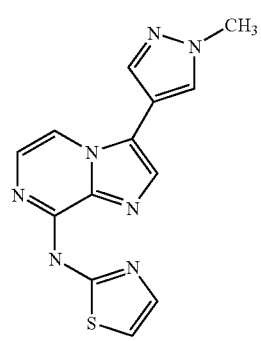
TABLE 1B-continued
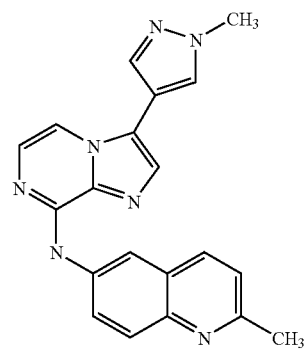
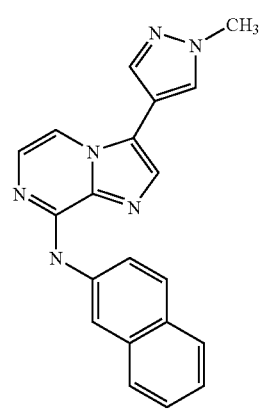
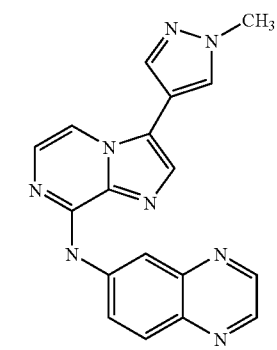
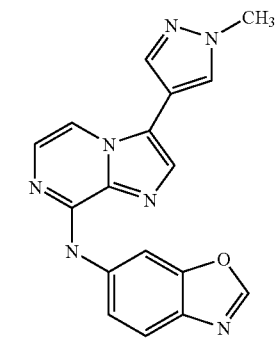

TABLE 1B-continued
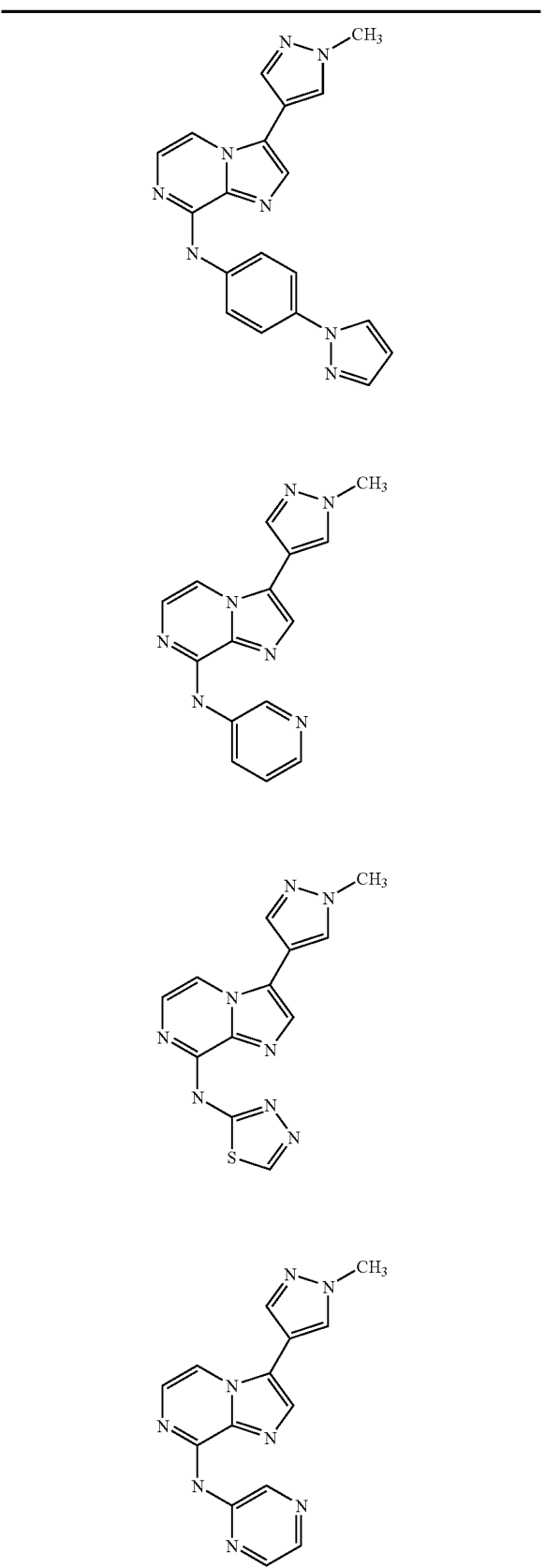
TABLE 1B-continued
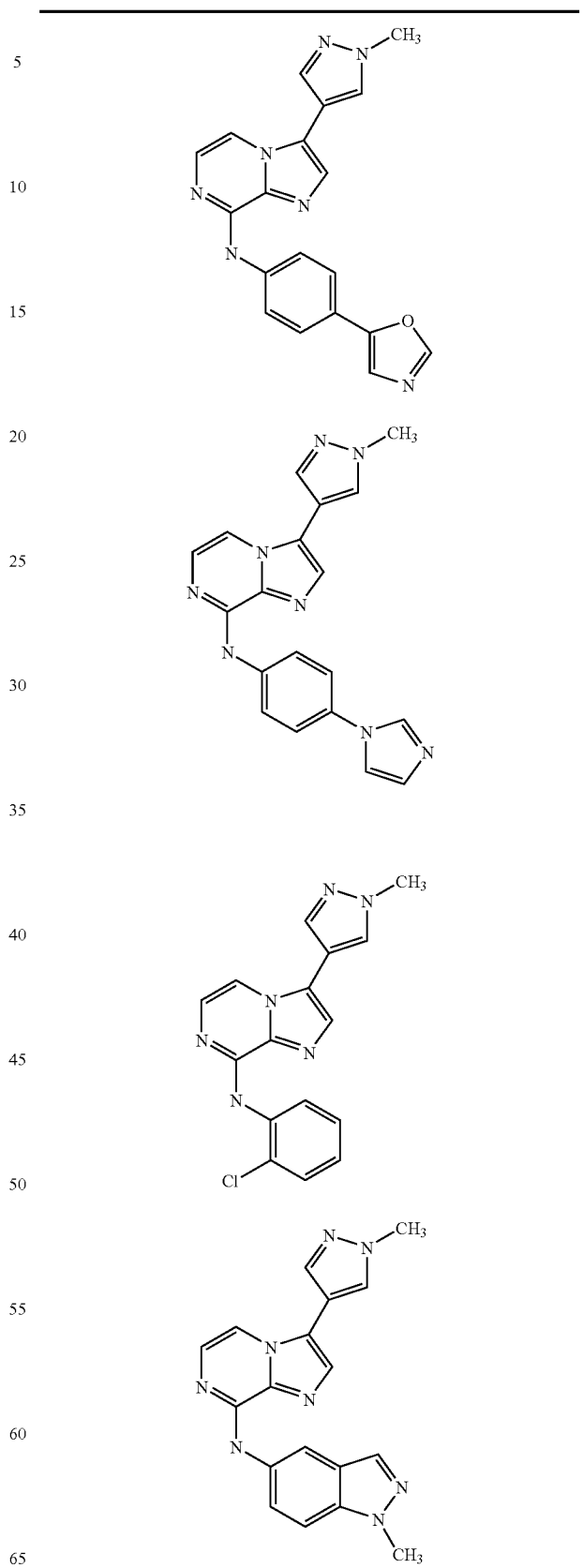

TABLE 1B-continued
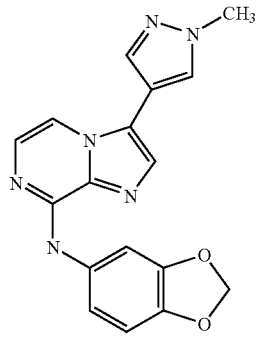
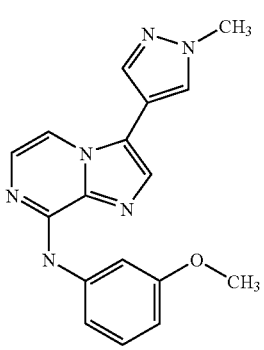
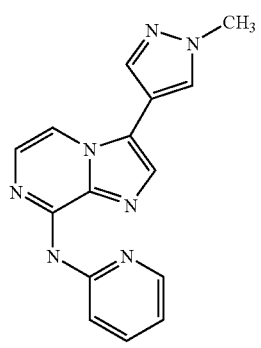
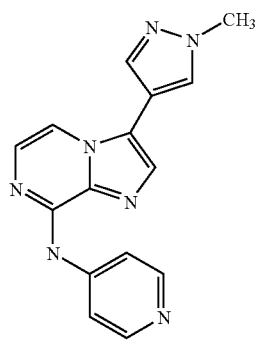
TABLE 1B-continued
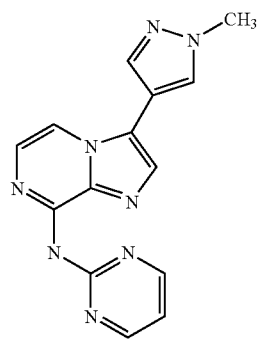
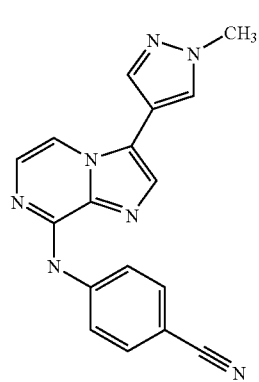
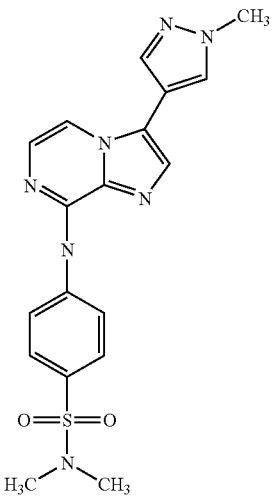

TABLE 1B-continued
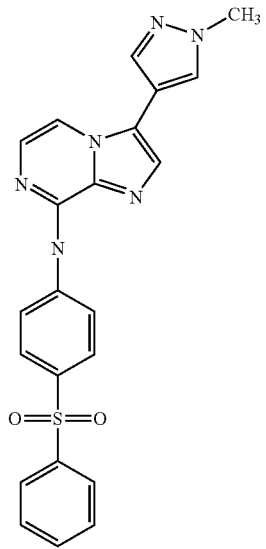
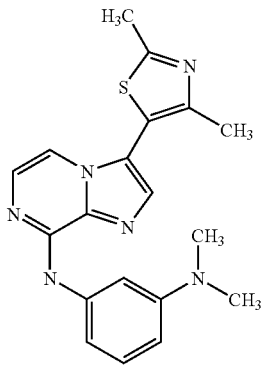
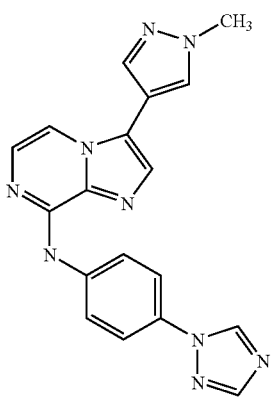
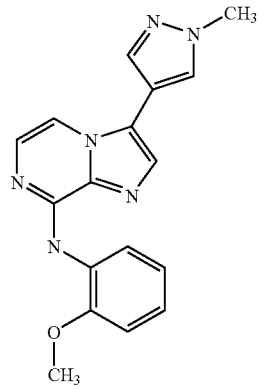
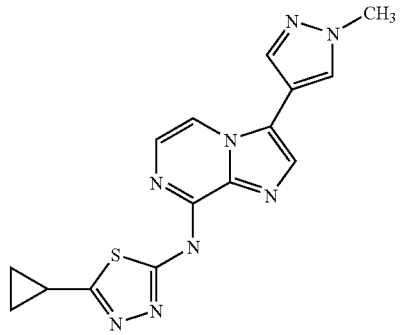

TABLE 1B-continued
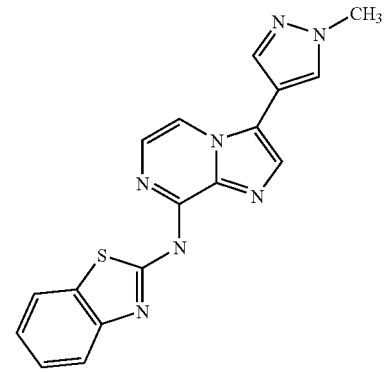
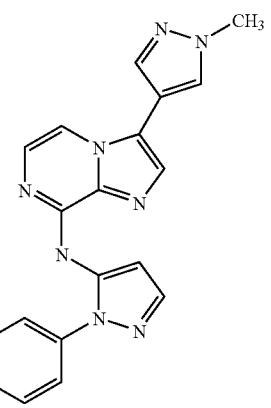
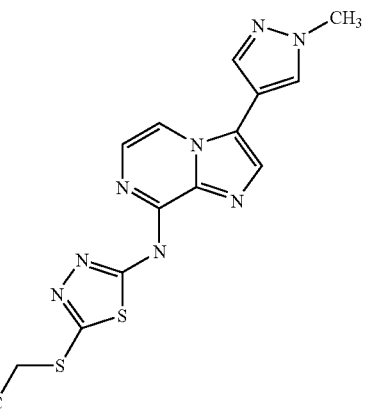
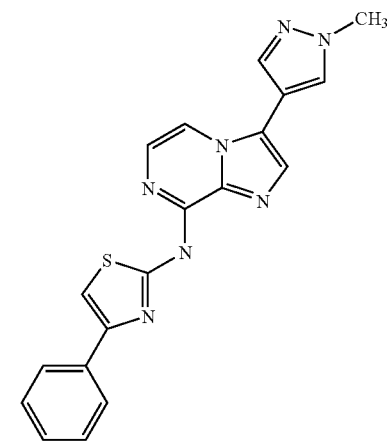
TABLE 1B-continued
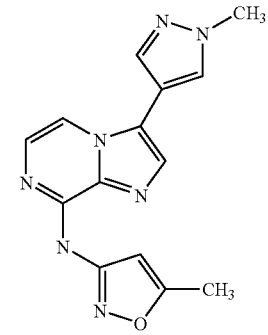
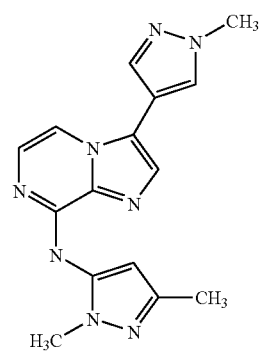
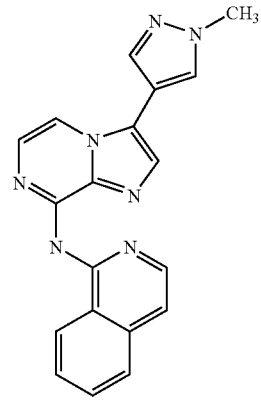
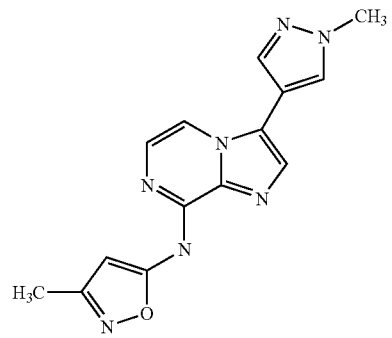

TABLE 1B-continued
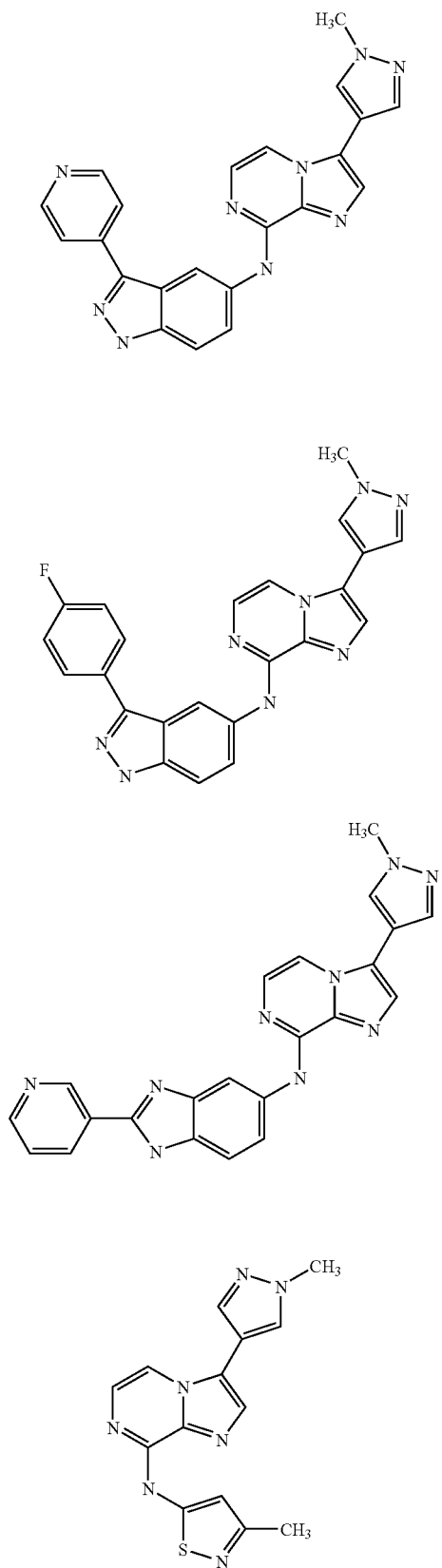
TABLE 1B-continued
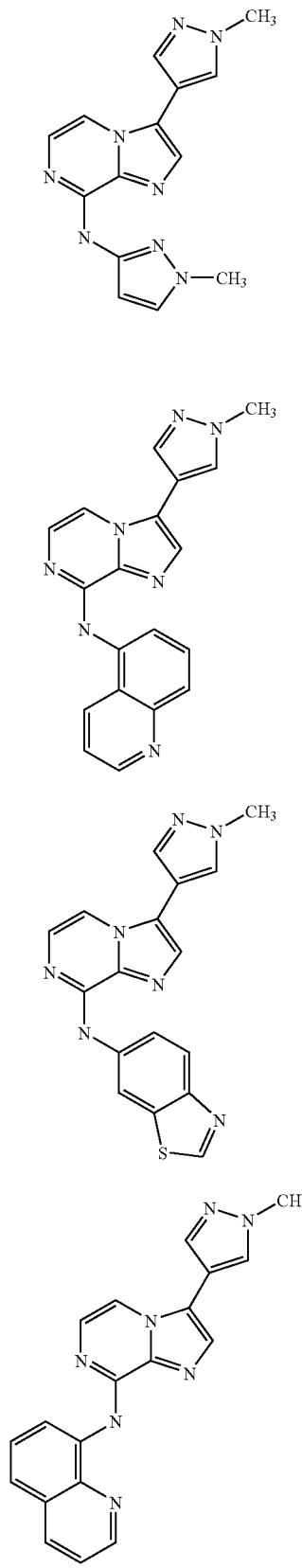

TABLE 1B-continued
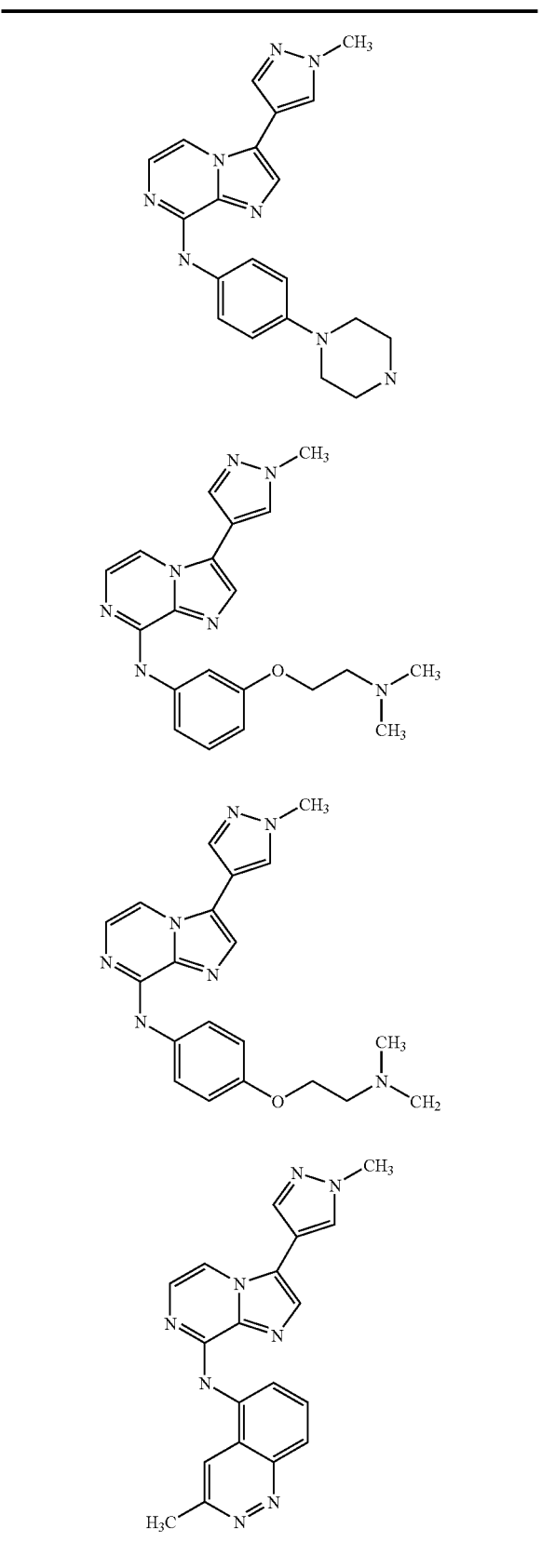
TABLE 1B-continued
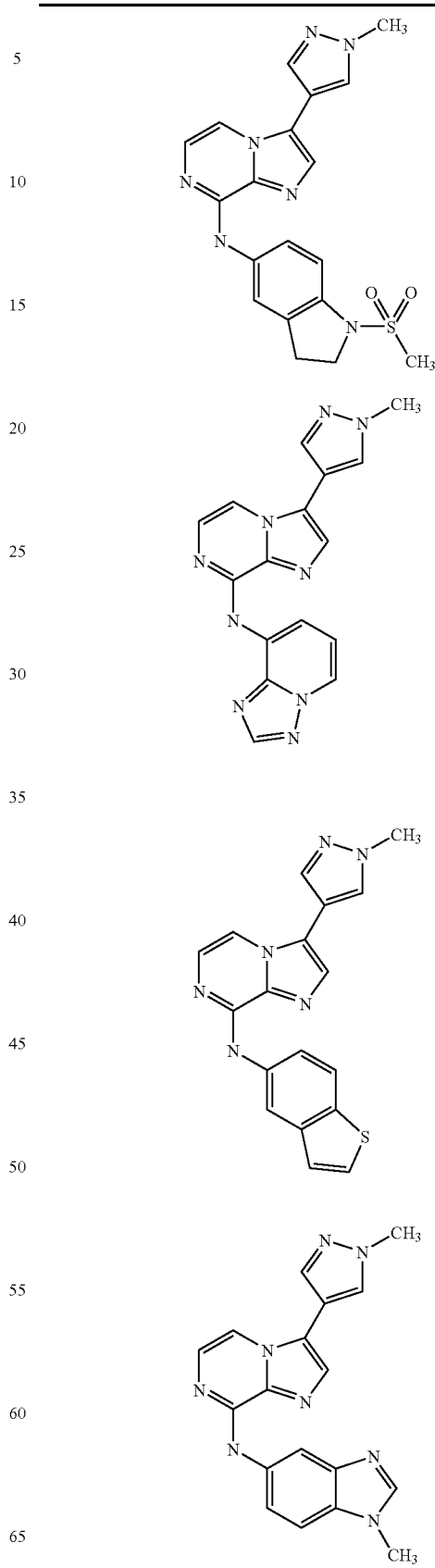

TABLE 1B-continued
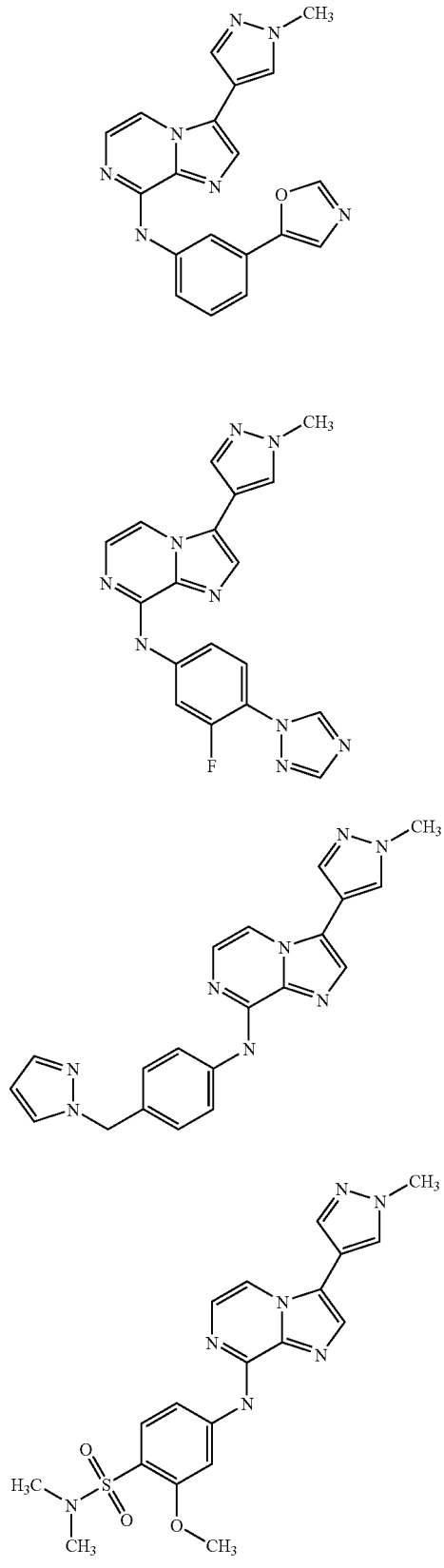
TABLE 1B-continued
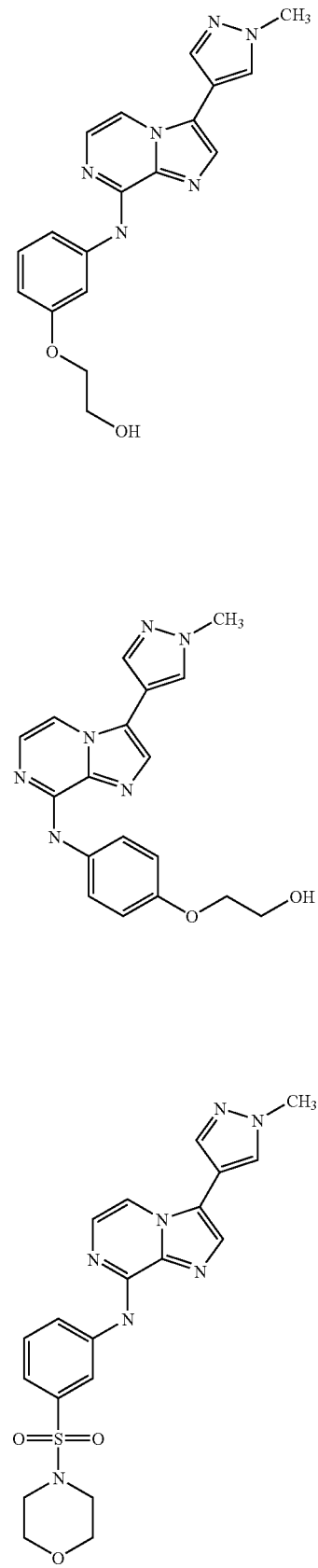

TABLE 1B-continued
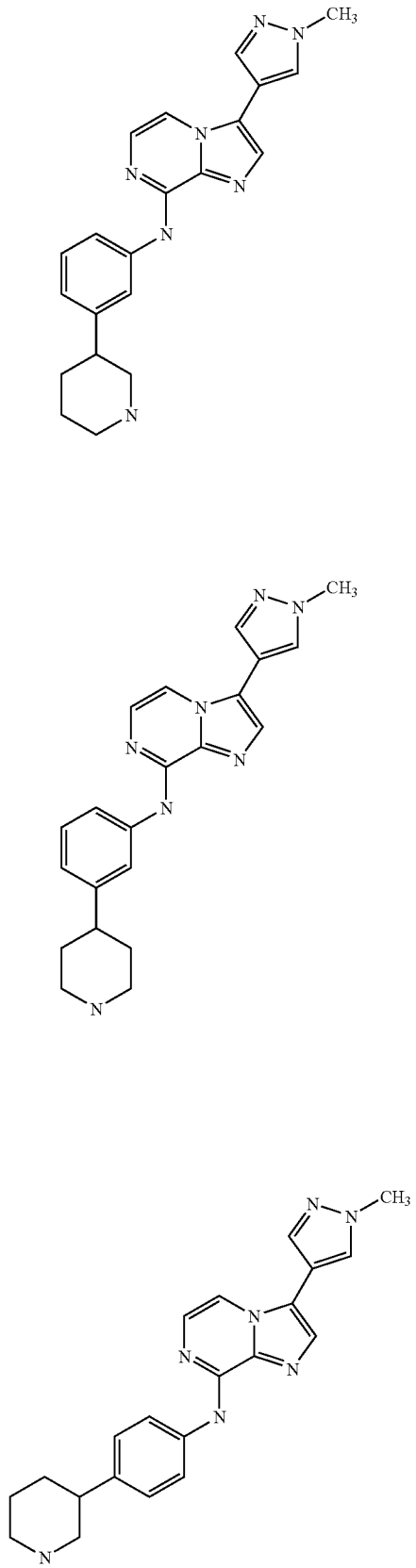
TABLE 1B-continued
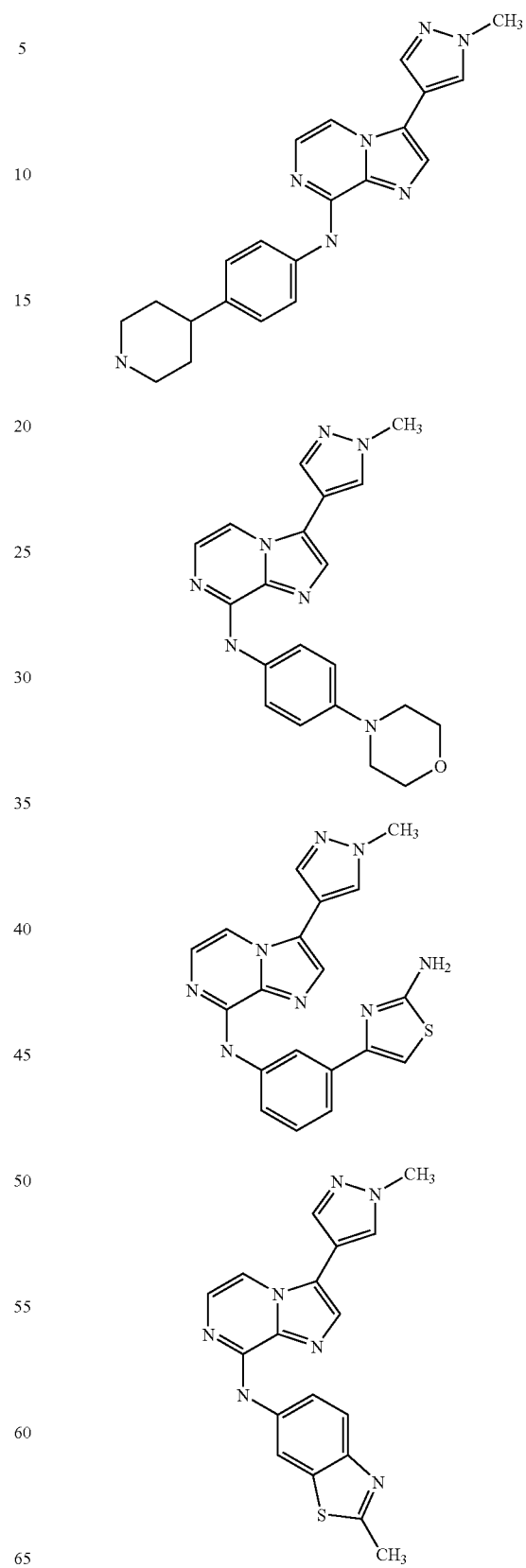

TABLE 1B-continued
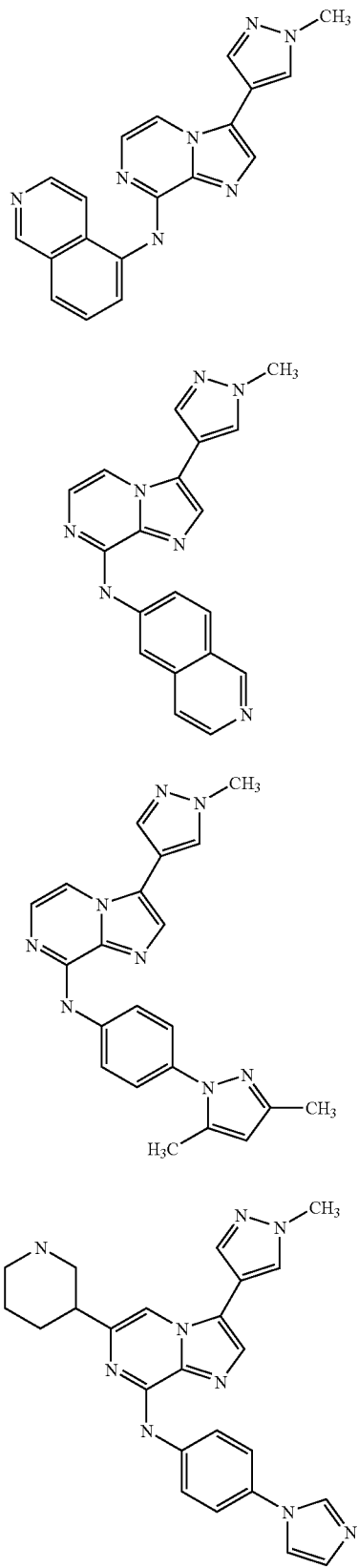
TABLE 1B-continued
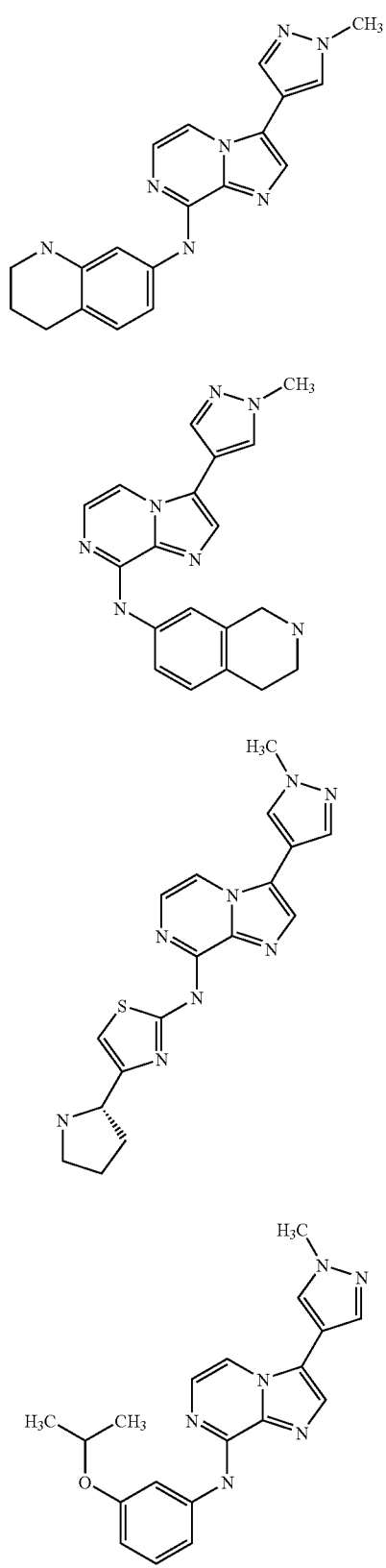

TABLE 1B-continued
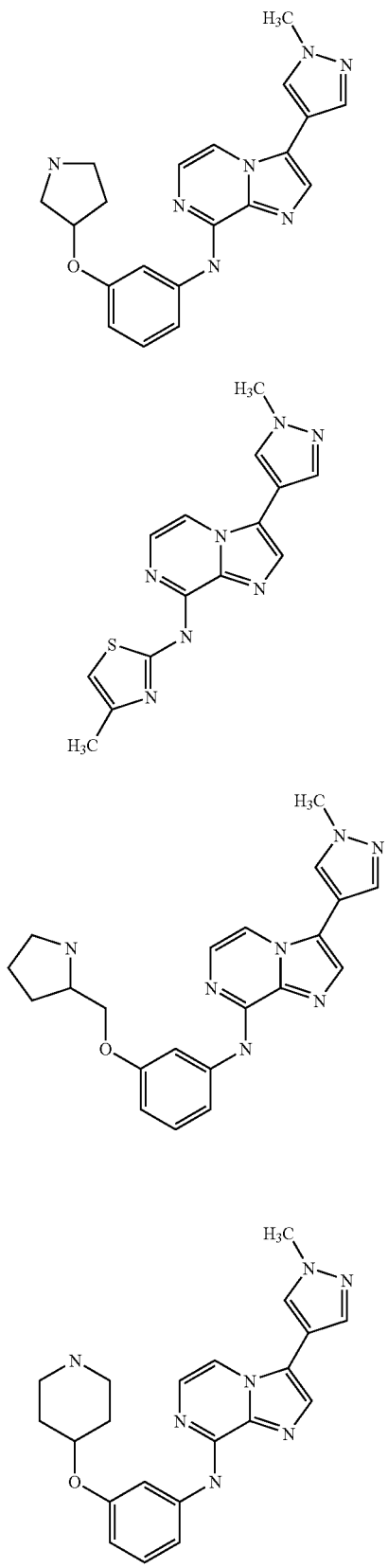
TABLE 1B-continued
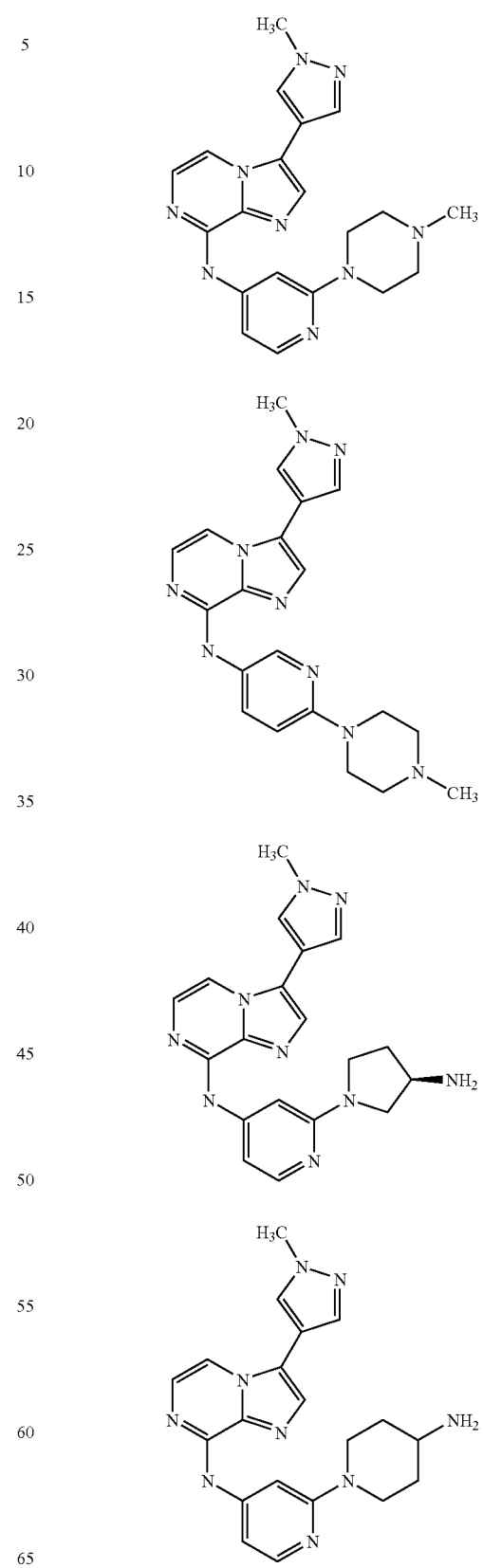

TABLE 1B-continued
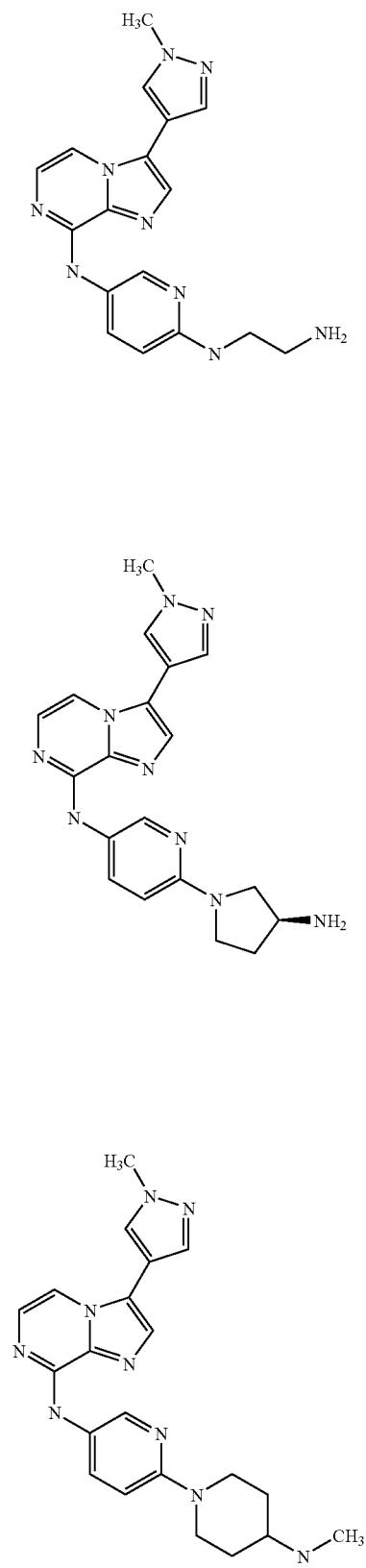
TABLE 1B-continued
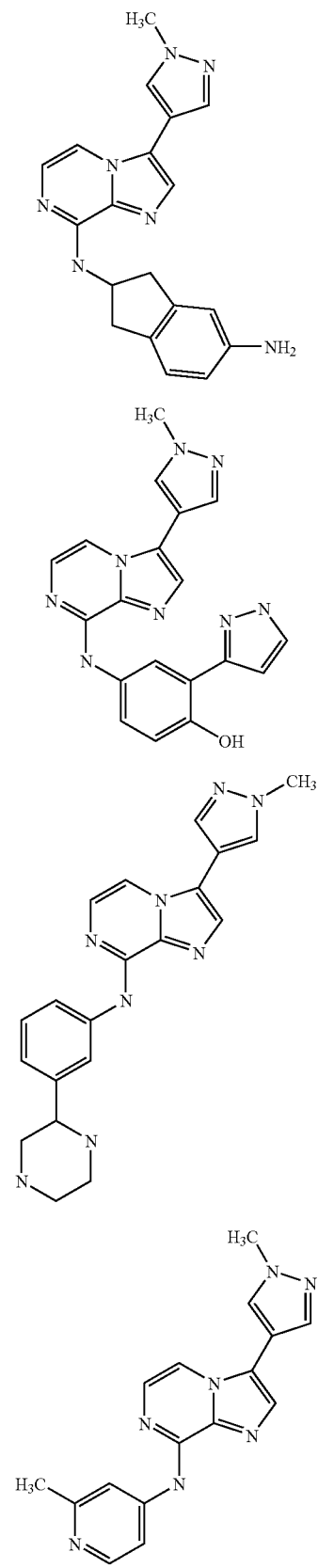

TABLE 1B-continued
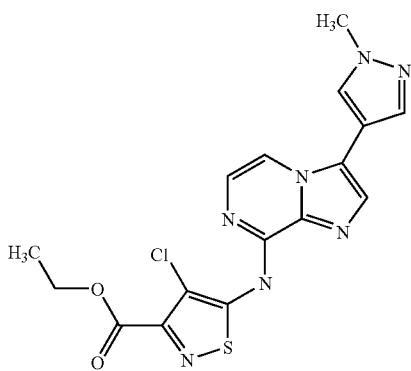
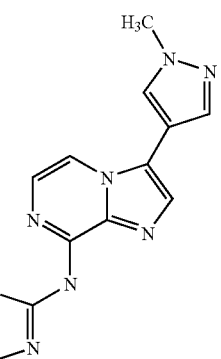
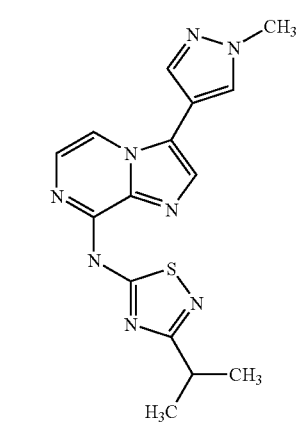
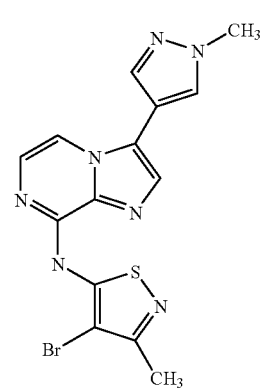
TABLE 1B-continued
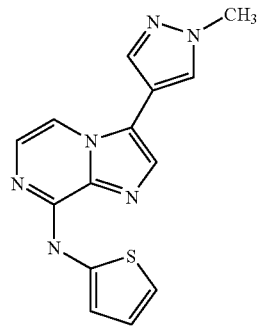
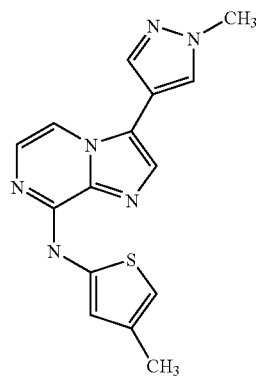
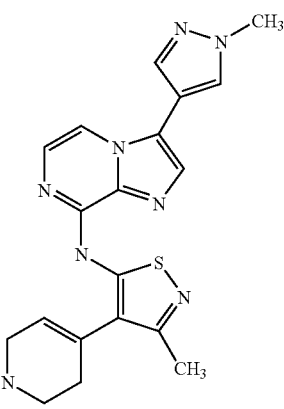
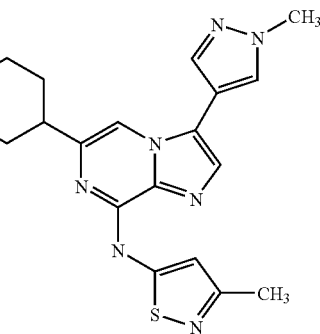

TABLE 1B-continued
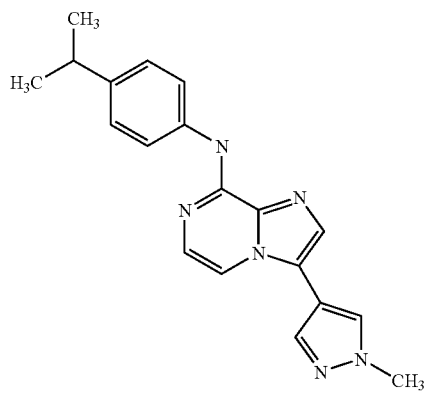
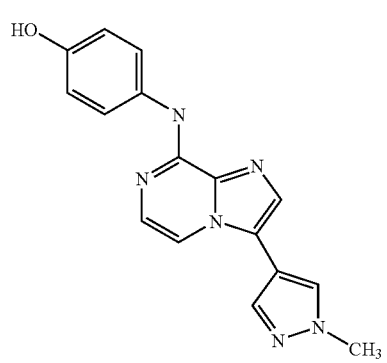
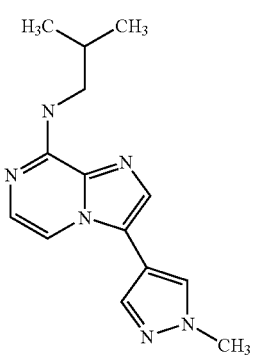
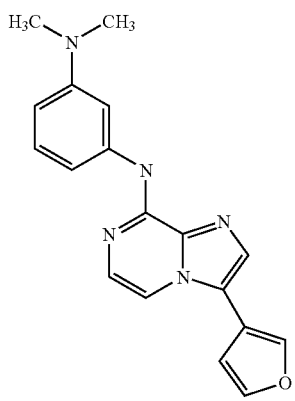
TABLE 1B-continued
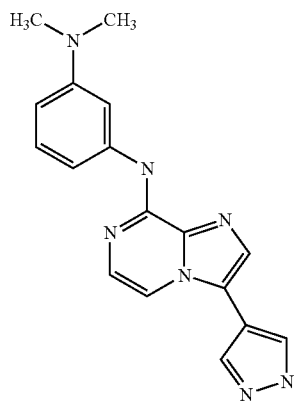
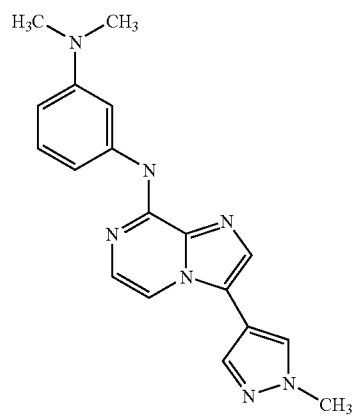
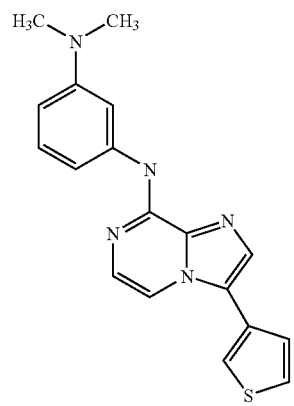
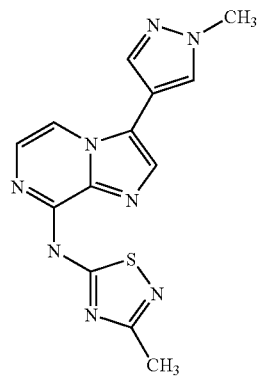

TABLE 1B-continued
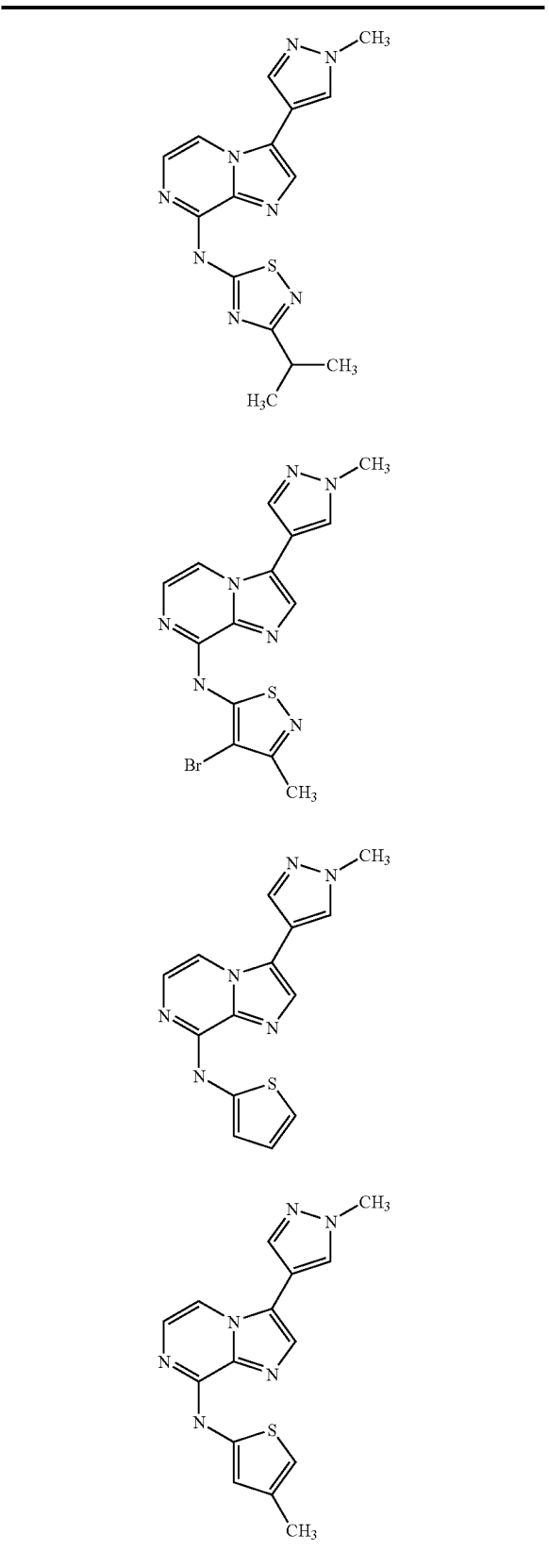
TABLE 1B-continued
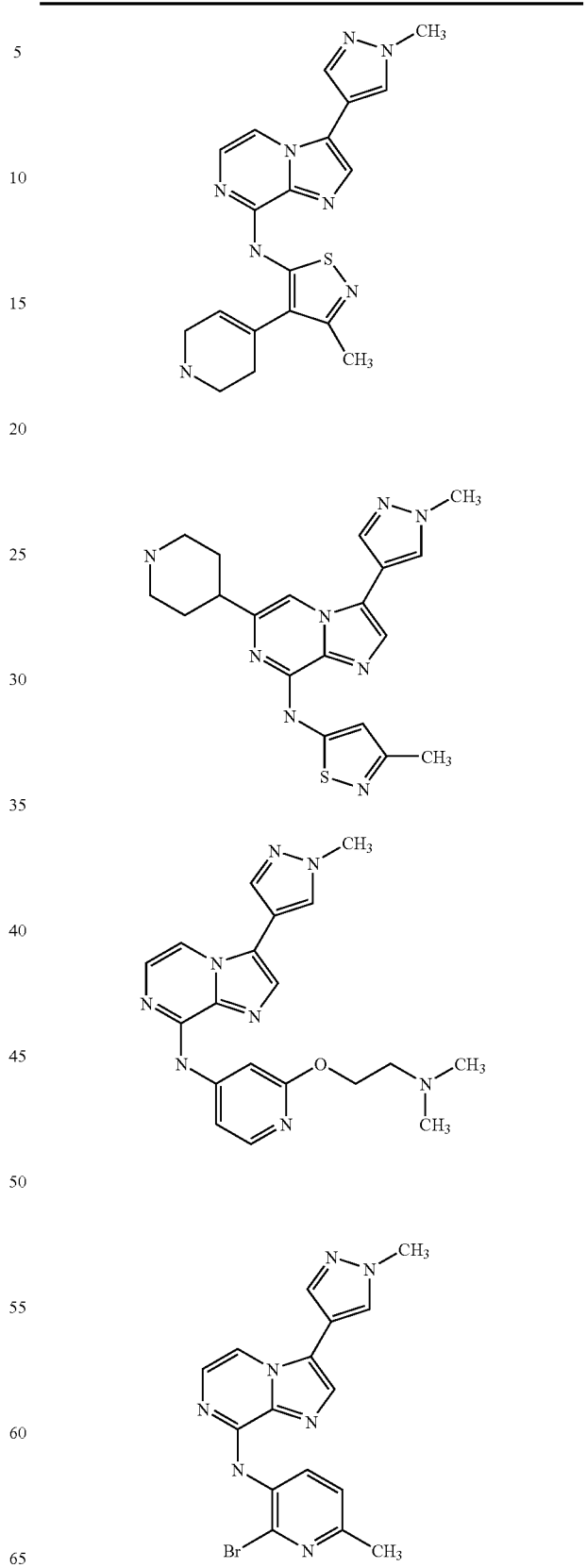

TABLE 1B-continued
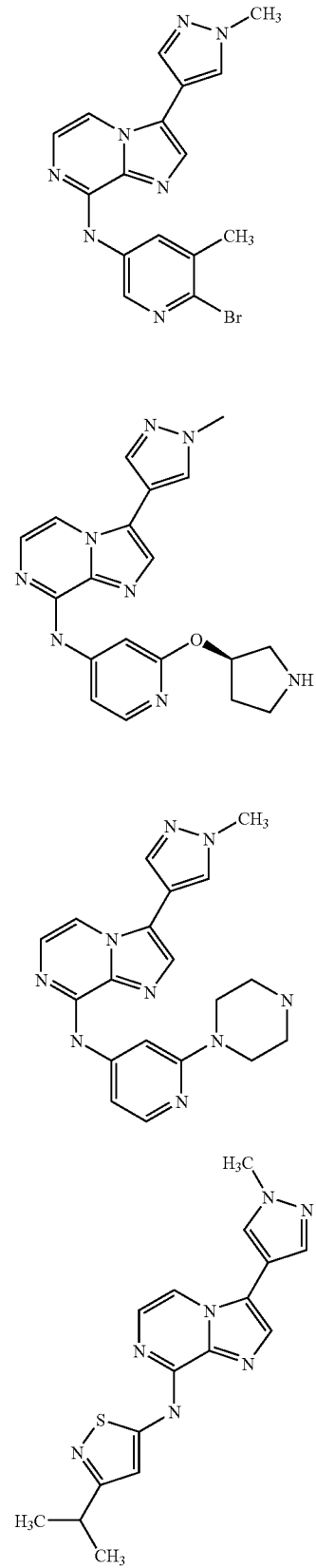
TABLE 1B-continued
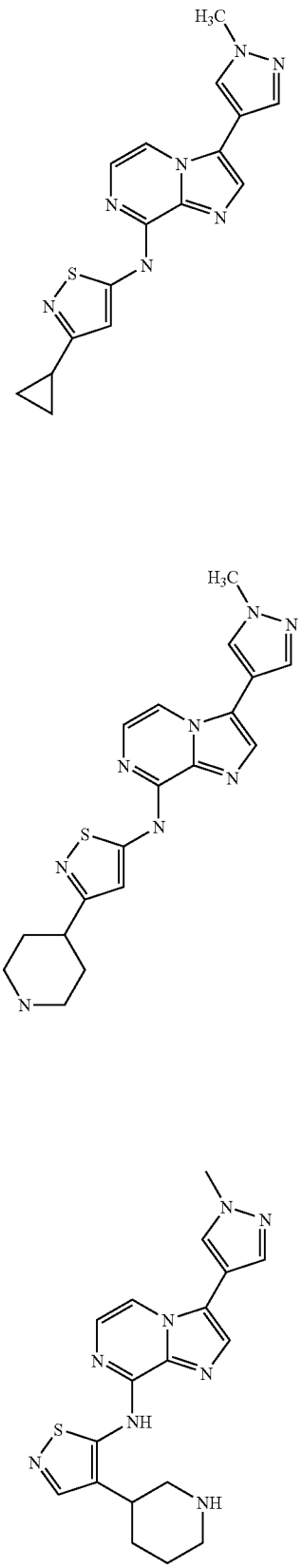

TABLE 1B-continued
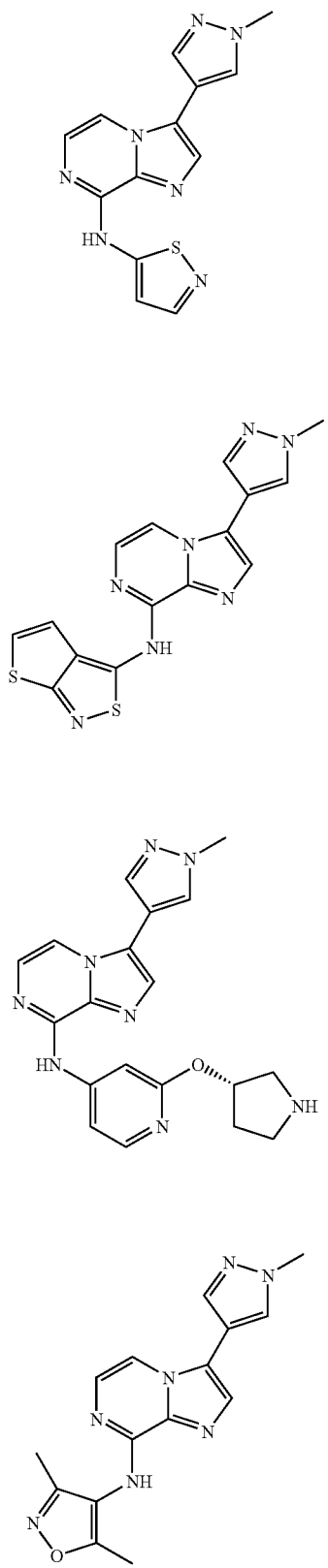
TABLE 1B-continued
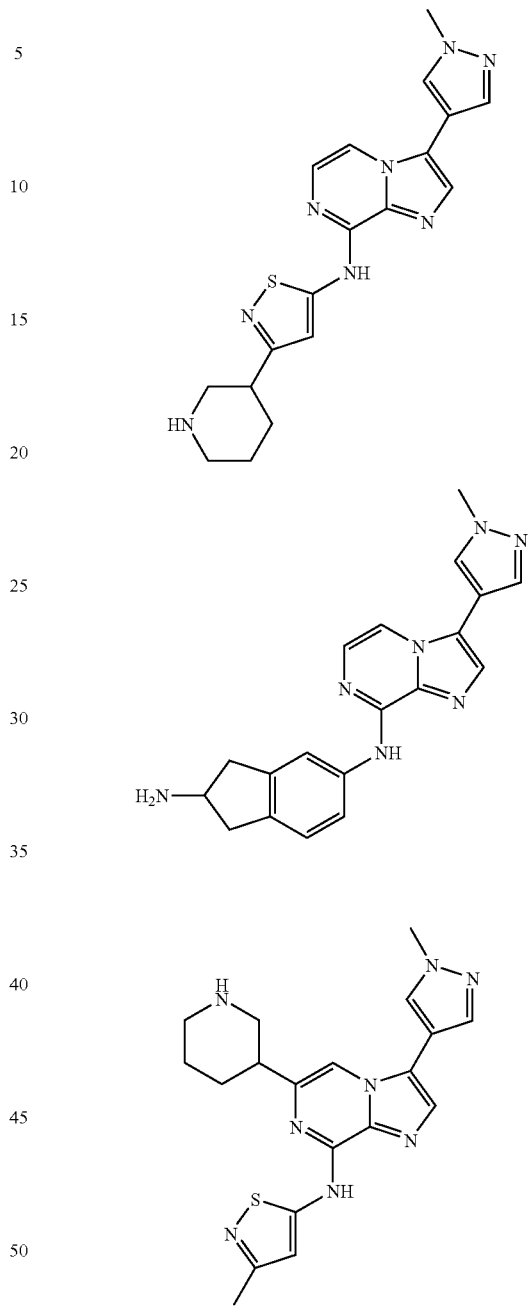
or pharmaceutically acceptable salt, solvate, ester or prodrug thereof.
Also disclosed are the following compounds in Table 1C:
TABLE 1C
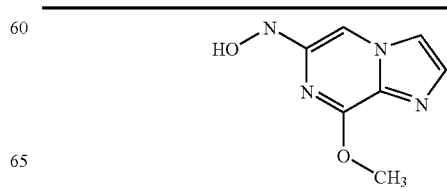

TABLE 1C-continued
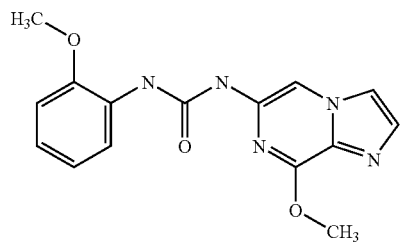
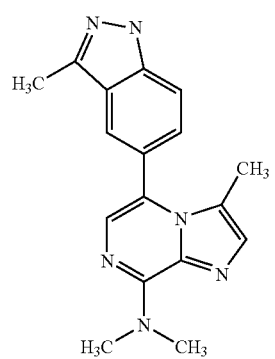
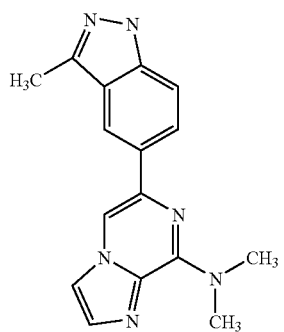
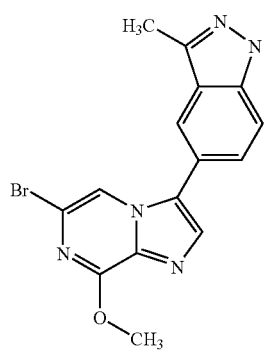
TABLE 1C-continued
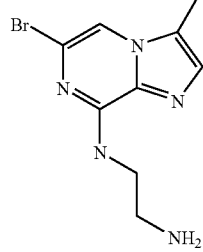
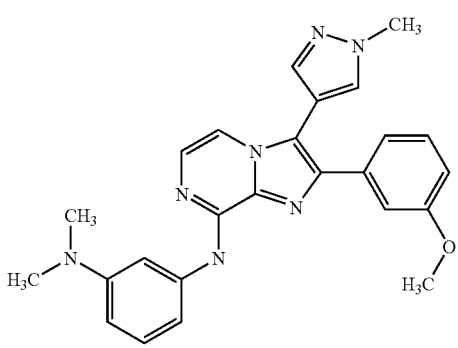
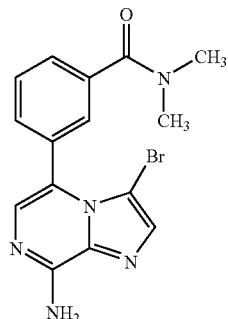
or
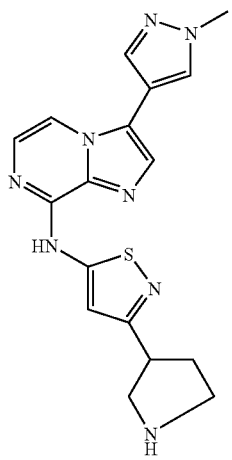

or a pharmaceutically acceptable salt, solvate, or ester thereof.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

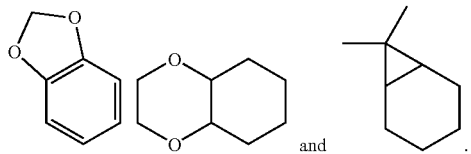

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

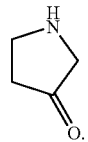

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, dihydroimidazole, dihydrooxazole, dihydrooxadiazole, dihydrothiazole, 3,4-dihydro-2H-pyran, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

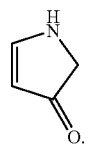

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

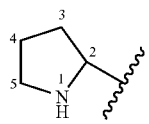

there is no —OH attached directly to carbons marked 2 and 5.

It should also be noted that tautomeric forms such as, for example, the moieties:

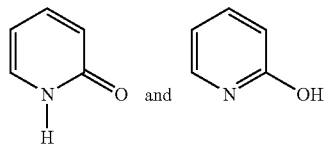

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

h"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycle, $R^2$, etc.) occurs more than one time in any constituent or in Formula III, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O$(C_1-C_6)$alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy $(C_1-C_6)$alkyl, amino $(C_1-C_4)$alkyl or mono-N— or di-N,N-$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula III can form salts which are also within the scope of this invention. Reference to a compound of Formula III herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula III contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula III may be formed, for example, by reacting a compound of Formula III with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection* and Use. (2002) Zurich: Wiley-VCH; S. Berge et al, *Journal of Pharmaceutical Sciences* (1977) 66(1)1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula III, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula III, and of the salts, solvates, esters and prodrugs of the compounds of Formula III, are intended to be included in the present invention.

The compounds according to the invention have pharmacological properties; in particular, the compounds of Formula III can be inhibitors of protein kinases such as, for example, the inhibitors of the cyclin-dependent kinases, mitogen-activated protein kinase (MAPK/ERK), glycogen synthase kinase 3(GSK3beta) and the like. The cyclin dependent kinases (CDKs) include, for example, CDC2 (CDK1), CDK2, CDK4, CDK5, CDK6, CDK7 and CDK8. The novel compounds of Formula III are expected to be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974 cited earlier, the disclosure of which is incorporated herein.

More specifically, the compounds of Formula III can be useful in the treatment of a variety of cancers, including (but not limited to) the following: carcinoma, bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkeft's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of CDKs in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula III may also be useful in the treatment of Alzheimer's disease, as suggested by the recent finding that CDK5 is involved in the phosphorylation of tau protein (J. Biochem, (1995) 117, 741-749).

Compounds of Formula III may induce or inhibit apoptosis. The apoptotic response is aberrant in a variety of human diseases. Compounds of Formula III, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula III, as inhibitors of the CDKs, can modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula III may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula III may also be useful in inhibiting tumor angiogenesis and metastasis.

Compounds of Formula III may also act as inhibitors of other protein kinases, e.g., protein kinase C, her2, raf 1, MEK1, MAP kinase, EGF receptor, PDGF receptor, IGF receptor, P13 kinase, weel kinase, Src, Abl and thus be effective in the treatment of diseases associated with other protein kinases.

Another aspect of this invention is a method of treating a mammal (e.g., human) having a disease or condition associated with the CDKs by administering a therapeutically effective amount of at least one compound of Formula III, or a pharmaceutically acceptable salt or solvate of said compound to the mammal.

A preferred dosage is about 0.001 to 500 mg/kg of body weight/day of the compound of Formula III. An especially preferred dosage is about 0.01 to 25 mg/kg of body weight/day of a compound of Formula III, or a pharmaceutically acceptable salt or solvate of said compound.

The compounds of this invention may also be useful in combination (administered together or sequentially) with one or more of anti-cancer treatments such as radiation therapy, and/or one or more anti-cancer agents selected from the group consisting of cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methoxtrexate); alkylating agents (such as temozolomide (TEMODAR™ from Schering-Plough Corporation, Kenilworth, N.J.), cyclophosphamide); Farnesyl protein transferase inhibitors (such as, SARASAR™(4-[2-[4-[(11R)-3,10-dibromo-8-chloro-6,11-dihydro-5H-benzo[5,6]cyclohepta[1,2-b]pyridin-11-yl-]-11-piperidinyl]-2-oxoehtyl]-1-piperidinecarboxamide, or SCH 66336 from Schering-Plough Corporation, Kenilworth, N.J.), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa (from Astra Zeneca Pharmaceuticals, England), Tarceva (EGFR kinase inhibitors), antibodies to EGFR (e.g., C225), GLEEVEC™ (C-abl kinase inhibitor from Novartis Pharmaceuticals, East Hanover, N.J.); interferons such as, for example, intron (from Schering-Plough Corporation), Peg-Intron (from Schering-Plough Corporation); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaeuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine.

If formulated as a fixed dose, such combination products employ the compounds of this invention within the dosage range described herein and the other pharmaceutically active agent or treatment within its dosage range. For example, the CDC2 inhibitor olomucine has been found to act synergistically with known cytotoxic agents in inducing apoptosis (*J. Cell Sci.*, (1995) 108, 2897. Compounds of Formula III may also be administered sequentially with known anticancer or cytotoxic agents when a combination formulation is inappropriate. The invention is not limited in the sequence of administration; compounds of Formula III may be administered either prior to or after administration of the known anticancer or cytotoxic agent. For example, the cytotoxic activity of the cyclin-dependent kinase inhibitor flavopiridol is affected by the sequence of administration with anticancer agents. *Cancer Research*, (1997) 57, 3375. Such techniques are within the skills of persons skilled in the art as well as attending physicians.

Accordingly, in an aspect, this invention includes combinations comprising an amount of at least one compound of Formula ll, or a pharmaceutically acceptable salt or solvate thereof, and an amount of one or more anti-cancer treatments and anti-cancer agents listed above wherein the amounts of the compounds/treatments result in desired therapeutic effect.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula ll, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula III, or a pharmaceutically acceptable salt or solvate of said compound and a pharmaceutically acceptable carrier, vehicle or diluent.

Yet another aspect of this invention is a kit comprising an amount of at least one compound of Formula III, or a pharmaceutically acceptable salt or solvate of said compound and an amount of at least one anticancer therapy and/or anticancer agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

The following solvents and reagents may be referred to by their abbreviations in parenthesis:
Thin layer chromatography: TLC
dichloromethane: CH$_2$Cl$_2$
ethyl acetate: AcOEt or EtOAc
methanol: MeOH
trifluoroacetate: TFA
triethylamine: Et$_3$N or TEA
butoxycarbonyl: N-Boc or Boc
nuclear magnetic resonance spectroscopy: NMR
liquid chromatography mass spectrometry: LCMS
high resolution mass spectrometry: HRMS
milliliters: mL
millimoles: mmol
microliters: μl
grams: g
milligrams: mg
room temperature or rt (ambient): about 25° C.

EXAMPLES

Preparative Example 1

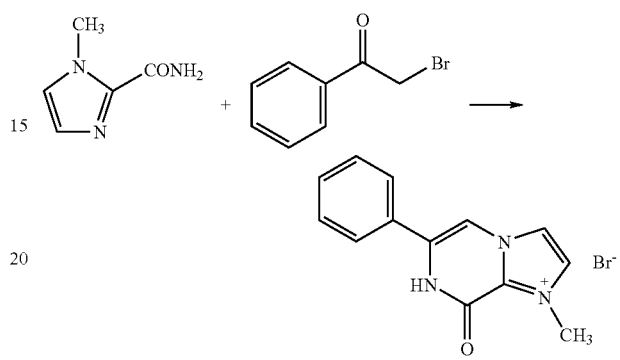

A mixture of 1-methylimidazole-2-carboxamide (3.00 g, 24 mmol) and phenacyl bromide (5.73 g, 29 mmol) in anhydrous CH$_3$CN (90 mL) was stirred and refluxed under N$_2$ for 1 day. The mixture was filtered, the solid was washed on filter with CH$_3$CN (2×30 mL) and dried in a vacuum. White solid (5.86 g, 80%) was obtained.

Preparative Example 1.1 and 1.2

By essentially the same procedure given in Preparative Example 1, compounds given in Column 2 of Table 1.1 can be prepared by combining 1-methylimidazole-2-carboxamide with the bromoketones given in Column 1.

TABLE 1.1

| Prep. Example | Column 1 | Column 2 |
|---|---|---|
| 1.1 | | |
| 1.2 | | |

Preparative Example 2

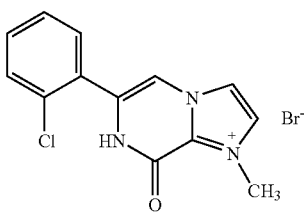

This compound was prepared by essentially same procedure set forth in Preparative Example 1.

Preparative Example 3

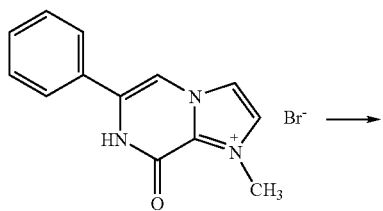

A mixture of the product from Preparative Example 1 (4.62 g, 15 mmol) and imidazole (25.50 g, 375 mmol) was stirred under $N_2$ at 175° C. for 20 hr, then it was cooled to 100° C. and poured into stirred ice-cold water (400 mL). The mixture was stirred for 15 min, and then filtered. The solid was washed on filter with water (2×100 mL) and dried in a vacuum at 100° C. White solid (2.43 g, 77%) was obtained.

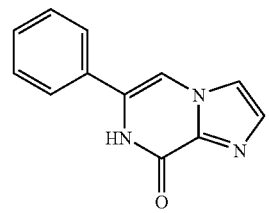

Preparative Example 3.1 and 3.2

By essentially the same procedure given in Preparative Example 3, compounds given in Column 2 of Table 2.1 can be prepared from compounds given in Column 1.

TABLE 2.1

| Prep. Example | Column 1 | Column 2 |
|---|---|---|
| 3.1 | *(structure)* | *(structure)* |
| 3.2 | *(structure)* | *(structure)* |

Preparative Example 4

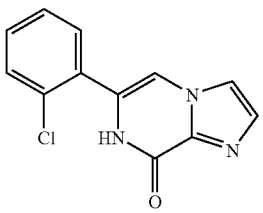

Method 1:

This compound was prepared by essentially same procedure set forth in Preparative Example 3. LCMS; MH$^+$=246.

Method 2:

Pyridinium hydrochloride (378.6 g, 3.28 moles) was placed in a 2 L round bottomed flask and heated under reflux under a gentle stream of nitrogen until all of the material had melted. The title compound from Preparative Example 2 [31.64 g crude, prepared from 1-methylimidazole-2-carboxamide (10 g, 79.9 mmoles) essentially as described in Preparative Example 2] was added in one portion and the mixture was heated under reflux at 215° C. for 15 min. The hot solution was poured into a mixture of 1.6 L of ice and conc. NH$_4$OH (500 mL). The pH was ~10.5. The mixture was evaporated to dryness and stored in the freezer. The resulting material was triturated with MeOH (4 L), filtered and the solids were washed with additional MeOH (2 L). The combined filtrates were evaporated to dryness to give a solid (49.75 g). The latter was broken up and triturated with distilled water (250 mL) and then filtered. The filtrate was discarded and the solid was dissolved in hot MeOH (850 mL).and added to silica gel (~800 mL) and Sea Sand (~350 mL) and the mixture was evaporated to dryness. The resulting mixture was introduced as a plug on to a silica gel column (40×9 cm) and the latter was eluted with CH$_2$Cl$_2$ (4 L), followed by 1%-2.5% MeOH in CH$_2$Cl$_2$ and then neat MeOH, to give the title compound (8.06 g, 41%): FABMS: m/z 246.0 (MH$^+$); HRFABMS: m/z 246.0434 (MH$^+$), C$_{12}$H$_9$ClN$_3$O requires: m/z 246.0434.

Preparative Example 5

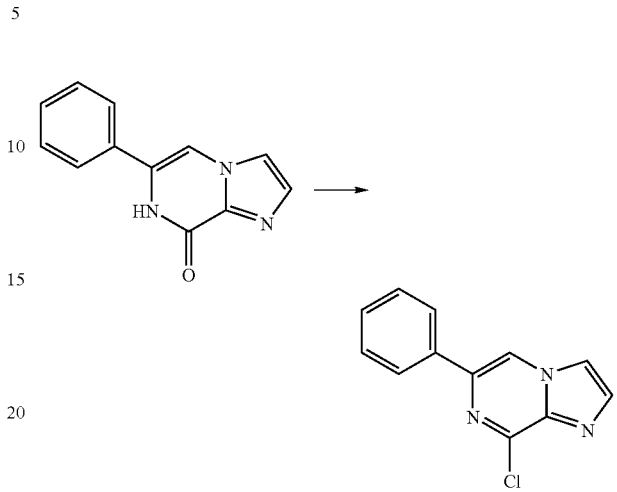

A mixture of the product from Preparative Example 3 (1.20 g, 5.71 mmol) and pyridine (0.32 mL, 4.0 mmol) in POCl$_3$ (6.5 mL) was stirred and refluxed under N$_2$ for 5 hrs. The mixture was poured into 100 mL of ice, a solution of NaOH (10 g) in H$_2$O (100 mL) was added, and the mixture was extracted with CH$_2$Cl$_2$ (4×50 mL). The extracts were dried over Na$_2$SO$_4$, filtered and the solvent was evaporated. Column chromatography on silica gel with CH$_2$Cl$_2$/EtOAc (2:1) afforded off-white solid (520 mg, 40%).

Preparative Example 5.1 and 5.2

By essentially the same procedure given in Preparative Example 5, compounds given in Column 2 of Table 3.1 can be prepared from compounds given in Column 1.

TABLE 3.1

| Prep. Example | Column 1 | Column 2 |
|---|---|---|
| 5.1 | (structure) | (structure) |
| 5.2 | (structure) | (structure) |

Preparative Example 6

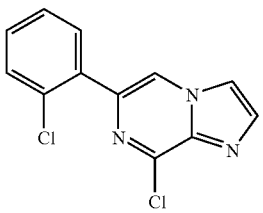

This compound was prepared by essentially same procedure set forth in Preparative Example 5. Off-white solid; LCMS; MH⁺=264.

Preparative Example 7

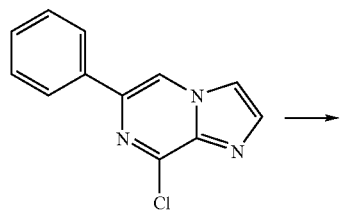 →

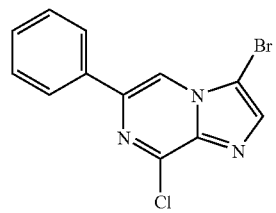

A solution of N-Bromosuccinimide ("NBS") (180 mg, 1.0 mmol) in anhydrous $CH_3CN$ (5 mL) was added under $N_2$ to a stirred solution of the product from Preparative Example 5 (230 mg, 1.0 mmol) in anhydrous $CH_3CN$ (5 mL) and $CH_2Cl_2$ (3 mL). The mixture was stirred at 25° C. for 5 hr and the solvent was then evaporated. Chromatography on silica gel with $CH_2Cl_2$/EtOac (10:1) afforded white solid (294 mg, 96%).

Preparative Example 7.1 and 7.2

By essentially the same procedure given in Preparative Example 7, compounds given in Column 2 of Table 4.1 can be prepared from compounds given in Column 1.

TABLE 4.1

| Prep. Example | Column 1 | Column 2 |
|---|---|---|
| 7.1 | (structure) | (structure) |
| 7.2 | (structure) | (structure) |

Preparative Example 8

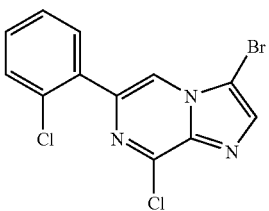

This compound was prepared by essentially same procedure set forth in Preparative Example 7. White solid; LCMS; MH$^+$=342.

Preparative Example 9

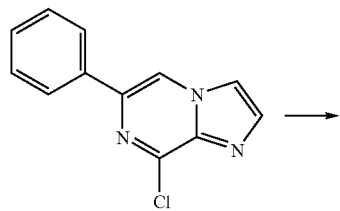

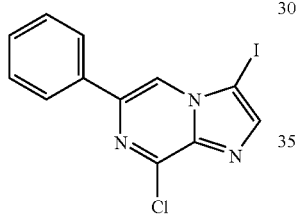

A solution of N-iodosuccinimide ("NIS") (450 mg, 2.0 mmol) in anhydrous CH$_3$CN (10 mL) was added under N$_2$ to a stirred solution of the product from Preparative Example 5 (460 mg, 2.0 mmol) in anhydrous CH$_3$CN (6 mL) and 1,2-dichloroethane (10 mL). The mixture was refluxed for 30 hr and the solvent was then evaporated. Chromatography on silica gel with CH$_2$Cl$_2$/EtOAc (10:1) afforded white solid (602 mg, 85%).

Preparative Example 10

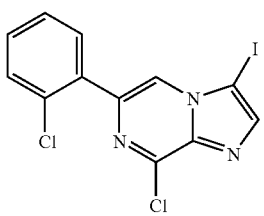

This compound was prepared by essentially same procedure set forth in Preparative Example 9. White solid; LCMS; MH$^+$=390.

Preparative Example 11

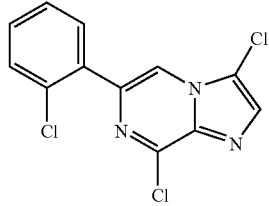

This compound was prepared by essentially same procedure set forth in Preparative Example 9. White solid.

Example 11

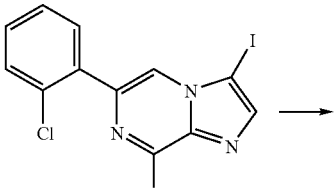

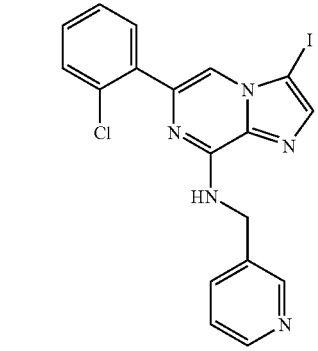

A mixture of the product from Preparative Example 10 (78 mg, 0.20 mmol), 3-(aminomethyl)pyridine (24 mg, 0.22 mmol), diisopropylethylamine (0.5 mL), and anhydrous dioxane (1.0 mL) was stirred at 90° C. under N$_2$ for 48 hr. The solvent was evaporated and the residue was purified by column chromatography on silica gel with CH$_2$Cl$_2$/MeOH/conc. aqueous NH$_4$OH (50:1:0.1). White solid (67 mg, 78%) was obtained. LCMS; MH$^+$=462, m.p. 173-175° C.

Examples 11.1 and 11.2

By essentially the same procedure given in Preparative Example 11, compounds given in Column 2 of Table 5.1 can be prepared from compounds given in Column 1.

TABLE 5.1

| Example | Column 1 | Column 2 |
|---------|----------|----------|
| 11.1 | | |
| 11.2 | | |

Example 12-25

By essentially same procedure set forth in Example 11, the compounds shown in column 3 of Table 2 were prepared.

TABLE 2

| Example | Column 2 | Column 3 | DATA |
|---------|----------|----------|------|
| 12 | | | LCMS: (M + 2H)+ = 382, M.P. > 205° C. |

TABLE 2-continued
| Example | Column 2 | Column 3 | DATA |
|---|---|---|---|
| 13 | 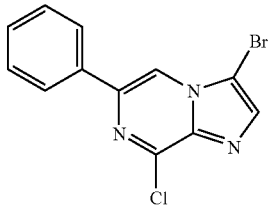 | 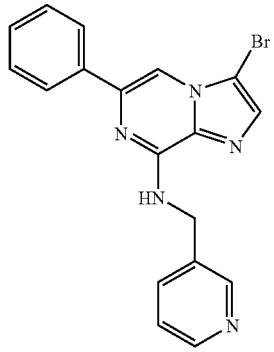 | LCMS: (M + 2H)+ = 382, M.P: 185-188° C. |
| 14 | 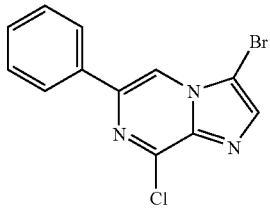 | 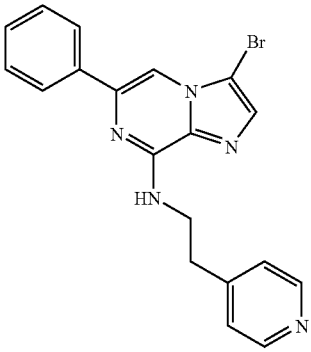 | LCMS: MH+ = 394, M.P: 177-179° C. |
| 15 | 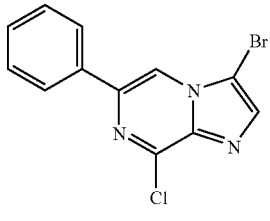 | 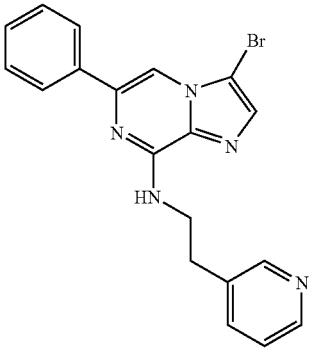 | LCMS: MH+ = 394, M.P: 120-122° C. |
| 16 | 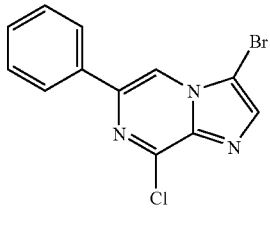 | 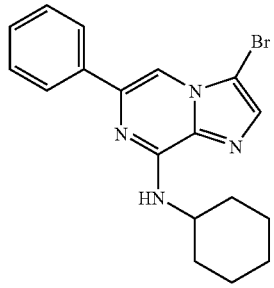 | LCMS: MH+ = 371, M.P: 145-146° C. |

TABLE 2-continued

| Example | Column 2 | Column 3 | DATA |
|---------|----------|----------|------|
| 17 | | | LCMS: MH+ = 449, M.P: 177-179° C. |
| 18 | | | LCMS: MH+ = 428, M.P: 204-206° C. |
| 19 | | | LCMS: MH+ = 428, M.P: 139-141° C. |
| 20 | | | LCMS: MH+ = 415, M.P: 150-152° C. |

TABLE 2-continued

| Example | Column 2 | Column 3 | DATA |
|---|---|---|---|
| 21 | | | LCMS: MH+ = 415, M.P: 146-147° C. |
| 22 | | | LCMS: MH+ = 479, M.P: 78-80° C. |
| 23 | | | LCMS: MH+ = 578, M.P: 175-177° C. |
| 24 | | | LCMS: MH+ = 462, M.P: 162-164° C. |

TABLE 2-continued

| Example | Column 2 | Column 3 | DATA |
|---|---|---|---|
| 25 | | | LCMS: MH+ = 370, M.P: 127-129° C. |

Examples 25.1 and 25.2

Compounds given in Column 2 of Table 6.1 are prepared from compounds given in Column 1 by acidic hydrolysis (HCl in H$_2$O), followed by neutralization (K$_2$CO$_3$) and column chromatography.

TABLE 6.1

| Example | Column 1 | Column 2 |
|---|---|---|
| 25.1 | | |
| 25.2 | | |

Example 26

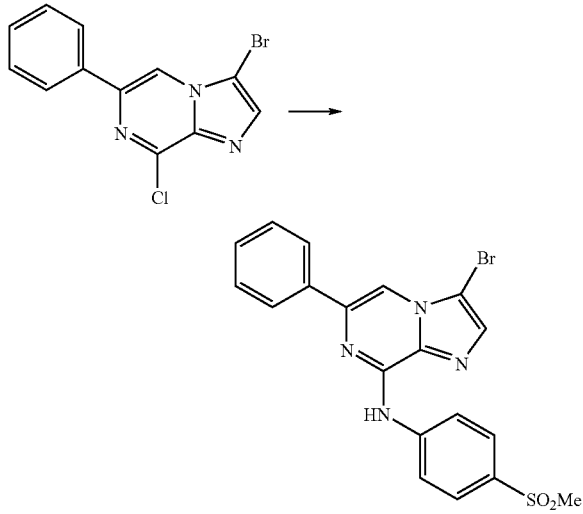

A mixture of the product from Preparative Example 7 (81 mg, 0.20 mmol) and 4-methylsulfonylaniline hydrochloride (55 mg, 0.32 mmol) in diisopropylethylamine (1.5 mL) was stirred at 110° C. for 3 days. The solvent was evaporated and the residue was purified by column chromatography on silica gel with $CH_2Cl_2$/MeOH/conc. aqueous $NH_4OH$ (20:1:0.1). White solid (22 mg, 20%) was obtained. M. P. 251-254° C., LCMS: $(M+2H)^+=445$.

Example 27

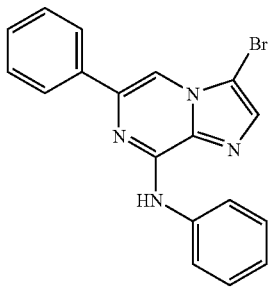

This compound was prepared by essentially same procedure set forth in Example above. M. P. 169-170° C., LCMS: $(M+2H)^+=367$.

Preparative Example 28

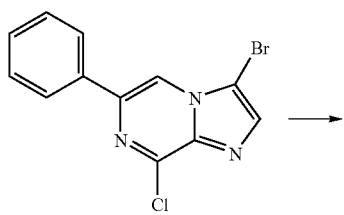

-continued

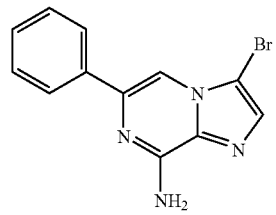

Product from Preparative Example 7 (185 mg, 0.60 mmol) was stirred with conc. Aqueous $NH_4OH$ (3 mL) and 2 M $NH_3$ in 2-propanol (6 mL) in a closed pressure tube at 90° C. for 24 hr. The solvent was evaporated and the residue was purified by column chromatography on silica gel with $CH_2Cl_2$/MeOH/conc. Aqueous $NH_4OH$ (20:1:0.1). Slightly yellow solid (138 mg, 80%) was obtained. M. P. 215-217° C., LCMS: $MH^+=291$.

Preparative Example 29

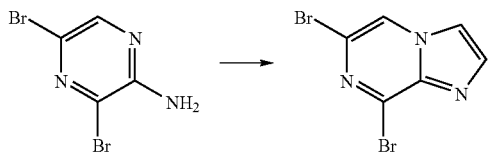

A mixture of 2-amino-3,5-dibromopyrazine (Aldrich, 6.0 g, 24.0 mmol) and 50% aqueous solution of chloroacetaldehyde (Aldrich, 4.8 mL) in 2-propanol (30 mL) was stirred and refluxed under $N_2$ for 24 hr. $CH_2Cl_2$ (300 mL) and triethylamine (12 mL) were added and the solvent was evaporated. The residue was suspended in 10:1 $H_2O$:2-propanol (200 mL), filtered, and the solid was washed on filter with 10:1 $H_2O$:2-propanol (2×100 mL). It was dried in a vacuum to yield pale beige solid (4.81 g, 74%).

Preparative Example 30

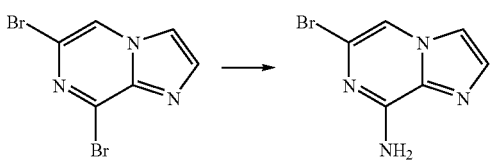

A mixture of the product from Preparative Example 29 (1.80 g, 6.45 mmol) and concentrated aqueous $NH_4OH$ (27.0 mL) was stirred in a closed pressure vessel at 90° C. for 24 hr. The solvent was evaporated and the residue was purified by column chromatography on silica gel with EtOAc. White solid (1.01 g, 73%) was obtained. LCMS: $MH^+=213$.

Preparative Example 31

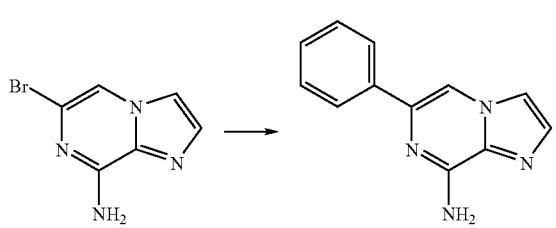

A mixture of the product from Preparative Example 30 (500 mg, 2.36 mmol), phenyl boronic acid (431 mg, 3.53 mmol), Pd(PPh$_3$)$_4$ (277 mg, 0.24 mmol), and Na$_2$CO$_3$ (2.50 g, 23.6 mmol) in 1,2-dimethoxyethane (30 mL) and H$_2$O (8 mL) was stirred and refluxed under N$_2$ for 24 hr. The mixture was poured into H$_2$O (500 mL), extracted with CH$_2$Cl$_2$ (4×50 mL) and the extracts were dried over Na$_2$SO$_4$ and filtered. The solvent was evaporated and the residue was purified by column chromatography on silica gel with PhCH$_3$/7N NH$_3$ in MeOH (10:1). This afforded a slightly impure product as a pale orange solid, which was used for the next step.

Preparative Example 32

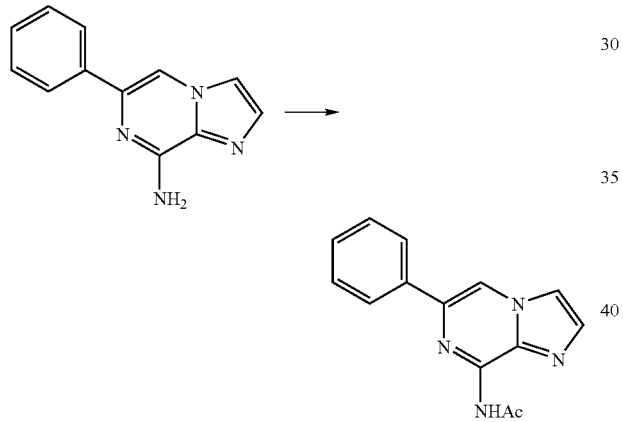

A mixture of the product from Preparative Example 31 (210 mg, 1.0 mmol), acetyl chloride (0.286 mL, 4.0 mmol), and pyridine (0.657 mL, 8.0 mmol) in 1,2-dichloroethane (5 mL) was stirred and refluxed for 72 hr. The mixture was poured into 10% aqueous Na$_2$CO$_3$ and extracted with CH$_2$Cl$_2$ (3×20 mL). The extracts were dried over Na$_2$SO$_4$, filtered and the solvent was evaporated. Chromatography on silica gel with EtOAc as eluent afforded 141 mg (56%) of pale yellow solid.

Preparative Example 33

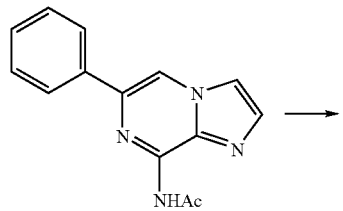

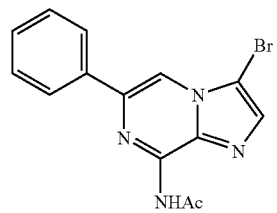

A solution of NBS (72 mg, 0.40 mmol) in anhydrous CH$_3$CN (2.0 mL) was added under N$_2$ to a stirred solution of the product from Preparative Example 32 (100mg, 0.40 mmol) in anhydrous CH$_3$CN (2.0 mL) and CH$_2$Cl$_2$ (6.0 mL). The mixture was stirred at 25° C. for 48 hr and the solvent was then evaporated. Chromatography on silica gel with CH$_2$Cl$_2$/EtOAc (4:1) afforded pale yellow solid (41 mg, 31%). M. P. 163-165° C., LCMS: (M+2H)$^+$=333.

Example 34

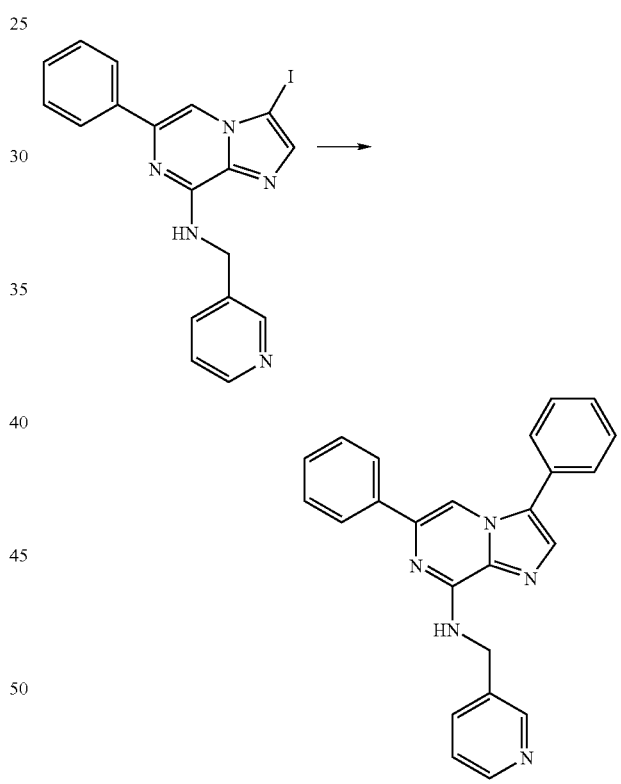

A mixture of the product from Example 17 (85 mg, 0.20 mmol), phenyl boronic acid (37 mg, 0.30 mmol), Pd(PPh$_3$)$_4$ (23 mg, 0.02 mmol), and Na$_2$CO$_3$ (212 g, 2.00 mmol) in 1,2-dimethoxyethane (3.2 mL) and H$_2$O (0.8 mL) was stirred and refluxed under N$_2$ for 24 hr. The mixture was poured into H$_2$O (100 mL), extracted with CH$_2$Cl$_2$ (4×15 mL) and the extracts were dried over Na$_2$SO$_4$ and filtered. The solvent was evaporated and the residue was purified by column chromatography on silica gel with EtOAc/MeOH (30:1) to afford colorless waxy solid (46 mg, 61%). M. P. 138-140° C., LCMS: (M+2H)$^+$=378.

Examples 35 and 36

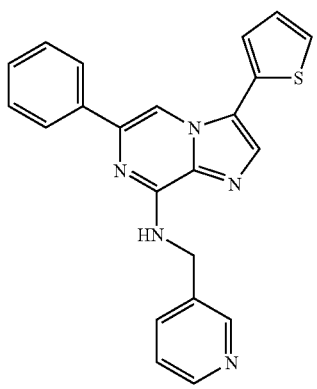

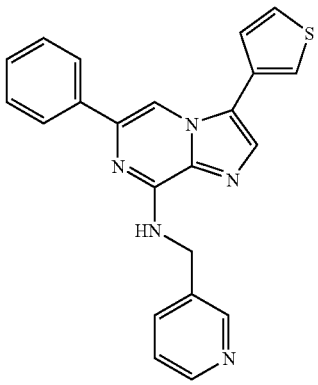

These compounds were prepared by essentially same procedure set forth in Example 34 above. Compound 35: M. P. 168-169° C., LCMS: MH⁺=384; Compound 36: M. P. 154-156° C., LCMS: MH⁺=384.

Example 37

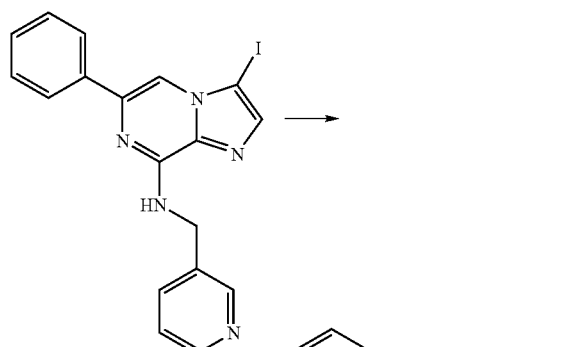

A mixture of the product from Example 17 (214 mg, 0.50 mmol), tributyl(vinyl)tin (174 mg, 0.55 mmol), and Pd(PPh$_3$)$_4$ (58 mg, 0.05 mmol), in 1,4-dioxane (10 mL) was stirred and refluxed under N$_2$ for 24 hr. The solvent was evaporated and the residue was purified by column chromatography on silica gel with CH$_2$Cl$_2$/MeOH/conc. Aqueous NH$_4$OH (40:1:0.1). Pale yellow solid (123 mg, 75%) was obtained. M. P. 138-141° C., LCMS: MH⁺=328.

Example 38

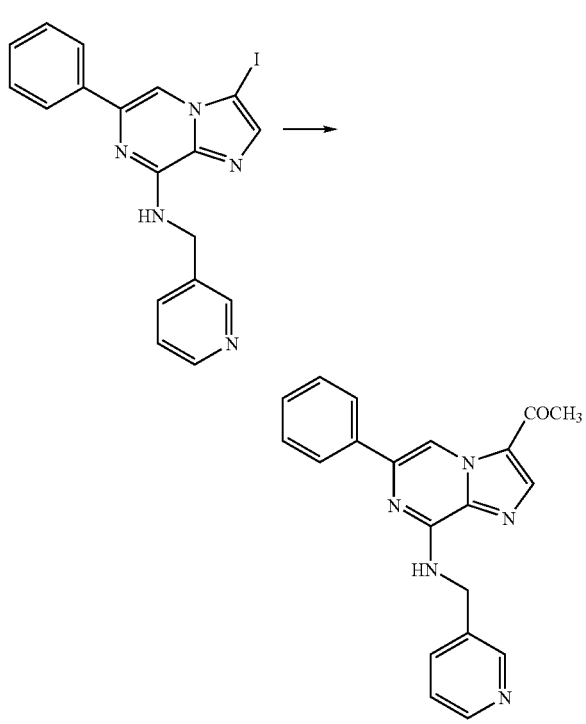

A mixture of the product from Example 17 (214 mg, 0.50 mmol), tributyl(ethoxyvinyl)tin (199 mg, 0.55 mmol), and Pd(PPh$_3$)$_4$ (58 mg, 0.05 mmol), in 1,4-dioxane (10 mL) was stirred and refluxed under N$_2$ for 24 hr. 5 M HCl (1.0 mL) was added, the mixture was stirred for 5 min, then triethylamine (5 mL) was added and the solvent was evaporated. The residue was purified by column chromatography on silica gel with EtOAc/MeOH (10:1) and then triturated with cyclohexane (10 mL). Pale yellow solid (104 mg, 65%) was obtained. M. P.192-194° C., LCMS: MH⁺=344.

Example 39

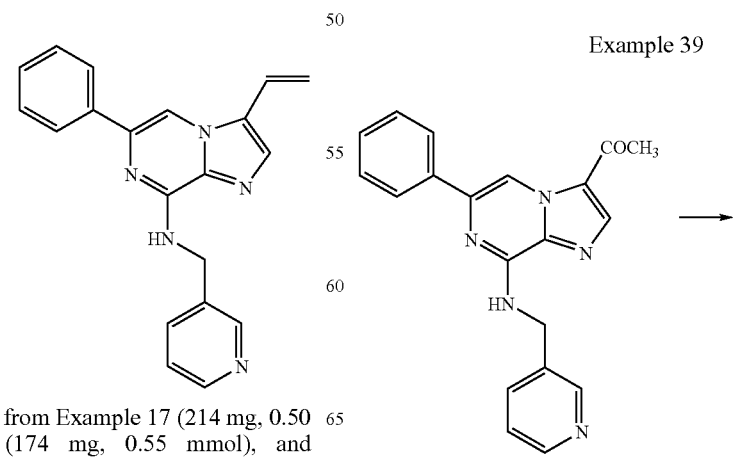

-continued

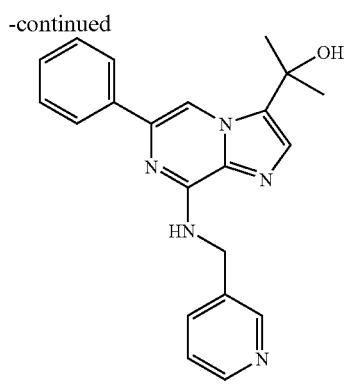

MeMgI (3.0 M in Et₂O, 0.20 mL, 0.60 mmol) was added to a stirred solution of the product from Example 38 (51 mg, 0.15 mmol) in anhydrous Et₂O (3 mL) and CH₂Cl₂ (6 mL). The mixture was stirred at 25° C. for 3 hr and then poured into H₂O (100 mL) and extracted with CH₂Cl₂ (3×20 mL). The extracts were dried over Na₂SO₄, filtered and the solvent was evaporated. The residue was purified by column chromatography on silica gel with CH₂Cl₂/MeOH (20:1) to afford pale yellow solid (27 mg, 50%). M. P. 184-185° C., LCMS: MH⁺=360.

Preparative Example 40

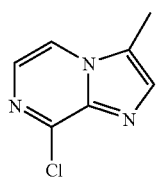

This compound was made according to the literature procedure (*J. Med. Chem.* 1983, 26, 357. and *J. Med. Chem.* 1992, 35, 3845.).

Example 41

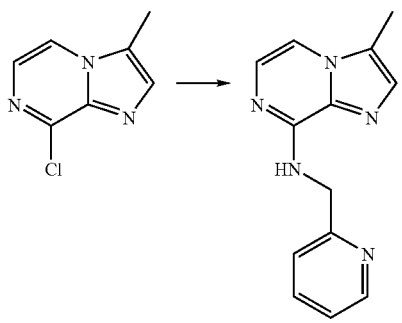

A mixture of the product from Preparative Example 40 (50 mg, 0.30 mmol), 2-(aminomethyl)pyridine (45 mg, 0.42 mmol), and diisopropylethylamine (0.20 mL) in anhydrous 1,4-dioxane (0.50 mL) was stirred under N₂ at 100° C. for 24 hr. The solvent was evaporated and the residue was purified by column chromatography on silica gel with CH₂Cl₂/MeOH/conc. aqueous NH₄OH (2:1:0.1). White solid (45 mg, 63%) was obtained. M. P. 125-127° C., LCMS: MH⁺=240.

Examples 42-48

By essentially same procedure set forth in Preparative Example 41, compounds given in column 3 of Table 3 were prepared.

TABLE 3

| Example | Column 2 | Column 3 | DATA |
|---|---|---|---|
| 42 | | | M.P. 152-154° C., LCMS: MH⁺ = 239. |
| 43 | | | M.P. 130-132° C., LCMS: MH⁺ = 254. |
| 44 | | | M.P. 104-105° C., LCMS: MH⁺ = 207. |
| 45 | | | M.P. 182-184° C., LCMS: MH⁺ = 225. |

TABLE 3-continued

| Example | Column 2 | Column 3 | DATA |
|---|---|---|---|
| 46 | | | M.P. 183-185° C., LCMS: MH+ = 240. |
| 47 | | | M.P. 186-188° C., LCMS: MH+ = 315. |
| 48 | | | M.P. 143-145° C., LCMS: MH+ = 240. |

Example 49

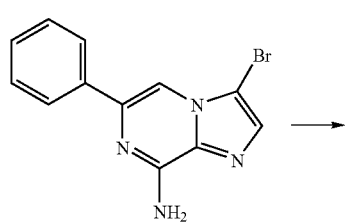

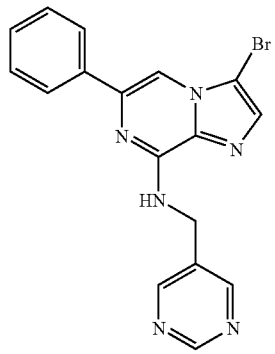

A mixture of the product from Preparative Example 28 (1.16 g, 4.00 mmol), pyrimidine-5-carboxaldehyde (540 mg, 5.00 mmol), and Ti(OiPr)$_4$ (4.54 g, 16.0 mmol) in anhydrous THF (20 mL) was stirred under N$_2$ at 50° C. for 3 hr. The mixture was cooled to 25° C., NaBH$_3$CN (1.26 g, 20.0 mmol) was added, and the mixture was stirred at 25° C. for 30 min. The mixture was poured into 5% aqueous NaOH (500 mL), saturated aqueous NaCl (50 mL) was added, and the mixture was extracted with CH$_2$Cl$_2$ (3×100 mL). The combined extracts were dried over Na$_2$SO$_4$, filtered, and the solvent was evaporated. The residue was purified by column chromatography on silica gel with CH$_2$Cl$_2$/MeOH/conc. aqueous NH$_4$OH (20:1:0.1). Pale yellow solid (410 mg, 27%) was obtained. M. P. 201-203° C., LCMS: MH+=383.

Example 50

A stock solution of the title compound from Preparative Example 8 (1.2 g) in anhydrous CH$_3$CN (120 mL) was prepared and an aliquot (1 mL, 10 mg, 0.0291 mmoles) was placed in each of the wells of an X-Block containing PS-DMAP resin (77.6mg, 0.1 164 mmoles). Freshly prepared 1M solutions of a library of 96 primary amines (0.0873 mL, 0.0873 mmoles) were added to each of the 96 wells of the X-Block. The unit was sealed and heated at 60-70° C. for 26 h. The block was cooled, opened and filtered into a new X-Block containing PS-Isocyanate resin (35 mg, 0.073 mmoles) and PS-Trisamine resin (35 mg, 0.15 mmoles) and the PS-DMAP resin was washed with CH$_3$CN (0.5 mL/well). The X-Block was sealed and shaken at 25° C. for 71 h. The block was opened, filtered and each well was washed with CH$_3$CN (0.5 mL). The wells were evaporated to dryness on a Speedvac concentrator. The samples were analyzed by LCMS and samples that were <90% pure were further purified as needed by preparative LCMS. The samples were each dissolved in 60% DMSO-CH$_3$CN (1 mL) and 0.8 mL of each were injected onto the preparative HPLC (using a Phenomenex Luna 5n C-18(2) column; 60×21.2 mm; 5n micron: flow rate of 20 mL/min; gradient elution using water-CH$_3$CN-1% aqueous formic acid) and the fractions corresponding to the desired molecular weight of the product ±1 mu were collected. The final products that were all >90% pure are listed in the Table 4.

TABLE 4
| STRUCTURE | MW | LCMS m/z | % PURITY |
|---|---|---|---|
| 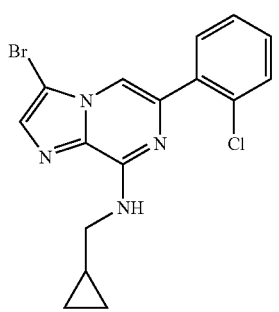 | 377.7 | 379.2 | 97 |
| 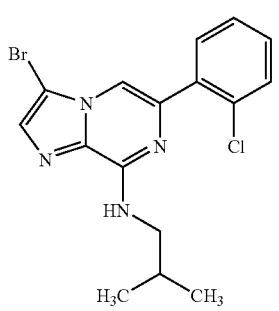 | 379.7 | 381.2 | 90 |
| 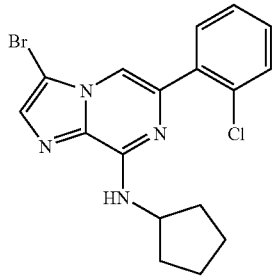 | 391.7 | 393.2 | 93 |
| 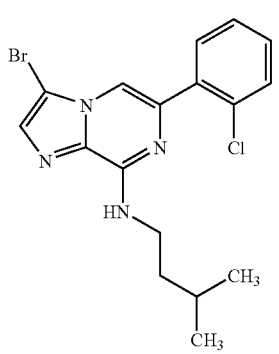 | 393.7 | 395.2 | 99 |
TABLE 4-continued
| STRUCTURE | MW | LCMS m/z | % PURITY |
|---|---|---|---|
| 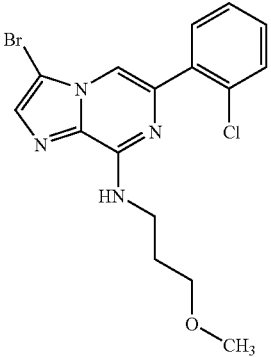 | 395.7 | 397.1 | 98 |
| 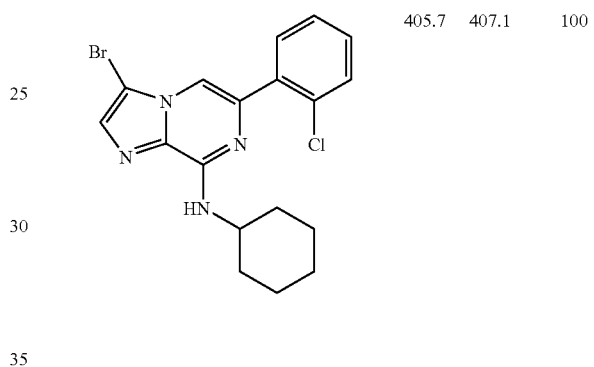 | 405.7 | 407.1 | 100 |
| 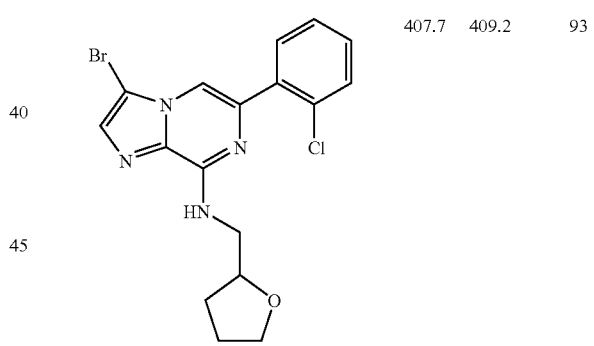 | 407.7 | 409.2 | 93 |
| 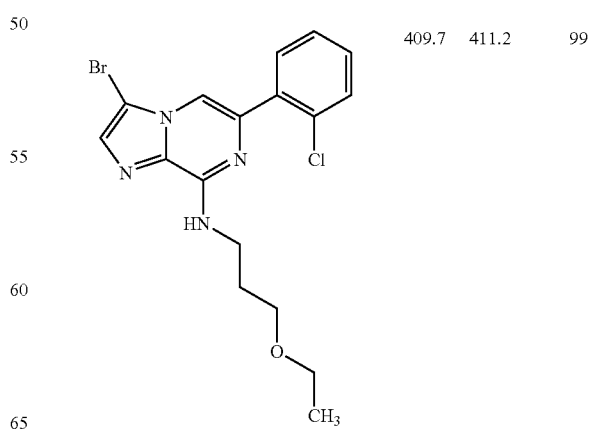 | 409.7 | 411.2 | 99 |

TABLE 4-continued

| STRUCTURE | MW | LCMS m/z | % PURITY |
|---|---|---|---|
| (3-bromo-6-(2-chlorophenyl)-N-(thiophen-2-ylmethyl)imidazo[1,2-a]pyrazin-8-amine) | 419.7 | 421.1 | 100 |
| (3-bromo-6-(2-chlorophenyl)-N-(cyclohexylmethyl)imidazo[1,2-a]pyrazin-8-amine) | 419.8 | 421.2 | 94 |
| (3-bromo-6-(2-chlorophenyl)-N-(3-isopropoxypropyl)imidazo[1,2-a]pyrazin-8-amine) | 423.7 | 425.2 | 100 |
| (3-bromo-6-(2-chlorophenyl)-N-(1-phenylethyl)imidazo[1,2-a]pyrazin-8-amine) | 427.7 | 429.2 | 99 |
| (3-bromo-6-(2-chlorophenyl)-N-phenethylimidazo[1,2-a]pyrazin-8-amine) | 427.7 | 429.2 | 91 |
| (3-bromo-N-(3-butoxypropyl)-6-(2-chlorophenyl)imidazo[1,2-a]pyrazin-8-amine) | 437.8 | 439.2 | 95 |
| (3-bromo-6-(2-chlorophenyl)-N-(2-phenylpropyl)imidazo[1,2-a]pyrazin-8-amine) | 441.8 | 443.2 | 90 |

TABLE 4-continued
| STRUCTURE | MW | LCMS m/z | % PURITY |
|---|---|---|---|
| 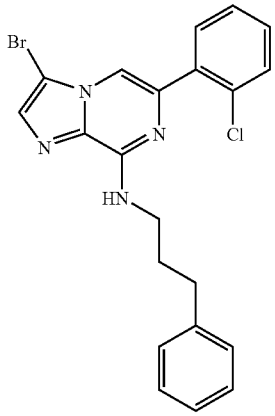 | 441.8 | 443.2 | 94 |
| 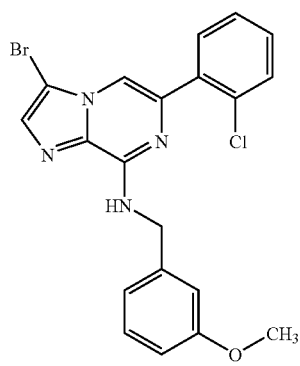 | 443.7 | 445.1 | 100 |
| 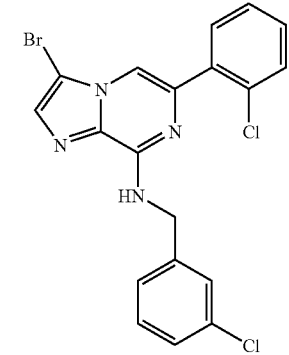 | 448.2 | 449.1 | 91 |
| 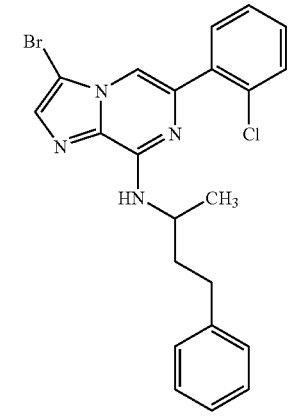 | 455.8 | 457.3 | 99 |
TABLE 4-continued
| STRUCTURE | MW | LCMS m/z | % PURITY |
|---|---|---|---|
| 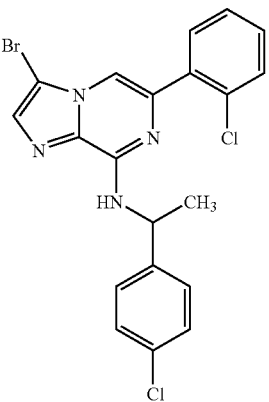 | 462.2 | 463.1 | 99 |
| 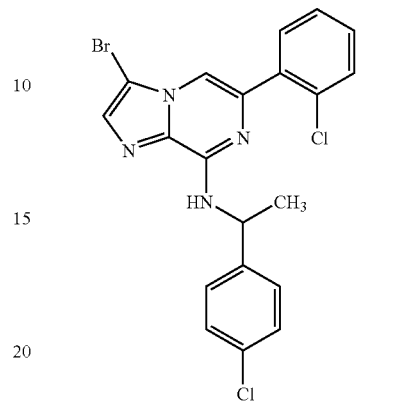 | 478.8 | 480.1 | 100 |
| 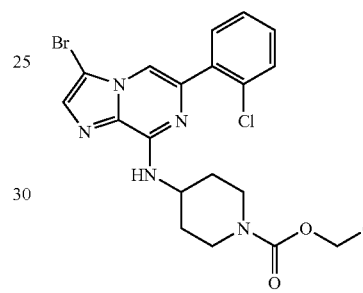 | 481.7 | 483.3 | 97 |
| 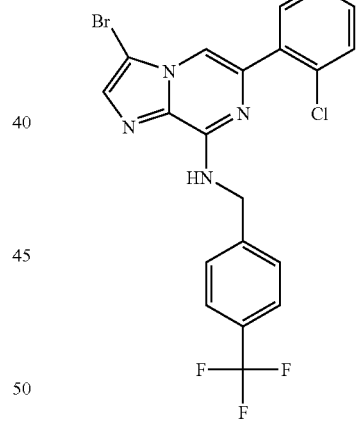 | 503.8 | 505.1 | 94 |
| 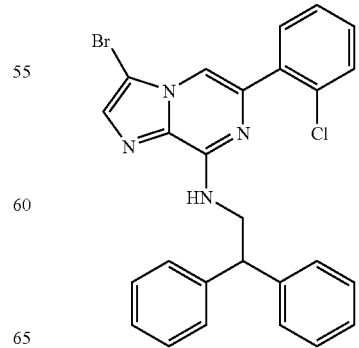 | | | |

TABLE 4-continued

| STRUCTURE | MW | LCMS m/z | % PURITY |
|---|---|---|---|
| (structure) | 517.9 | 519.1 | 100 |
| (structure) | 445.8 | 447.2 | 98 |
| (structure) | 381.7 | 383.1 | 99 |
| (structure) | 394.7 | 396.2 | 98 |

TABLE 4-continued

| STRUCTURE | MW | LCMS m/z | % PURITY |
|---|---|---|---|
| (structure) | 395.7 | 397.1 | 92 |
| (structure) | 408.7 | 410.2 | 98 |
| (structure) | 409.7 | 411.1 | 100 |
| (structure) Chiral | 409.7 | 411.2 | 96 |

TABLE 4-continued
| STRUCTURE | MW | LCMS m/z | % PURITY |
|---|---|---|---|
| 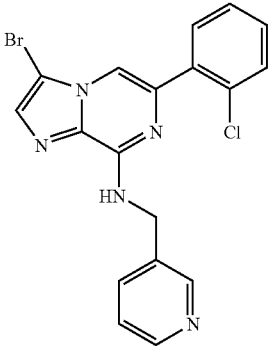 | 414.7 | 416.1 | 97 |
| 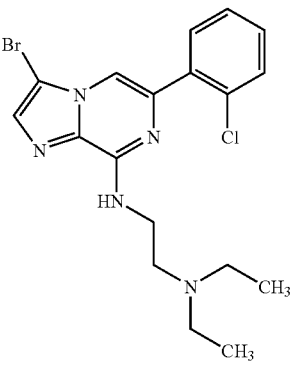 | 422.8 | 424.2 | 98 |
| 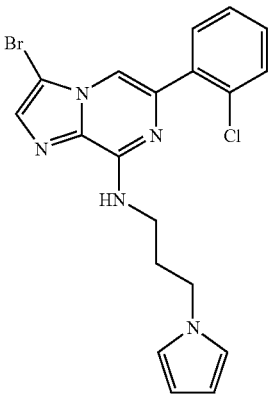 | 430.7 | 432.2 | 94 |
| 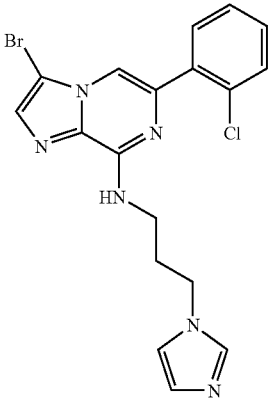 | 431.7 | 433.2 | 94 |
TABLE 4-continued
| STRUCTURE | MW | LCMS m/z | % PURITY |
|---|---|---|---|
| 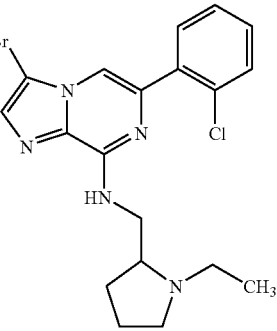 | 434.8 | 436.1 | 100 |
| 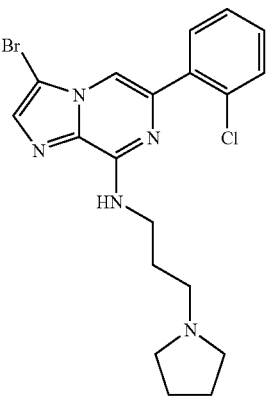 | 434.8 | 436.1 | 100 |
| 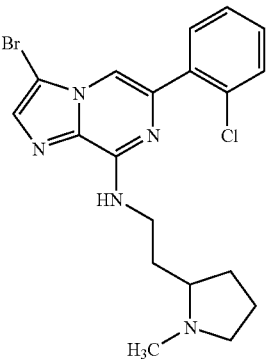 | 434.8 | 436.2 | 95 |
| 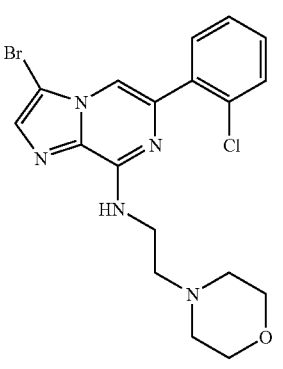 | 436.7 | 438.1 | 100 |

TABLE 4-continued

| STRUCTURE | MW | LCMS m/z | % PURITY |
|---|---|---|---|
| (3-bromo-6-(2-chlorophenyl)imidazo[1,2-a]pyrazin-8-yl)-NH-CH₂CH₂CH₂-N(CH₂CH₃)₂ | 436.8 | 438.2 | 98 |
| (3-bromo-6-(2-chlorophenyl)imidazo[1,2-a]pyrazin-8-yl)-NH-CH₂-C(CH₃)₂-CH₂-N(CH₃)₂ | 436.8 | 438.2 | 98 |
| (3-bromo-6-(2-chlorophenyl)imidazo[1,2-a]pyrazin-8-yl)-NH-CH₂CH₂CH₂-(2-oxopyrrolidin-1-yl) | 448.8 | 450.2 | 95 |
| (3-bromo-6-(2-chlorophenyl)imidazo[1,2-a]pyrazin-8-yl)-NH-CH₂CH₂CH₂-morpholine | 450.8 | 452.2 | 95 |
| (3-bromo-6-(2-chlorophenyl)imidazo[1,2-a]pyrazin-8-yl)-NH-CH₂CH₂CH₂-(2-methylpiperidin-1-yl) | 462.8 | 464.3 | 99 |
| (3-bromo-6-(2-chlorophenyl)imidazo[1,2-a]pyrazin-8-yl)-NH-CH₂CH₂CH₂-(4-methylpiperazin-1-yl) | 463.8 | 465.3 | 92 |
| (3-bromo-6-(2-chlorophenyl)imidazo[1,2-a]pyrazin-8-yl)-NH-(1-benzylpiperidin-4-yl) | 496.8 | 498.1 | 99 |

Preparative Example 51

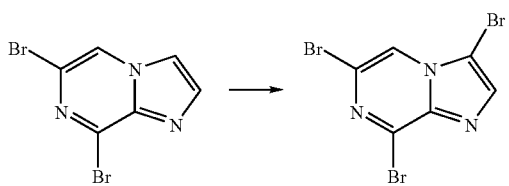

A solution of NBS (1 eq.) in anhydrous CH₃CN (2.0 mL) is added under N₂ to a stirred solution of the product from Preparative Example 29 in anhydrous CH₃CN and CH₂Cl₂. The mixture is stirred at 25° C. for 48 hr and the solvent is then evaporated. Chromatography on silica gel with CH₂Cl₂/EtOAc affords the product.

Example 52

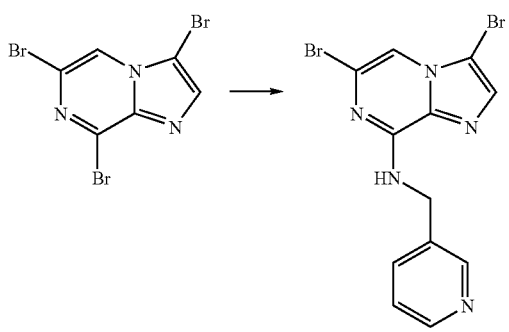

A mixture of the product from Preparative Example 51, 3-(aminomethyl) pyridine (1.1 eq), diisopropylethylamine (3.0 eq), and anhydrous dioxane is stirred at 90° C. under N₂ for 48 hr. The solvent is evaporated and the residue is purified by column chromatography on silica gel with CH₂Cl₂/MeOH/conc. aqueous NH₄OH to yield the product.

Example 53

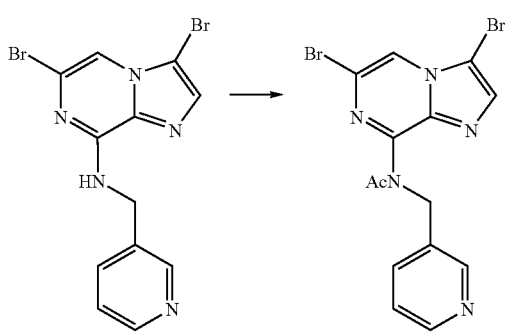

A mixture of the product from Example 52, acetyl chloride (4.0 eq.), and pyridine (8.0 eq.) in 1,2-dichloroethane is stirred and refluxed for 72 hr. The mixture is poured into 10% aqueous Na₂CO₃ and extracted with CH₂Cl₂. The extracts are dried over Na₂SO₄, filtered and the solvent is evaporated. Chromatography on silica gel with EtOAc as eluent affords the product.

Example 54

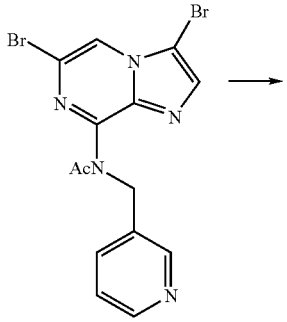

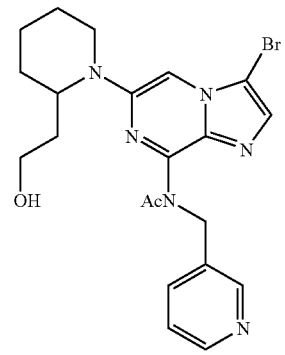

A mixture of the product from Example 53, the aminolacohol (1.5 eq.), and triethylamine (2.0 eq.) in dioxane is stirred and refluxed for 72 hr. The mixture is poured into 10% aqueous Na₂CO₃ and extracted with . The extracts are dried over Na₂SO₄, filtered and the solvent is evaporated. Chromatography on silica gel with CH₂Cl₂:MeOH as eluent affords the product.

TABLE 5

By essentially the same procedure given in Example 54, combining intermediates from Preparative Example 53 with the amines given in column 1, compounds given in column 2 can be prepared.

| Example | Column 1 | Column 2 |
|---|---|---|
| 55 | (2-aminocyclohexanol) | (product structure) |

131

TABLE 5-continued

By essentially the same procedure given in Example 54, combining intermediates from Preparative Example 53 with the amines given in column 1, compounds given in column 2 can be prepared.

| Example | Column 1 | Column 2 |
|---|---|---|
| 56 | cyclohexyl-CH2OH with NH2 | cyclohexyl-CH2OH-NH-[3-bromo-imidazopyrazine with AcN-CH2-pyridyl] |
| 57 | isopropyl-CH(NH2)-CH2OH | isopropyl-CH(NH-[3-bromo-imidazopyrazine with AcN-CH2-pyridyl])-CH2OH |

132

Example 58

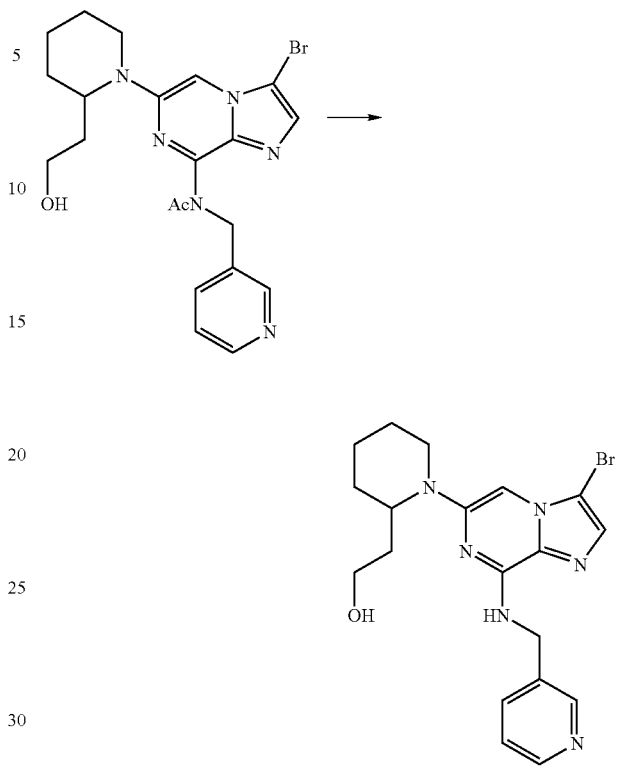

A mixture of the product from Example 54, and $K_2CO_3$ (2.0 eq.) in 1:1 EtOH:$H_2O$ is stirred at 60° C. for 2 hr. The mixture is poured into $H_2O$ and extracted with $CH_2Cl_2$. The extracts are dried over $Na_2SO_4$, filtered and the solvent is evaporated. Chromatography on silica gel with $CH_2Cl_2$:MeOH:conc.$NH_4OH$ affords the product.

TABLE 6

By essentially the same procedure given in Example 58, starting form compounds given in Column 1, compounds given in column 2 can be prepared.

| Example | Column 1 | Column 2 |
|---|---|---|
| 59 | cyclohexyl(OH)-NH-[3-bromo-imidazopyrazine with AcN-CH2-pyridyl] | cyclohexyl(OH)-NH-[3-bromo-imidazopyrazine with HN-CH2-pyridyl] |

TABLE 6-continued

By essentially the same procedure given in Example 58, starting form compounds given in Column 1, compounds given in column 2 can be prepared.

| Example | Column 1 | Column 2 |
|---|---|---|
| 60 | 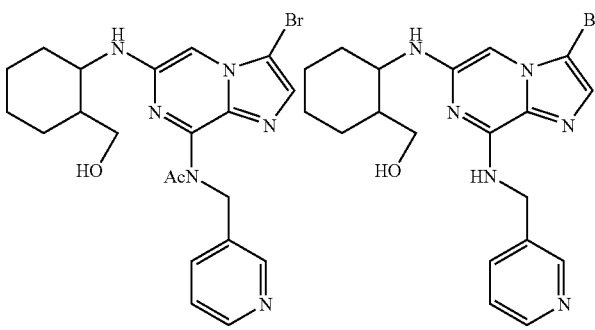 | 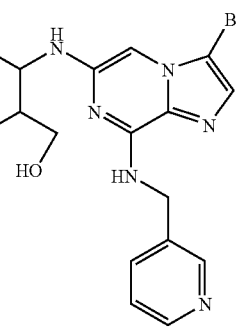 |
| 61 | 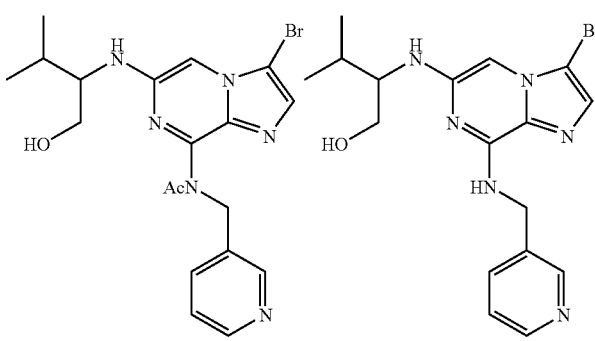 | 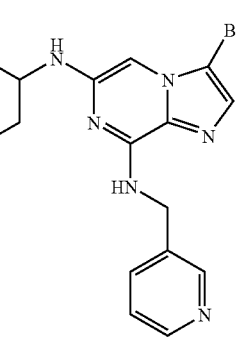 |

The compounds in Table 1B and Table 1C were prepared as follows:

Example 100

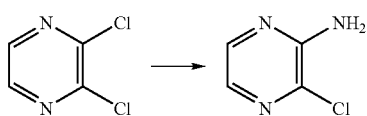

A mixture 2, 3-dichloropyrazine (50 g, 0.34 mmol) and concentrated aqueous ammonium hydroxide (200 mL) was stirred at 85° C. in a closed pressure vessel for 4 days. The mixture was cooled to 25° C., water (200 mL) was added, and the mixture was filtered. The solid was washed with water (400 mL), then with dichloromethane (400 mL) and dried under vacuum. Compound 100 was isolated as a white solid 32.5 g (73%). $^1$H NMR (400 MHz, DMSO-d$_6$ δ 7.93 (d, 1H), 7.55 (d, 1H), 6.79 (bs, 2H).

Example 101

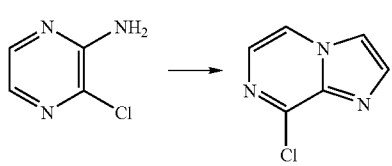

α-Bromo diethyl acetal (51.6 mL, 332.7 mmol, 2.5 eq) was added to a solution of 7.7 mL HBr (conc.) and 80 mL of H$_2$O. The reaction was heated at reflux for 1 h. The reaction was cooled and extracted 2× with Et$_2$O (200 mL). The Et$_2$O extracts were combined, washed with brine, and dried over Na$_2$SO$_4$ before being concentrated. The material was not left on the rotavap for an extended time or put under high vacuum. The oily residue was mixed with DME (200 mL) and the 2-amino-3-chloropyrazine (2,17.240 g, 133.1 mmol) was added. HBr conc. (1-1.5 mL) was added and the reaction was heated at reflux. The heterogeneous reaction mixture becomes homogenous after 10-15 minutes. After approximately 30 minutes a precipitate begins to form. After 1 hour at reflux the black reaction was cooled to room temperature, filtered, and washed with Et$_2$O (4×, 75 mL) to give compound 101 $^1$H NMR (DMSO-d$_6$, 400 MHz) δ 8.70 (d, J=2.0 Hz, 1H), 8.32 (s, 1H), 7.93 (s, 1H), 7.79 (d, J=3.0 Hz, 1H). LC/MS shows a mixture of two products (one product by LC and two by MS). By MS there is a mass for X=Cl (major) MH$^+$=154 (m/z) and one for X=Br (minor) MH$^+$198 (m/z). This mixture gave the product in approximately 90% yield as the HBr salt.

Example 102

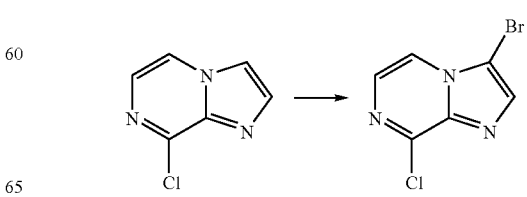

The 7-halo compound 101 (4.92 g, 20.2 mmol) was mixed with Br$_2$ (1.54 mL, 30.0 mmol) in AcOH (100 mL) at room temperature. After 5-10 minutes the reaction became homogeneous. After 1.5 hours a Precipitate began to form. The reaction stirred at room temperature for 3 days. The reaction was concentrated in vacuo. The residue was taken up in 10% iso-PrOH in CH$_2$Cl$_2$ (300 mL) and washed with sat. NaHCO$_3$ (2×, 100 mL), 1M Na$_2$S$_2$O$_3$ (100 mL), and brine (100 mL). The organic layer was dried with Na$_2$SO$_4$ and concentrated in vacuo to give 4.460 g of the product, compound 102 (91% yield). $^1$H NMR (DMSO-d$_6$, 400 MHz) δ 8.47 (d, J=4.8 Hz, 1H), 8.02 (s, 1H), 7.84 (d, J=4.4 Hz, 1H).

Example 103

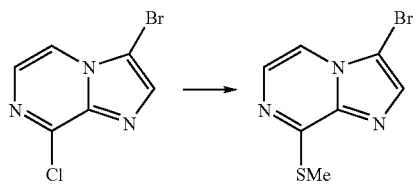

To a solution of compound 102 (13.0 g, 55.9 mmol) in DMSO (150 mL) was added sodium methanethiolate (4.70 g, 67.08 mmol) as a DMSO solution (100 mL) at room temperature. The reaction mixture was stirred at 100° C. for 16 hours. The mixture was cooled to 25° C. and added to a brine solution (300 mL), and extracted with 10% IPA/dichloromethane (300 mL, 3×). The combined organic layer was dried over anhydrous sodium sulfate and concentrated. Purification by column chromatography (SiO$_2$, ethyl acetate/hexanes (1:1)) afforded compound 103 as a yellow solid 10 g (70%). $^1$H-NMR (400 MHz, DMSO-d$_6$ δ 8.15 (d, 1H), 7.88 (d, 1H), 7.83 (s, 1H), 2.6 (s, 3H).

Example 104

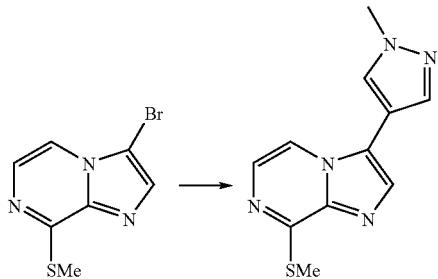

A mixture of compound 103 (5.0 g, 17.8 mmol), 1-methyl-4-(4,4,5,5-teramethyl-1,3,2-dioxaborolan-2-yl)-1H-pyrazole (7.44 g, 35.7 mmol), Pd(dppf)Cl$_2$ (1.46 g, 10 mol %), sodium carbonate (9.50 g, 89.5 mmol) in 1,2-dimethoxyethane (150 mL) and water (37 mL) was stirred at 70° C. under Argon for 16 hours. The solvents were evaporated and the residue was purified by column chromatography (SiO$_2$, ethyl acetate to 5% methanol/ethyl acetate) to afford compound 104 as a beige solid 3.80 g (86%). $^1$H NMR (400 MHz, DMSO-d$_6$ δ 8.35 (s, 1H), 8.27 (d, 1H), 7.96 (d, 1H), 7.82 (s, 1H), 7.81 (d, 1H), 3.93 (s, 3H), 2.59 (s, 3H).

Example 105

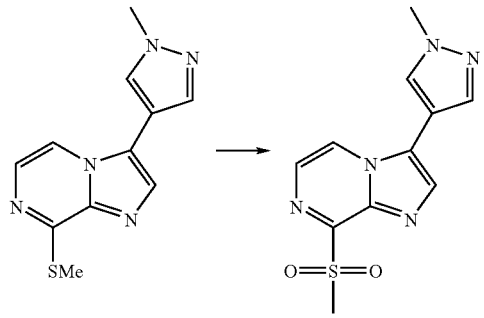

To a solution of compound 104 (3.0 g, 12.2 mmol) in dichloromethane (100 mL) at room temperature was added m-CPBA (5.75 g, 25.6 mmol) in one portion. The mixture was stirred at room temperature for 1 hour at which time thin layer chromatography (10% MeOH/ethyl acetate) indicated that the reaction was complete. The reaction mixture was poured into saturated aqueous sodium bicarbonate (100 mL). The layers were separated and the aqueous layer was extracted with dichloromethane (2×100 mL). The organic layers were combined and washed with brine (150 mL). The organic layer was dried over sodium sulfate, filtered, and concentrated under reduced pressure to yield a dark yellow oil. Purification by column chromatography (SiO$_2$, 10% methanol/ethyl acetate) afforded compound 105 as a yellow solid 2.10 g (62%). $^1$H NMR (400 MHz, DMSO-d$_6$ δ 8.83 (d, 2H), 8.45 (s, 1H), 8.21 (s, 1H), 8.11 (d, 1H), 8.06 (d, 1H), 3.96 (s, 3H), 3.61 (s, 3H). HPLC-MS t$_R$=0.75 min (UV$_{254\,nm}$). Mass calculated for formula C$_{11}$H$_{11}$N$_5$O$_2$S 277.06; observed MH$^+$ (LCMS) 278.1 (m/z).

Example 106

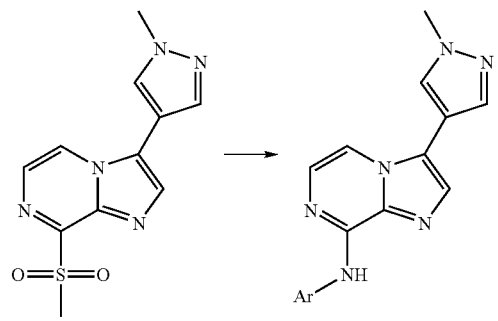

A solution of the respective aromatic amine (2 equivalents) in DMSO (1 mL) was treated with NaH (60% dispersion in oil, 2 equivalents) for 15 minutes at room temperature. Compound 105 (1 equivalent) was then added to this solution at room temperature and this solution was stirred at room temperature for 1 hour at which time thin layer chromatography (10% methanol/ethyl acetate) indicate the reaction was complete. The reaction mixture was diluted with sat. ammonium chloride (0.5 mL) and acetonitrile (0.5 mL). Purification by Prep-LC and conversion to a hydrochloric salt afforded compound 106.

Examples 106-1-106-83

By essentially the same procedure given in Preparative Example 106, compounds given in Column 2 of Table 8 can be prepared from compound 105.

TABLE 8

| Example | Column 2 | MW | LCMS MH+ m/z | HPLC MS $t_R$ |
|---|---|---|---|---|
| 106-1 | | 368.4 | 369.1 | 2.73 |
| 106-2 | | 290.3 | 291.1 | 2.47 |
| 106-3 | | 320.3 | 321.1 | 2.34 |
| 106-4 | | 382.4 | 383.1 | 3.84 |

TABLE 8-continued

| Example | Column 2 | MW | LCMS MH+ m/z | HPLC MS $t_R$ |
|---|---|---|---|---|
| 106-5 | | 382.4 | 383.1 | 4.24 |
| 106-6 | | 368.4 | 369.1 | 2.91 |
| 106-7 | | 329.3 | 330.1 | 2.44 |
| 106-8 | | 341.3 | 342.1 | 2.45 |

TABLE 8-continued

| Example | Column 2 | MW | LCMS MH+ m/z | HPLC MS $t_R$ |
|---|---|---|---|---|
| 106-9 | | 297.3 | 298.1 | 2.46 |
| 106-10 | | 355.4 | 356.2 | 2.57 |
| 106-11 | | 340.3 | 341.2 | 3.54 |
| 106-12 | | 342.3 | 343.1 | 2.96 |

TABLE 8-continued

| Example | Column 2 | MW | LCMS MH+ m/z | HPLC MS $t_R$ |
|---------|----------|------|------|------|
| 106-13  |          | 331.3 | 332.2 | 1.93 |
| 106-14  |          | 356.3 | 357.2 | 2.89 |
| 106-15  |          | 291.3 | 292.1 | 2.10 |
| 106-16  |          | 298.3 | 299.2 | 2.45 |

TABLE 8-continued

| Example | Column 2 | MW | LCMS MH+ m/z | HPLC MS $t_R$ |
|---------|----------|------|--------------|---------------|
| 106-17  |          | 292.3 | 293.2 | 2.00 |
| 106-18  |          | 357.3 | 358.1 | 2.98 |
| 106-19  |          | 356.3 | 357.2 | 2.18 |
| 106-20  |          | 324.7 | 325.1 | 3.36 |

TABLE 8-continued

| Example | Column 2 | MW | LCMS MH+ m/z | HPLC MS t$_R$ |
|---|---|---|---|---|
| 106-21 | | 344.3 | 345.2 | 2.35 |
| 106-22 | | 334.3 | 335.2 | 2.40 |
| 106-23 | | 320.3 | 321.2 | 2.35 |
| 106-24 | | 291.3 | 292.1 | 2.20 |

TABLE 8-continued

| Example | Column 2 | MW | LCMS MH+ m/z | HPLC MS $t_R$ |
|---|---|---|---|---|
| 106-25 | | 291.3 | 292.1 | 2.15 |
| 106-26 | | 292.3 | 293.2 | 2.05 |
| 106-27 | | 315.3 | 316.1 | 2.82 |
| 106-28 | | 397.4 | 398.2 | 3.49 |

TABLE 8-continued

| Example | Column 2 | MW | LCMS MH+ m/z | HPLC MS $t_R$ |
|---|---|---|---|---|
| 106-29 | | 430.4 | 431.2 | 4.05 |
| 106-30 | | 402.8 | 403.1 | 3.67 |
| 106-31 | | 357.3 | 358.1 | 1.94 |

TABLE 8-continued

| Example | Column 2 | MW | LCMS MH+ m/z | HPLC MS t_R |
|---|---|---|---|---|
| 106-32 | | 320.3 | 321.2 | 2.70 |
| 106-33 | | 338.3 | 339.1 | 3.24 |
| 106-34 | | 347.4 | 348.1 | 2.34 |
| 106-35 | | 356.3 | 357.2 | 2.96 |

TABLE 8-continued

| Example | Column 2 | MW | LCMS MH+ m/z | HPLC MS t_R |
|---------|----------|------|------|------|
| 106-36  |          | 358.4 | 359.1 | 3.75 |
| 106-37  |          | 373.4 | 374.2 | 4.30 |
| 106-38  |          | 295.3 | 296.2 | 2.05 |
| 106-39  |          | 308.3 | 309.2 | 2.32 |

TABLE 8-continued

| Example | Column 2 | MW | LCMS MH+ m/z | HPLC MS $t_R$ |
|---|---|---|---|---|
| 106-40 | | 341.3 | 342.3 | 2.96 |
| 106-41 | | 295.3 | 296.2 | 3.04 |
| 106-42 | | 311.3 | 312.1 | 2.52 |
| 106-43 | | 294.3 | 295.1 | 2.19 |

TABLE 8-continued

| Example | Column 2 | MW | LCMS MH+ m/z | HPLC MS $t_R$ |
|---------|----------|------|------|------|
| 106-44 | | 341.3 | 342.3 | 2.09 |
| 106-45 | | 347.4 | 348.1 | 2.75 |
| 106-46 | | 341.3 | 342.3 | 3.83 |

TABLE 8-continued

| Example | Column 2 | MW | LCMS MH+ m/z | HPLC MS t_R |
|---|---|---|---|---|
| 106-47 | | 374.5 | 375.2 | 1.78 |
| 106-48 | | 377.4 | 378.3 | 2.07 |
| 106-49 | | 377.4 | 378.3 | 1.81 |

TABLE 8-continued

| Example | Column 2 | MW | LCMS MH+ m/z | HPLC MS t$_R$ |
|---|---|---|---|---|
| 106-50 | | 356.3 | 357.2 | 2.46 |
| 106-51 | | 409.4 | 410.2 | 2.55 |
| 106-52 | | 331.3 | 332.2 | 2.87 |

TABLE 8-continued

| Example | Column 2 | MW | LCMS MH+ m/z | HPLC MS $t_R$ |
|---|---|---|---|---|
| 106-53 | | 346.4 | 347.2 | 3.12 |
| 106-54 | | 344.3 | 345.2 | 2.02 |
| 106-55 | | 357.3 | 358.1 | 2.97 |
| 106-56 | | 375.3 | 376.1 | 3.21 |

TABLE 8-continued

| Example | Column 2 | MW | LCMS MH+ m/z | HPLC MS $t_R$ |
|---|---|---|---|---|
| 106-57 | | 370.4 | 371.2 | 2.71 |
| 106-58 | | 427.4 | 428.2 | 3.50 |
| 106-59 | | 439.4 | 440.2 | 2.33 |

TABLE 8-continued
| Example | Column 2 | MW | LCMS MH+ m/z | HPLC MS $t_R$ |
|---|---|---|---|---|
| 106-60 | 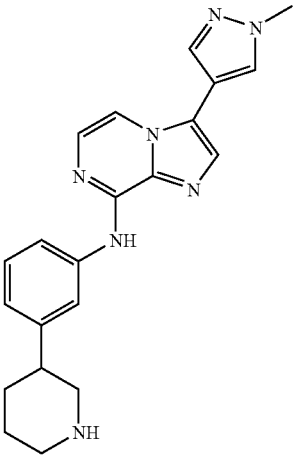 | 373.4 | 374.2 | 2.19 |
| 106-61 | 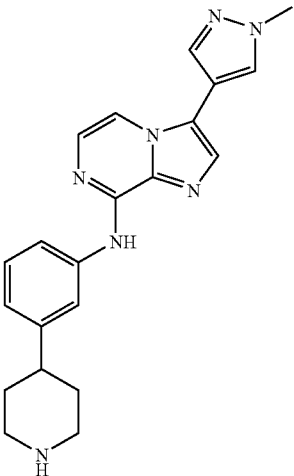 | 373.4 | 374.2 | 2.10 |
| 106-62 | 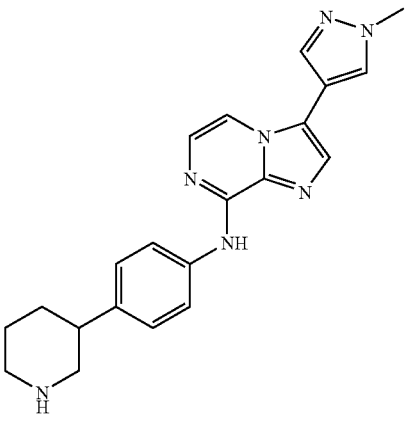 | 373.4 | 374.2 | 2.10 |

TABLE 8-continued

| Example | Column 2 | MW | LCMS MH+ m/z | HPLC MS $t_R$ |
|---|---|---|---|---|
| 106-63 | | 373.4 | 374.2 | 1.99 |
| 106-64 | | 375.4 | 376.1 | 2.21 |
| 106-65 | | 388.4 | 389.2 | 2.51 |
| 106-66 | | 361.4 | 362.1 | 2.51 |

TABLE 8-continued

| Example | Column 2 | MW | LCMS MH+ m/z | HPLC MS $t_R$ |
|---------|----------|------|------|------|
| 106-67  |          | 341.3 | 342.1 | 2.10 |
| 106-68  |          | 341.3 | 342.2 | 2.35 |
| 106-69  |          | 384.4 | 385.1 | 3.49 |

TABLE 8-continued

| Example | Column 2 | MW | LCMS MH+ m/z | HPLC MS t$_R$ |
|---|---|---|---|---|
| 106-69 | | 312.3 | 313.1 | 2.97 |
| 106-70 | | 340.4 | 341.2 | 3.80 |
| 106-71 | | 348.2 | 349.2 | 3.49 |
| 106-72 | | 311.1 | 312.1 | 2.87 |

TABLE 8-continued

| Example | Column 2 | MW | LCMS MH+ m/z | HPLC MS t_R |
|---|---|---|---|---|
| 106-73 | | 403.1 | 404.1 | 5.16 |
| 106-74 | | 297.07 | 298.1 | 2.71 |
| 106-75 | | 296.08 | 297.1 | 3.03 |
| 106-76 | | 310.10 | 311.1 | 3.55 |

TABLE 8-continued

| Example | Column 2 | MW | LCMS MH+ m/z | HPLC MS t$_R$ |
|---|---|---|---|---|
| 106-77 | | 389.00 | 390.0 | 4.41 |
| 106-78 | | 389.5 | 390.3 | 1.80 |
| 106-79 | | 345.17 | 346.2 | 0.85 |
| 106-80 | | 407.44 | 408.4 | 2.15 |

TABLE 8-continued
| Example | Column 2 | MW | LCMS MH+ m/z | HPLC MS $t_R$ |
|---|---|---|---|---|
| 106-81 | | 424.44 | 425.4 | 2.30 |
| 106-82 | | 407.44 | 408.4 | 1.85 |
| 106-83 | | 372.29 | 373.1 | 1.05 |
Example 107
The compounds shown in column 2 of Table 9 were prepared as follows.
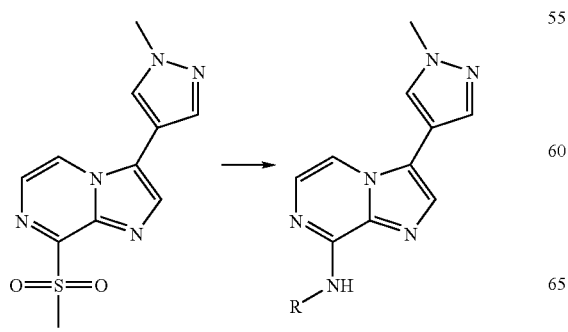

To a solution of compound 105 (1 equivalent) in NMP (0.5 mL) was added DIEA (10 equivalents), and the respective aliphatic amine (2 equivalents) at room temperature. The reaction was heated to 50° C. overnight. LC-MS analysis of the reaction indicates the reaction is complete. The crude reaction mixture was concentrated. Purification by Prep-LC and conversion to a hydrochloric salt afforded compound 107—as a white solid.

TABLE 9

| Example | Column 2 | MW | LCMS MH+ m/z | HPLC MS $t_R$ |
|---|---|---|---|---|
| 107-1 | | 256.3 | 257.3 | 1.60 |
| 107-2 | | 298.3 | 299.3 | 1.90 |
| 107-3 | | 228.2 | 229.2 | 1.49 |
| 107-4 | | 242.3 | 243.2 | 1.81 |
| 107-5 | | 254.3 | 255.1 | 1.82 |
| 107-6 | | 297.4 | 298.2 | 1.41 |
| 107-7 | | 272.3 | 273.2 | 1.85 |
| 107-8 | | 258.3 | 259.2 | 1.47 |

TABLE 9-continued

| Example | Column 2 | MW | LCMS MH+ m/z | HPLC MS $t_R$ |
|---|---|---|---|---|
| 107-9 | | 297.4 | 298.2 | 1.39 |
| 107-10 | | 311.4 | 312.3 | 1.42 |
| 107-11 | | 327.4 | 328.2 | 1.55 |
| 107-12 | | 296.4 | 297.3 | 2.70 |
| 107-13 | | 345.17 | 346.2 | 0.85 |

Example 108

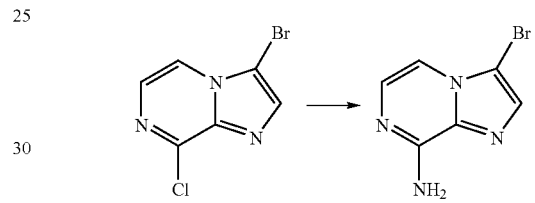

A mixture of compound 102 (2.00 g, 8.6 mmol), conc. aqueous NH$_4$OH (60 mL) and 2-propanol (6 mL) was stirred in a closed pressure vessel at 85° C. for 3 days. The reaction mixture was cooled to 25° C., diluted with water (120 mL) and stirred at 25° C. for 10 minutes. The resulting heterogeneous solution was filtered, the solid was washed with water (3×) and air dried overnight. This gave compound 108 as a beige solid 1.50 g (82%). $^1$H-NMR (400 MHz, DMSO-d$_6$) δ 7.66 (s, 1H), 7.56 (d, 1H), 7.35 (d, 1H), 7.1 (bs, 2H).

Example 109

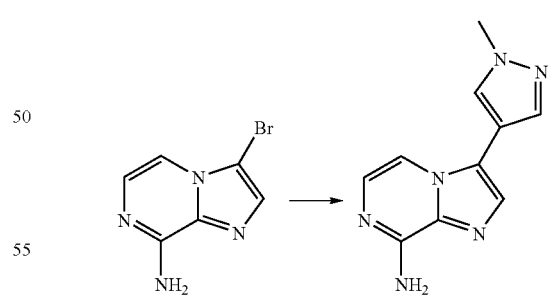

A mixture of compound 108 (1.50 g, 7.10 mmol), 1-methyl-4-(4,4,5,5-teramethyl-1,3,2-dioxaborolan-2-yl)-1H-pyrazole (2.94 g, 14.2 mmol), Pd (dppf)Cl$_2$ (0.58 g, 10 mol %), sodium carbonate (3.75 g, 35.4 mmol) in 1,2-dimethoxyethane (60 mL) and water (15 mL) was stirred at 80° C. under Argon for 16 hours. The solvents were evaporated and the residue purified by column chromatography (SiO$_2$ 5% methanol/ethyl actetate→15% methanol/ethyl acetate) to afford compound 109 as a grey solid 1.50 g (99%). $^1$H NMR (400

MHz, DMSO-d₆ δ 8.27 (s, 1H), 7.88 (s, 1H), 7.72 (d, 1H), 7.64 (s, 1H), 7.26 (d, 1H), 6.91 (bs, 2H). HPLC-MS $t_R$=0.3 mn (UV$_{254\,nm}$). Mass calculated for formula C10H10N6, 214.1; observed MH⁺ (LC/MS) 215.2 (m/z).

Example 110

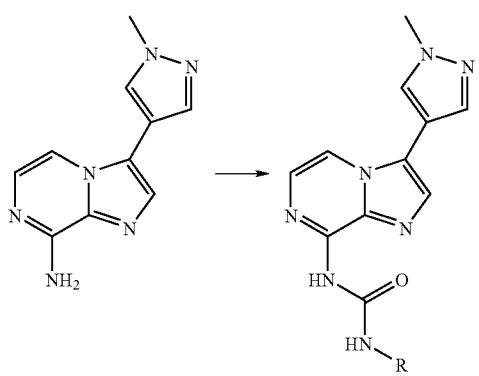

A solution of compound 109 (1 equivalent) in DMF (1 mL) was treated with NaH (60% dispersion in oil, 1.2 equivalents) for 15 minutes at room temperature. The respective isocyanate (1 equivalent) was then added to this solution at room temperature and the resultant solution was stirred overnight. When LC-MS analysis indicated the reaction was complete, the reaction mixture was concentrated. Purification by Prep-LC and conversion to a hydrochloric salt afforded compounds 110-1 to 1104.

TABLE 10

| Example | Column 2 | MW | LCMS MH⁺ m/z | HPLC MS $t_R$ |
|---|---|---|---|---|
| 110-1 | | 333.4 | 334.1 | 4.10 |
| 110-2 | | 285.3 | 286.2 | 2.30 |
| 110-3 | | 367.8 | 368.2 | 3.60 |
| 110-4 | | 397.8 | 398.2 | 3.60 |

Example 111

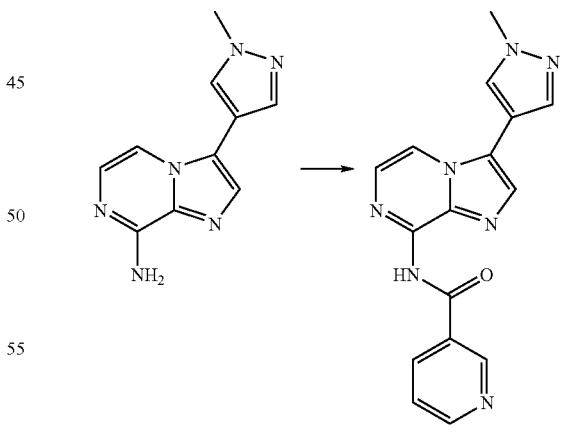

To a solution of nicotinic acid (25.0 mg, 0.203 mmol) in DMF (1.5 mL) was added compound 109 (65.2 mg, 0.304 mmol) and diisopropylethylamine (0.159 mL, 0.91 mmol). The reaction mixture was stirred at room temperature for 10 minutes, cooled to 0° C. (ice-bath) and then added HATU (115.6 mg, 0.304 mmol) and catalytic DMAP. The reaction mixture was allowed to warm to room temperature and then heated to 70° C., stirred overnight. LC-MS analysis indicated the reaction was complete. The reaction mixture was concentrated. Purification by Prep-LC and conversion to a hydrochloric salt afforded compound 111. HPLC-MS $t_R$=1.78 min ($UV_{254\ nm}$). Mass calculated for formula $C_{16}H_{13}N_7O$, 319.12; observed $MH^+$ (LC/MS) 320.2 (m/z).

Example 112

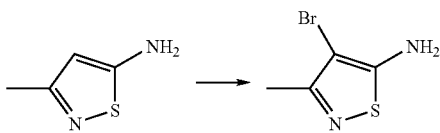

5-Amino-3-methyl isothiazole hydrochloride (5.00 g, 33.2 mmol) was added to water (35 mL). The insolubles were filtered and the filtrate's pH was adjusted to with the addition of 2N NaOH. The mixture was stirred for five minutes and extracted with ethyl ether. The organic layer was separated and the aqueous layer was saturated with NaCl, extracted with ethyl ether (100 mL, 2×). The combined ether extracts were washed with brine, dried over sodium sulfate and then concentrated to afford compound 112 as dark orange oil, 3.12 g (82%). $^1$H-NMR (400 MHz, DMSO-$d_6$) δ 6.5 (bs, 2H), 5.9 (s, 1H), 2.1 (s, 3H).

5-amino-3-methyl isothiazole (1.00 g, 8.75 mmol) was slurried in $CCl_4$ (30 mL) under an atmosphere of argon. N-Bromosuccinimide (1.56 g, 8.75 mmol) was added portion-wise to the amine slurry over a 10 minute period at room temperature. The reaction stirred at 65° C. for 1.5 hours. Thin layer chromatography (DCM/Hexanes 1:1) indicates the reaction is complete. The reaction mixture was cooled to room temperature and diluted with ethyl ether (40 mL). The resulting mixture was cooled to 5° C. for 30 minutes and filtered to remove any solid material. The filtrate was concentrated to yield a dark red solid that was dissolved in ethyl acetate and washed with water (100 mL, 2×). The organic layer was separated, washed with brine, dried over anhydrous sodium sulfate, and concentrated under vacuum to afford compound 112 as a dark red solid (1.49 g, 88%). This was used without further purification. $^1$H-NMR (400 MHz, DMSO-$d_6$) δ 6.7 (bs, 2H), 2.2 (s, 3H).

Example 113

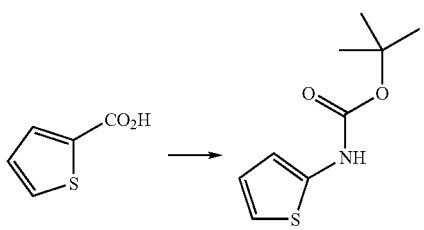

A solution of thiophene2-carboxylic acid (1.00 g, 7.8 mmol), diphenylphosphoryl azide (2.15 g, 7.80 mmol) and triethylamine (1.1 mL, 7.8 mmol) in tert-butanol (20 mL) was heated at reflux for 5 hours, at which time thin layer chromatography (DCM/Hexanes) indicates the reaction is complete. The reaction mixture was cooled to room temperature, poured into water and extracted with diethyl ether (3×). The combined ether extracts were washed with brine, dried over anhydrous sodium sulfate, and then concentrated to afford a beige solid. Purification by column chromatography ($SiO_2$, DCM/Hexanes) afforded compound 113 as a white solid 1.07 g (69%). $^1$H-NMR (400 MHz, DMSO-$d_6$) δ 6.87(dd,1H), 6.77 (m,1H), 6.5 (dd,1H), 1.46 (s, 9H).

Example 114

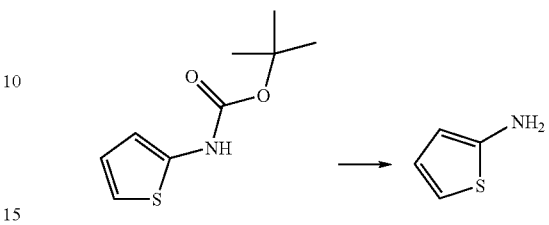

A solution of compound 113 (0.20 g, 1.00 mmol) was stirred in 4 M HCl solution in 1,4-dioxane (3 mL) at 50° C. for 2 hrs at which time thin layer chromatography (DCM/Hexanes) indicated the reaction was complete. The reaction mixture was cooled to room temperature and concentrated under vacuum. The residue was diluted with acetonitrile, sonicated, and concentrated to afford compound 114 as a grey solid 0.13 g (96%). $^1$H-NMR (400 MHz, DMSO-$d_6$) δ 7.38(m, 1H) 7.02 (m, 1H), 6.97 (m, 1H).

Example 115

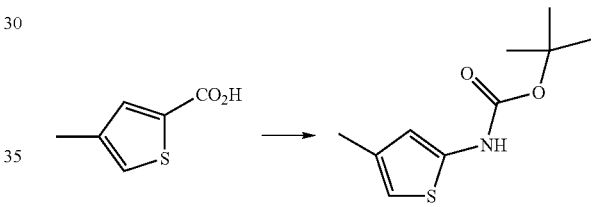

A solution of 4-methyl thiophene-2carboxylic acid (1.00 g, 7.03 mmol), diphenylphosphoryl azide (1.94 g, 7.03 mmol) and triethylamine (0.98 mL, 7.03 mmol) in tert-butanol (20 mL) was heated at reflux for 5 hours, at which time thin layer chromatography (DCM/Hexanes) indicates the reaction is complete. The reaction mixture was cooled to room temperature, poured into water and extracted with diethyl ether (3×). The combined ether extracts were washed with brine, dried over anhydrous sodium sulfate and then concentrated to afford a beige solid. Purification by column chromatography ($SiO_2$ DCM/Hexanes) afforded compound 115 as a white solid 0.96 g (64%). $^1$H-NMR (400 MHz, DMSO-$d_6$) δ 6.42(s, 1H), 6.35 (d,1H),2.08(s, H)1.46 (s, 9H).

Example 116

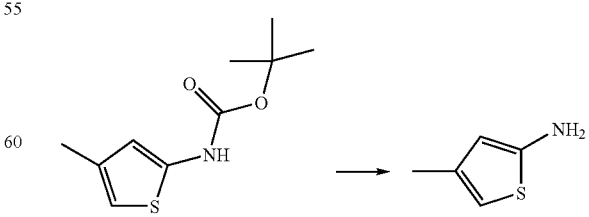

A solution of compound 115 (0.21 g, 1.00 mmol) was stirred in 4 M HCl solution in 1,4-dioxane (3 mL) at 50° C. for 2 hrs at which time thin layer chromatography (DCM/Hexanes) indicated the reaction was complete. The reaction mixture was cooled to room temperature and concentrated under vacuum. The residue was diluted with acetonitrile, sonicated, and concentrated to afford compound 116 as a grey solid 0.14 g (91%). $^1$H-NMR (400 MHz, DMSO-d$_6$) δ 11.6(bs, 2H) 6.83 (d, 1H), 6.7 (d, 1H), 4.55 (s, 3H).

Example 117

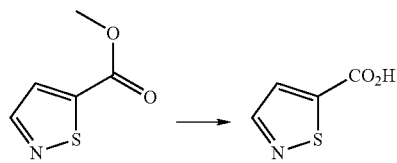

To a solution of isothiazole-5-carboxylic acid methyl ester (0.50 g, 3.49 mmol) in THF/MeOH (20 mL/5 mL) was added 1 N NaOH (5.24 mL, 5.24 mmol) at room temperature. The reaction mixture was stirred at room temperature for 16 hours at which time thin layer chromatography indicated the reaction was complete. The reaction mixture was acidified to pH 2 with 1 N HCl resulting in the formation of a precipitate, this was filtered and dried to afford compound 2 as a beige solid 0.35 g (76%). $^1$H-NMR (400 MHz, DMSO-d$_6$) δ 8.69 (d, 1H), 7.85 (d, 1H).

Example-118

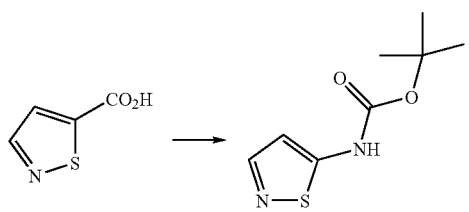

A solution of compound 117 (0.35 g, 2.67 mmol), diphenylphosphoryl azide (0.57 mL, 2.67 mmol) and triethylamine (0.37 mL, 2.67 mmol) in tert-butanol (10 mL) was heated at reflux for 5 hours, at which time thin layer chromatography (DCM/Hexanes) indicates the reaction is complete. The reaction mixture was cooled to room temperature, poured into water and extracted with diethyl ether (3×). The combined ether extracts were washed with brine, dried over sodium sulfate, and concentrated to afford a beige solid. Purification by column chromatography (SiO$_2$, 40% ethyl acetate/hexanes) afforded compound 118 as a white solid 0.245 g (46%). $^1$H-NMR (400 MHz, DMSO-d$_6$) δ 8.15(d,1H), 6.72 (d, 1H), 1.48 (s, 9H).

Example 119

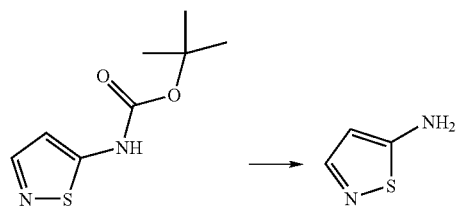

A solution of compound 118 (0.25 g, 1.22 mmol) was stirred in 4 M HCl solution in 1,4-dioxane (3 mL) at 50° C. for 2 hrs at which time thin layer chromatography (DCM/Hexanes) indicated the reaction was complete. The reaction mixture was cooled to room temperature and concentrated under vacuum. The residue was diluted with acetonitrile, sonicated, and concentrated to afford compound 119 as a grey solid 0.15 g (93%). $^1$H-NMR (400 MHz, DMSO-d$_6$) δ 8.09 (d, 1H), 6.26 (d, 1H).

Example 120

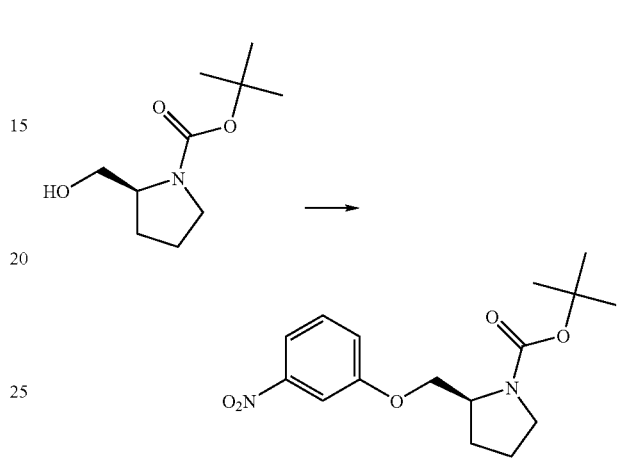

To a solution of 3-nitrophenol (0.35 g, 2.48 mmol, 1.00 equiv), triphenyl phosphine (0.68 g, 2.61 mmol, 1.05 equiv) and Boc-L-prolinol (0.53 g, 2.61 mmol, 1.05 equiv) in THF (10 mL) at rt was added drop wise diisopropyl azodicarboxylate (0.51 mL, 2.61 mmol, 1.05 equiv). The resulting solution was allowed to stir overnight at rt. Concentration and purification by chromatography (30% ethyl acetate in hexanes) afforded the title compound as a viscous oil (0.39 g, 48%).

Example 121

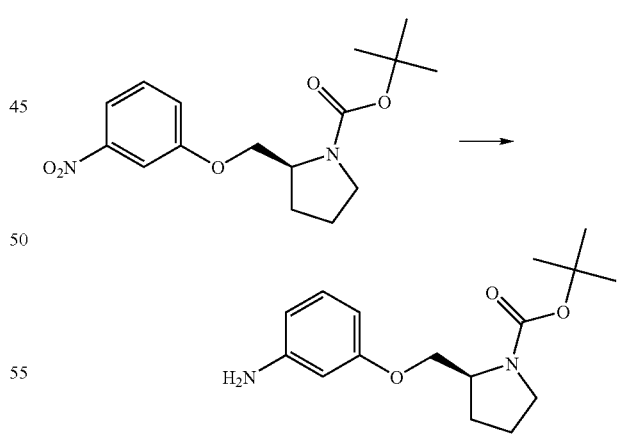

A suspension of (S)-2-(3-nitro-phenoxymethyl)-pyrrolidine-1-carboxylic acid tert-butyl ester (0.39 g) and 10% Pd/C (0.20 g) in ethanol was stirred under an hydrogen atmosphere (1 atm at balloon pressure) for 3.5 hr. The reaction mixture was filtered through a bed of Celite using ethyl acetate as solvent. Concentration afforded the title compound as a clear oil (0.316 g, 90%). $^1$H NMR (400 MHz, DMSO-d$_6$) δ 6.85 (t, 1H), 6.10 (app t, 3H), 5.00 (br s, 2H), 3.91 (app t, 1H), 3.71

(app t, 1H), 3.28-3.19 (m, 2H), 1.95-1.75 (m, 4H), 1.38 (s, 9H). LCMS: (MH−C$_4$H$_8$)$^+$=237.3.

Example 122

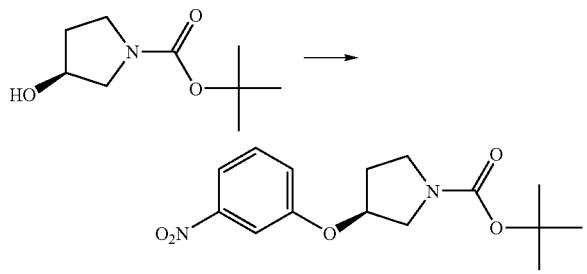

To a suspension of NaH (0.17 g, 4.4 mmol, 1.1 equiv) in DMSO (4 mL) at rt was added (3S)-1-Boc-3-pyrrolidinol (0.75 g, 4.0 mmol, 1.00 equiv) in one portion. After stirring for 20 min, 3-fluoronitrobenzene (0.51 g, 3.6 mmol, 0.90 equiv) was added drop wise and the resulting suspension was stirred an additional 1.5 hours at rt. The reaction mixture was quenched with the addition of saturated, aqueous NH$_4$Cl and extracted with ethyl acetate (3×). The combined organic layers were washed with brine, dried (Na$_2$SO$_4$), and concentrated. Purification of the crude residue by chromatography (30% ethyl acetate in hexanes) afforded 3-(3-nitro-phenoxy)-pyrrolidine-1-carboxylic acid tert-butyl ester as a bright yellow oil (0.676 g, 60%).

Example 123

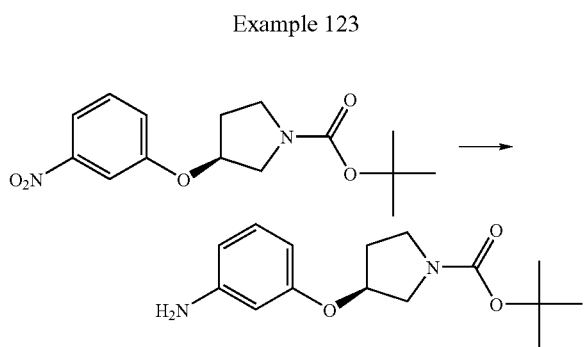

A suspension of 3-(3-nitro-phenoxy)-pyrrolidine-1-carboxylic acid tert-butyl ester (0.676 g) and 10% Pd/C (0.200 g) in ethanol was stirred under an hydrogen atmosphere (1 atm at balloon pressure) for 16 hr. The reaction mixture was filtered through a bed of Celite using ethyl acetate as solvent. Concentration afforded the title compound as a clear oil (0.529 g, 87%). $^1$H NMR (400 MHz, DMSO-d$_6$) δ 6.87 (t,1H), 6.14-6.03 (m, 3H), 5.04 (br s, 2H), 4.81 (br s, 1H), 3.52-3.23 (m,4H), 2.10-1.95 (m, 2H), 1.38 (d, 9H). LCMS: (MH−C$_4$H$_8$)$^+$=223.1.

Example 124

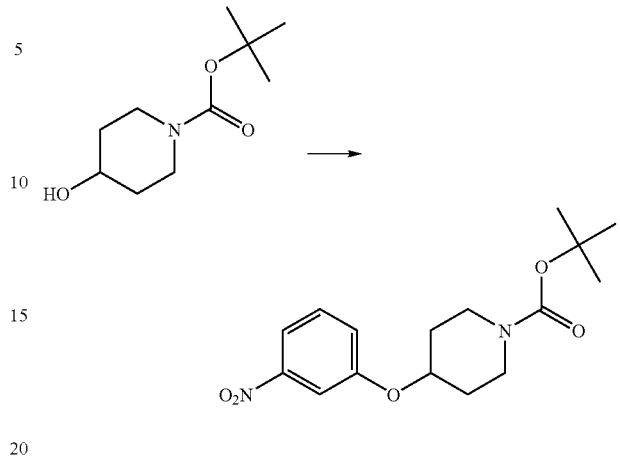

To a suspension of NaH (0.165 g, 4.14 mmol, 1.1 equiv) in DMSO (4 mL) at rt was added 1-BOC-4-hydroxypiperidine (0.794 g, 3.94 mmol, 1.00 equiv) in one portion. After stirring for 20 min, 3-fluoronitrobenzene (0.62 g, 4.34 mmol, 1.10 equiv) was added dropwise and the resulting suspension was stirred an additional 16 hours at rt. The reaction mixture was quenched with the addition of saturated, aqueous NH$_4$Cl and extracted with ethyl acetate (50 mL, 3×). The combined organic layers were washed with brine, dried with sodium sulfate and concentrated. Purification of the crude residue by chromatography (30% ethyl acetate in hexanes) afforded 4-(3-nitro-phenoxy)-piperidine-1l-carboxylic acid tert-butyl ester as a dark orange oil (0.390 g, 31%).

Example 125

A suspension of 4-(3-nitro-phenoxy)-piperidine-1-carboxylic acid tert-butyl ester (0.390 g) and 10% Pd/C (0.100 g) in ethanol was stirred under an hydrogen atmosphere (1 atm at balloon pressure) for 16 hr. The reaction mixture was filtered through a bed of Celite using ethyl acetate as solvent. Concentration afforded 4-(3-amino-phenoxy)-piperidine-1-carboxylic acid tert-butyl ester as a clear oil (0.353 g, 90%). $^1$H NMR (400 MHz, DMSO-d$_6$) δ 6.85 (t, 1H), 6.15-6.05 (m, 3H), 4.99 (br s, 2H), 4.43-4.30 (m, 1H), 3.67-3.53 (m, 2H), 3.20-3.06 (m, 2H), 1.89-1.80 (m, 2H), 1.53-1.4 (m, 2H), 1.38 (s, 9H).

Example 126

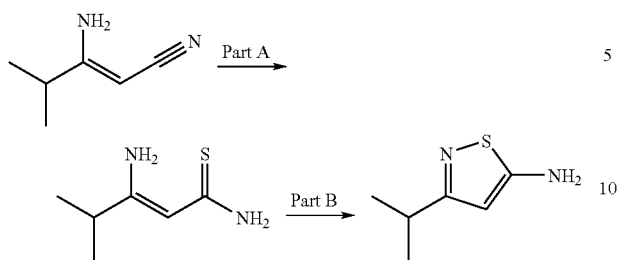

Part A

A solution of 3-amino-4-methyl-pent-2-enenitrile (Hackler, R. E., et. al. *J. Heterocyclic Chem.* 1989, 1575-1578) (0.700 g, 6.35 mmol, 1.00 equiv) in 1/1 THF/ethanol (5 mL) was cooled to 0° C. and treated with hydrogen sulfide gas for ca. 5 min. The tube was sealed and heated at 90° C. (16 hr). The reaction vessel was cooled in an ice-bath, carefully vented and the reaction mixture was concentrated. The crude residue was used in Part B without further purification.

Part B

A suspension of the crude residue from Part A and potassium carbonate (1.34 g, 9.71 mmol, 2.0 equiv) in diethyl ether (7 mL) was heated at reflux. To the reaction mixture was added drop wise a solution of iodine (1.2 g, 4.85 mmol, 1.00 equiv) in ether (7 mL). The mixture was heated at reflux for an additional 2 hr. Water and ethyl acetate were added. The aqueous phase was washed with ethyl acetate and the combined organic phases were washed with water, brine, and dried with sodium sulfate. Purification of the residue by chromatography (30% ethyl acetate in hexanes) afforded 449 mg (50% yield based on 3-amino-4-methyl-pent-2-enenitrile) of 3-isopropyl-isothiazol-5-ylamine as a waxy, orange solid. $^1$H NMR (400 MHz, DMSO-$d_6$) δ 6.46 (br s, 2H), 5.97 (s, 1H), 3.31 (dq, 1H), 1.12 (d, 6H), (MH)$^+$ (LCMS) 143.1(m/z)

Example 127

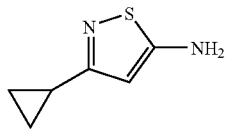

The title compound example 127 was prepared by the same procedure set forth in the above example 126, MH$^+$ (LCMS) 141.1(m/z).

Example 128

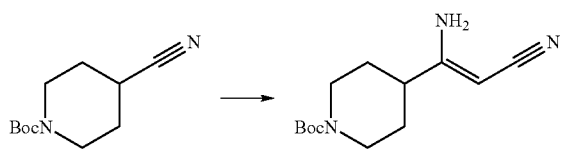

4-(1-Amino-2-cyano-vinyl)-piperidine-1-carboxylic acid tert-butyl ester was prepared from 4-cyano-piperidine-1-carboxylic acid tert-butyl ester (10.0 mmol) according to the procedure described in WO 2004/014910 A1 (p. 32). The crude residue was used in the next step without purification.

Example 129

A solution of crude 4-(1-amino-2-cyano-vinyl)-piperidine-1-carboxylic acid tert-butyl ester( compound 128) in 1:1 THF/Ethanol (10 mL) was cooled to 0° C. and treated with hydrogen sulfide gas for ca. 5 min. The tube was sealed and heated at 85° C. for 4 hr. The reaction vessel was cooled in an ice-bath, carefully vented and the reaction mixture was concentrated. The crude residue was used in the next step without purification.

Example 130

To the crude product from example 129 and potassium carbonate (2.1 g, 15.0 mmol) in diethyl ether (15 mL) at rt was added drop wise a solution of iodine (1.02 g, 4.0 mmol) in ether (6 mL). The mixture was stirred at rt for an additional 2 hr. Water and ethyl acetate were added. The aqueous phase was washed with ethyl acetate and the combined organic extracts were washed with water, brine and dried with sodium sulfate. Purification of the residue by chromatography (40% ethyl acetate in hexanes) afforded 250 mg of 4-(5-amino-isothiazol-3-yl)-piperidine-1-carboxylic acid tert-butyl ester (9% yield based on 4-cyano-piperidine-1-carboxylic acid tert-butyl ester). $^1$H NMR (400 MHz, DMSO-$d_6$) δ 6.51 (br s, 2H), 5.98 (s, 1H), 4.02-3.88 (m, 2H), 2.82-2.68 (m, 2H), 2.68-2.58 (m, 2H), 2.8-2.75 (m, 2H), 2.60-2.51 (m, 1H), 1.38 (s, 9H). LCMS: (M-$C_4H_8$)$^+$=228.1.

Example 131

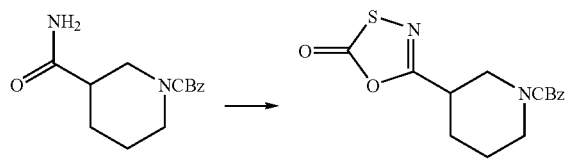

To a suspension of benzyl 4-(amino carbonyl)tetrahydro-1 (2H)-pyridinecarboxylate (2.79 g, 10.6 mmol, 1.00 equiv) in toluene (50 mL) was added chlorocarbonylsulfonyl chloride (0.97 mL, 11.7 mmol, 1.1 equiv) drop wise. The resulting suspension was refluxed for one hour, allowed to cool and then concentrated. The residue was dissolved in ethyl acetate and washed with saturated sodium bicarbonate, water, brine and dried with sodium sulfate. Concentration afforded 3-(2-oxo-[1,3,4]oxathiazol-5-yl)-piperidine-1-carboxylic acid benzyl ester as a clear, pale yellow oil, $MH^+$ (LCMS) 321.1 (m/z).

Example 132

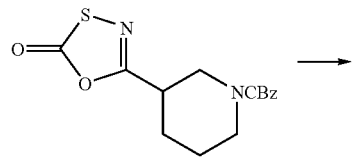

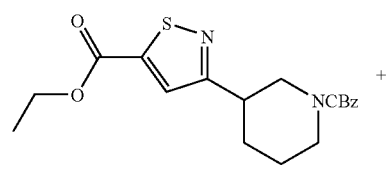

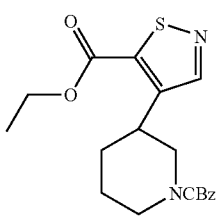

A solution of the crude residue from example 131 and ethyl propiolate (2 mL) in xylenes (15 mL) was heated in a sealed tube at 150° C. for 4 hr. Concentration and chromatographic purification (25% ethyl acetate and hexanes) afforded 3-(5-ethoxycarbonyl-isothiazol-3-yl )-piperidine-1-carboxylic acid benzyl ester and 3-(4-ethoxycarbonyl-isothiazol-3-yl )-piperidine-1-carboxylic acid benzyl ester as a 1:1 mixture (1.24 g), $MH^+$( LCMS) 375.1(m/z).

Example 133

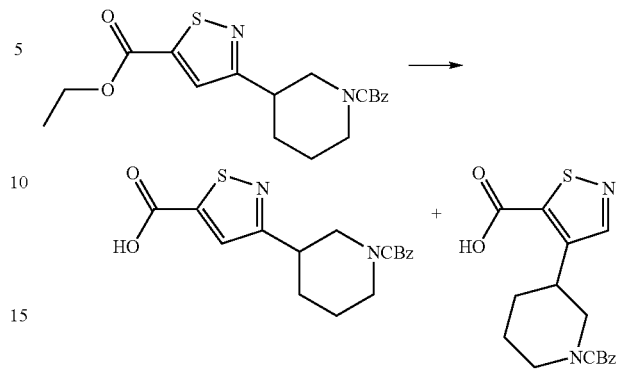

A solution of the residue from example 132 in THF (20 mL) and 1 N LiOH (6.7 mL) was heated at 50° C. for 4 hr. The reaction mixture was poured into ethyl acetate and acidified to pH 3 with 1 N HCl. The aqueous phase was extracted with ethyl acetate and the combined organic extracts were washed with water, brine, and dried with sodium sulfate. Concentration afforded 3-(5-carboxy-isothiazol-3-yl)-piperidine-1-carboxylic acid benzyl ester and 3-(4-carboxy-isothiazol-3-yl)-piperidine-1-carboxylic acid benzyl ester as a 1:1 mixture (1.02 g), $MH^+$(LCMS) 347.1(m/z).

Example 134 and 134-1

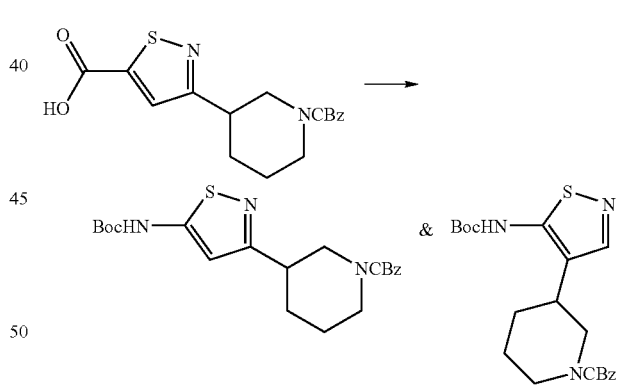

To a solution of crude residue from example 133 (1.02 g, 2.94 mmol, 1.00 equiv), N,N-diisopropylethylamine (0.56 mL, 3.23 mmol, 1.1 equiv) in tert-BuOH (25 mL) at rt was added diphenylphosphoryl azide (0.7 mL, 3.2 mmol, 1.1 equiv) drop wise. The resulting solution was refluxed for one hour and concentrated. The regioisomers were separated chromatographically (15% ethyl acetate in hexanes) affording 3-(5-tert-butoxycarbonylamino-isothiazol-3-yl )-piperidine-1-carboxylic acid benzyl ester (134; $R_f$=0.50 (15% ethyl acetate in hexanes), LCMS: $(MH)^+$=418.1 m/z) and 3-(4-tert-butoxycarbonylamino-isothiazol-3-yl)-piperidine-1-carboxylic acid benzyl ester (134-1; $R_f$=0.31 (15% ethyl acetate in hexanes), $MH^+$(LCMS) 418.1(m/z).

Example 135

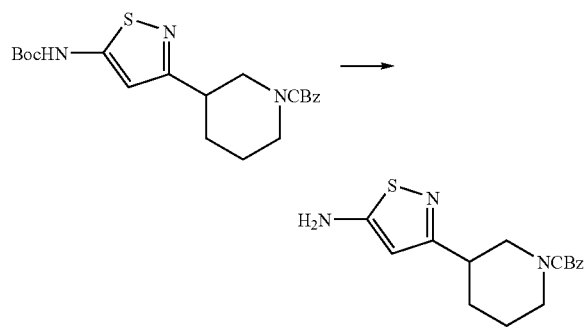

The crude residue from example 134 A was treated with 4 N HCl in dioxane at rt for 4 hours and then was concentrated. The residue was freeze-dried from a solution of acetonitrile and water. 3-(5-Amino-isothiazol-3-yl)-piperidine-1-carboxylic acid benzyl ester was used without further purification, MH$^+$(LCMS)318.2(m/z). 3-(4-amino-isothiazol-3-yl)-piperidine-1-carboxylic acid benzyl ester was prepared using the same method, MH$^+$ (LCMS) 318.2 (m/z).

Example 135-1

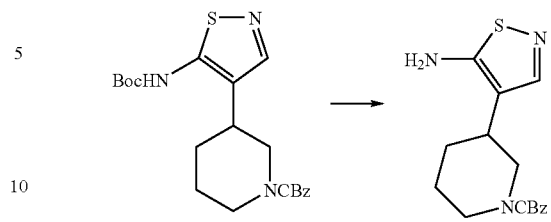

The crude residue from example 134-1 was treated with 4 N HCl in dioxane at rt for 4 hours and then was concentrated. The residue was freeze-dried from a solution of acetonitrile and water. 3-(5-Amino-isothiazol-3-yl)-piperidine-1-carboxylic acid benzyl ester was used without further purification. MH$^+$ (LCMS) 318.2(m/z). 3-(4-Amino-isothiazol-3-yl)-piperidine-1-carboxylic acid benzyl ester was prepared using the same method, MH$^+$(LCMS) 318.2 (m/z).

Examples 136-141

By essentially the same procedure set forth in Example 106, the compounds shown in column 3 were prepared from compounds given in column 2.

TABLE 11

| Example | Column 2 | Column 3 | MW | LCMS MH$^+$ m/z | HPLC MS $t_R$ |
|---|---|---|---|---|---|
| 136 | | | 466.1 | 467.2 | 1.66 |
| 137 | | | 475.2 | 476.2 | 1.80 |

TABLE 11-continued
| Example | Column 2 | Column 3 | MW | LCMS MH+ m/z | HPLC MS $t_R$ |
|---|---|---|---|---|---|
| 138 | 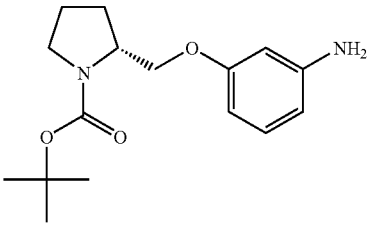 | 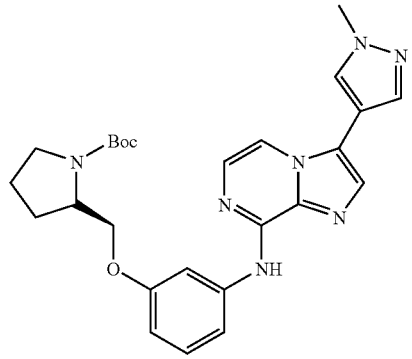 | 489.2 | 490.3 | 2.02 |
| 139 | 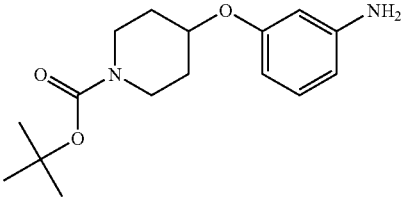 | 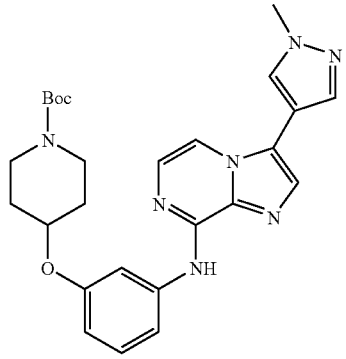 | 489.2 | 490.3 | 2.02 |
| 140 | 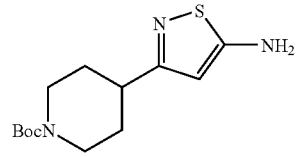 | 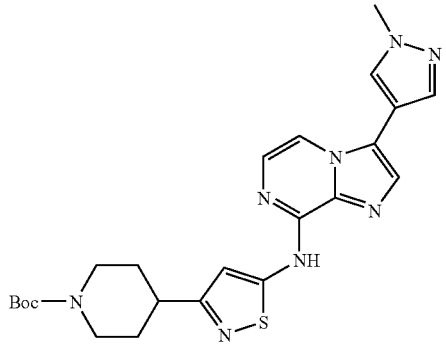 | 480.2 | 481.1 | 1.84 |
| 141 | 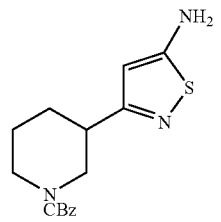 | 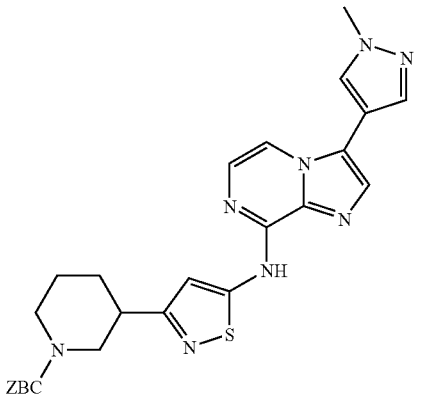 | 514.1 | 515.2 | 1.93 |

TABLE 11-continued

| Example | Column 2 | Column 3 | MW | LCMS MH+ m/z | HPLC MS $t_R$ |
|---|---|---|---|---|---|
| 141-1 | | | 514.1 | 515.2 | 2.02 |

Example 142

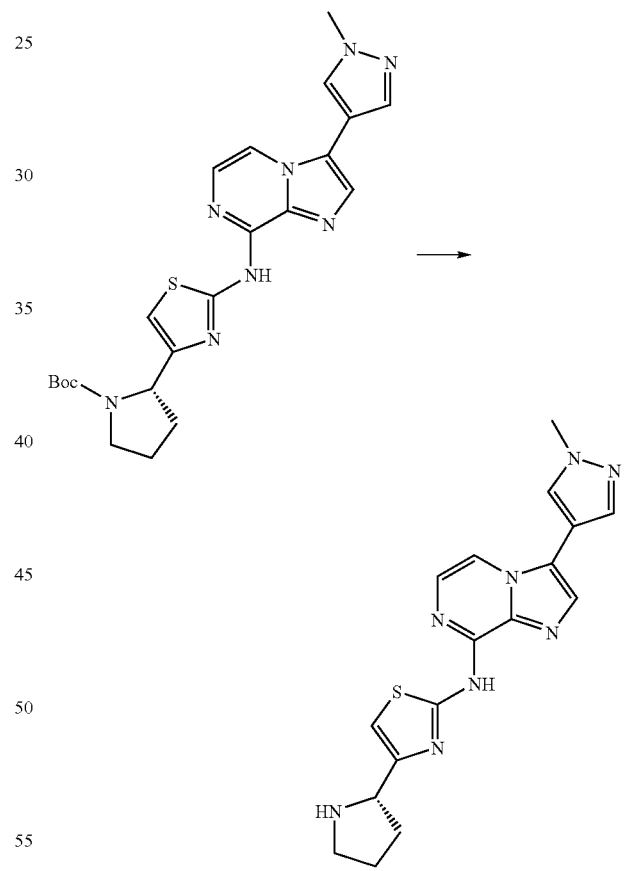

A solution of compound from example 121 (0.25 g,) was stirred in 4 N HCl solution in 1,4-dioxane (3 mL) at room temperature for 2 hrs at which time LC MS analysis indicated the reaction was complete. The reaction mixture concentrated under vacuum. The residue was diluted with acetonitrile, water, and lyophilized to afford compound 142; HPLC $t_R$=2.50 min, calculated molecular formula weight, 366.10; observed MH+ (LCMS) 367.2(m/z).

By essentially the same procedure given in example 142, starting from compounds given in column 2, compounds given in column 3 in Table 12 can be prepared:

TABLE 12

| Example | Column 2 | Column 3 | MW | LCMS MH+ m/z | HPLC MS t$_R$ |
|---|---|---|---|---|---|
| 143 | | | 375.2 | 376.2 | 2.18 |
| 144 | | | 389.2 | 390.2 | 2.27 |
| 145 | | | 389.2 | 390.2 | 2.26 |
| 146 | | | 380.2 | 381.2 | 2.23 |

TABLE 12-continued

| Example | Column 2 | Column 3 | MW | LCMS MH+ m/z | HPLC MS $t_R$ |
|---|---|---|---|---|---|
| 147 | 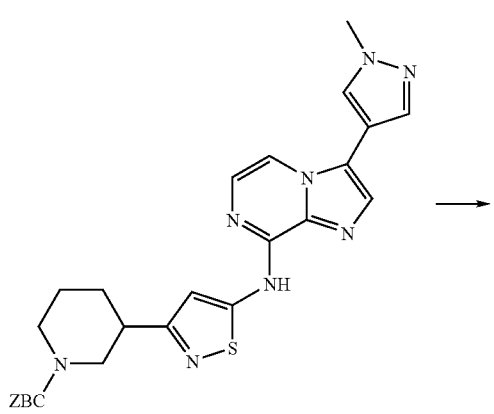 | 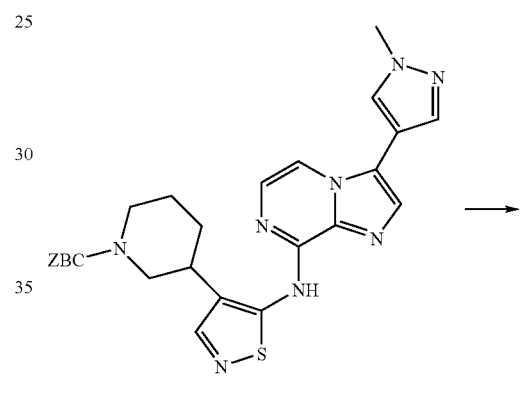 | 345.2 | 346.2 | 0.85 |

Example 148

Example 148-1

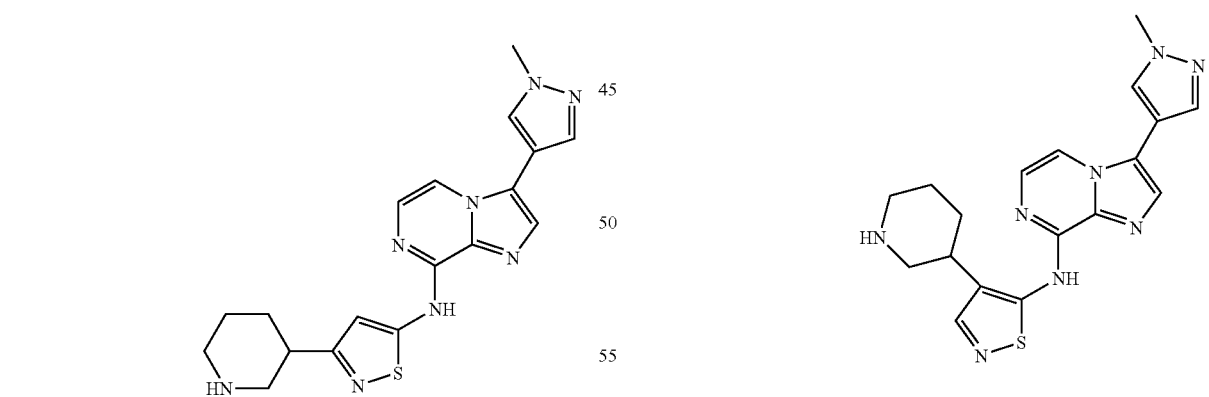

A suspension of compound from example 141 (0.05 g) and 4 N HCl in dioxane was stirred at 60° C. for 1 hr. The reaction mixture evaporated to dryness, dissolved in acetonitrile-water(1:1), and lyophilized to give the product 147. HPLC $t_R$=2.49 min, calculated molecular formula weight 380.2, observed MH+(LCMS) 381.2(m/z).

By essentially the process in example 148-1 can be prepared from the procedure described in example 148. HPLC tR=2.66 min, calculated molecular weight, 380.2, observed MH+ (LCMS) 381.2(m/z).

Example 149

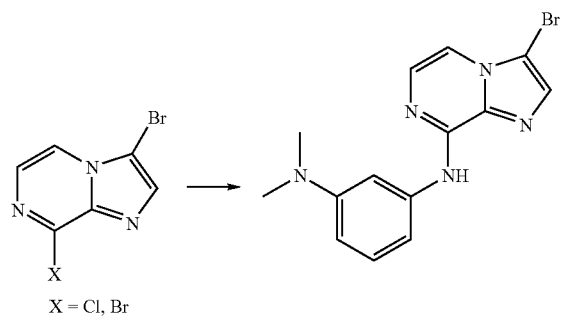

X = Cl, Br

The mixed halo-products (3:1 Cl:Br) from Preparative Example 102 (3.67 g, 15.0 mmol), were combined with N,N-dimethyl-m-phenylenediamine.2HCl (4.71 g, 22.5 mmol), i-Pr₂NEt (15.7 mL, 90.2 mmol), and NMP solvent (75 mL). The reaction was heated in an oil bath at 160° C. for 18 hours. The reaction was cooled and concentrated under vacuum. The crude material was purified by column chromatography; 2 columns using a gradient of 20% EtOAc/Hexanes increasing to 50% EtOAc/Hexanes. The product, 148 was isolated in 95% purity as determined by $^1$H NMR(400 MHz DMSO-$d_6$) δ 9.36 (s, 1H), 7.77 (s,1H), 7.74 (d, J=4.4 Hz, 1H), 7.54 (d, J=4.8 Hz, 1H), 7.47 (m, 1H), 7.42 (t, J=2.0 Hz), 7.09 (t, J=8.0 Hz, 1H), 6.40 (dd, J=8.0 Hz, 2.0 Hz, 1H), 2.87 (s, 6H). Product was isolated in 77% yield, 3.83 g.

Example 150-1 to 150-30

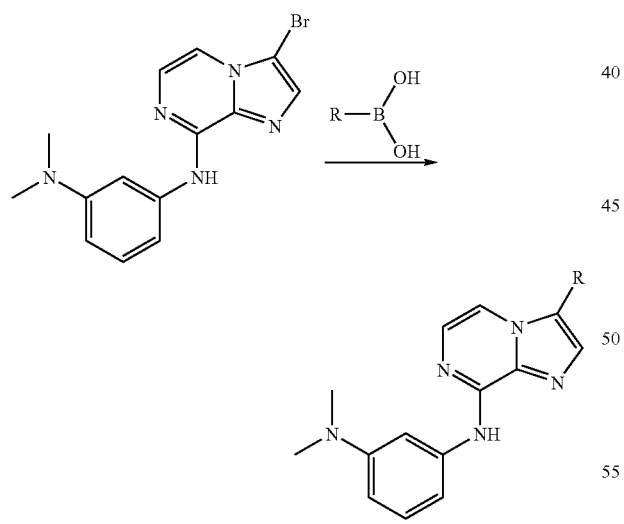

A 1.5 M solution of Na₂CO₃ in H₂O (0.5 mL) was added to 4 mL vials containing 10 mol % Pd(dppf)Cl₂ and 1.5 eq. of the appropriate boronic acid. The product from example 149 was added last as a 0.06 M solution in DME (2.0 mL). The reactions were flushed with Argon, capped, and placed in a sand bath at 80° C. overnight. The reactions were cooled, concentrated, and purified via preparative HPLC to give products 150.

TABLE 13

| Example | Product | MW | LCMS MH⁺ m/z | HPLC MS $t_R$ (min) |
|---|---|---|---|---|
| 150-1 | | 407.5 | 408.3 | 1.30 |
| 150-2 | | 380.5 | 381.2 | 1.50 |
| 150-3 | | 380.5 | 381.2 | 1.42 |
| 150-4 | | 407.5 | 408.1 | 1.29 |

TABLE 13-continued

| Example | Product | MW | LCMS MH+ m/z | HPLC MS t_R (min) |
|---|---|---|---|---|
| 150-5 | | 335.4 | 336.2 | 3.15 |
| 150-6 | | 354.4 | 355.2 | 3.23 |
| 150-7 | | 330.4 | 331.2 | 1.79 |
| 150-8 | | 346.4 | 347.2 | 1.98 |
| 150-9 | | 354.4 | 355.2 | 3.25 |
| 150-10 | | 359.4 | 360.3 | 3.41 |
| 150-11 | | 365.4 | 366.3 | 3.65 |
| 150-12 | | 375.5 | 376.2 | 3.86 |

TABLE 13-continued

| Example | Product | MW | LCMS MH+ m/z | HPLC MS t_R (min) |
|---|---|---|---|---|
| 150-13 | | 401.5 | 402.2 | 3.93 |
| 150-14 | | 398.5 | 399.3 | 4.23 |
| 150-15 | | 414.5 | 415.3 | 3.52 |
| 150-16 | | 371.4 | 372.2 | 3.42 |
| 150-17 | | 391.5 | 392.2 | 2.55 |
| 150-18 | | 349.5 | 350.2 | 3.85 |
| 150-19 | | 372.4 | 373.2 | 2.39 |
| 150-20 | | 377.5 | 378.2 | 3.29 |

TABLE 13-continued
| Example | Product | MW | LCMS MH+ m/z | HPLC MS $t_R$ (min) |
|---|---|---|---|---|
| 150-21 | 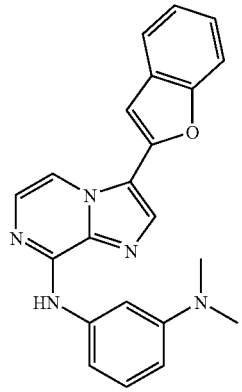 | 369.4 | 370.2 | 4.23 |
| 150-22 | 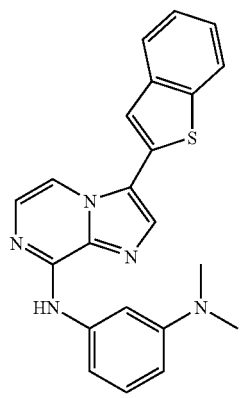 | 385.5 | 386.2 | 4.36 |
| 150-23 | 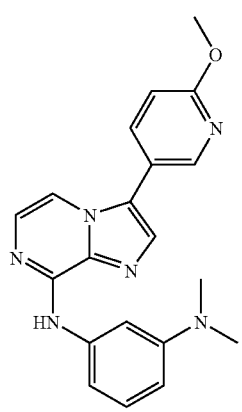 | 360.4 | 361.2 | 3.05 |
TABLE 13-continued
| Example | Product | MW | LCMS MH+ m/z | HPLC MS $t_R$ (min) |
|---|---|---|---|---|
| 150-24 | 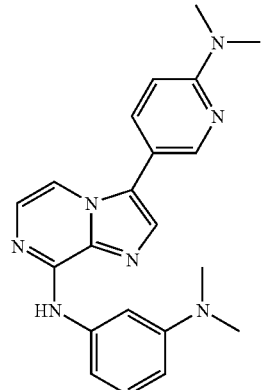 | 373.5 | 374.2 | 2.83 |
| 150-25 | 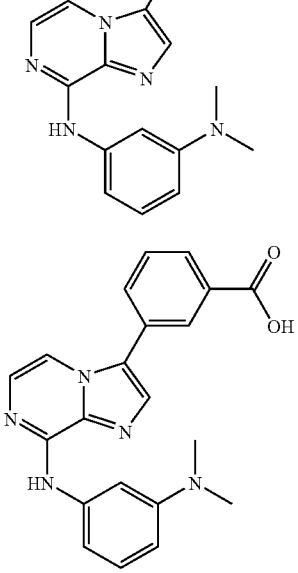 | 373.4 | 374.3 | 2.02 |
| 150-26 | 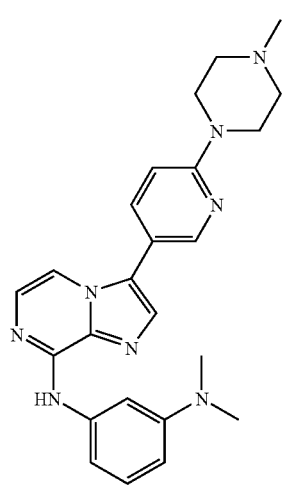 | 428.5 | 429.3 | 2.10 |
| 150-27 | 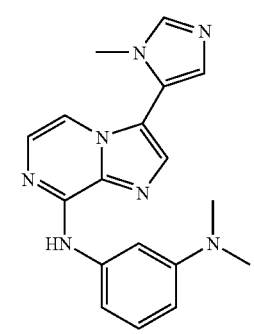 | 333.4 | 334.2 | 0.72 |

TABLE 13-continued

| Example | Product | MW | LCMS MH+ m/z | HPLC MS $t_R$ (min) |
|---|---|---|---|---|
| 150-28 | | 361.5 | 362.2 | 2.68 |
| 150-29 | | 364.5 | 365.2 | 3.05 |
| 150-30 | | 375.2 | 376.3 | 1.51 |
| 150-31 | | 409.2 | 410.2 | 1.53 |

Example 151

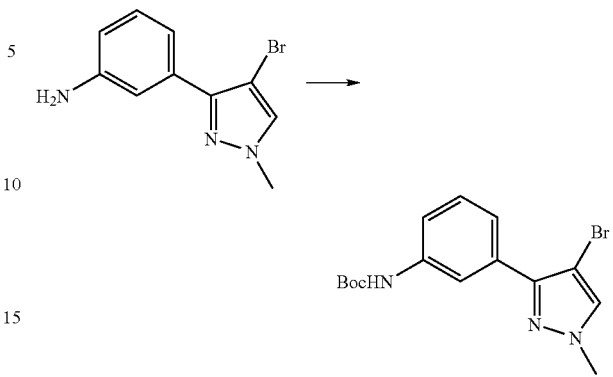

To the mixture of 3-(4-bromo-1-methyl-1H-pyrazol-3-yl-)phenyl amine (1.78 g, 7.1 mmol), imidazole (1.36 g, 20 mmol), and catalytic amount DMAP in DMF (12 mL), $(BOC)_2 O$ (1.7 g, 7.8 mmol) was added at room temperature. The mixture was stirred overnight and diluted with EtOAc (200 mL), the organics were washed with $H_2O$, brine and dried over $Na_2SO_4$. After concentration, the residue was purified with column chromatography (silica gel, hexane/EtOAc=70/30) to give the product 151(2.52 g) as white solid. HPLC-MS $t_R$=2.00 min (UV 254 nm). Mass calculated for formula $C_{15}H_{18}BrN_3O_2$, 351.1; observed MH+ LC/MS 352.1 (m/z).

Example 152

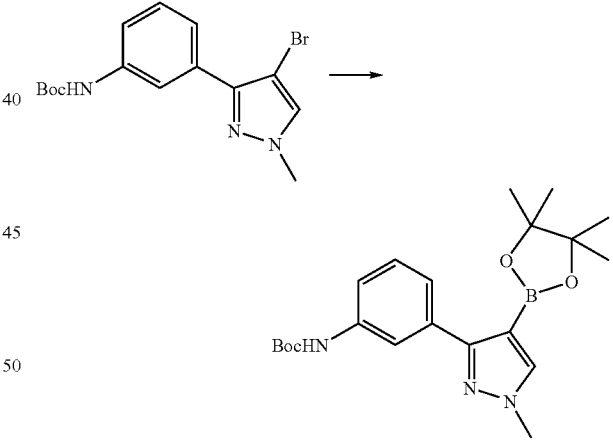

To a 25 mL round bottom flask charged with bis(pinacolato)diboron (1.0 g, 4.0 mmol), KOAc (960 mg, 10 mmol), Pd(dppf)Cl$_2$ (240 mg, 0.30 mmol) and product from example 151 (1.16 g, 3.30 mmol) was added DMSO (6 mL) under argon. The mixture was degassed thoroughly. This resulting mixture was then heated at 80° C. overnight, diluted by EtOAc (40 mL) and filtered through celite. After concentration, the residue was purified with column chromatography (silica gel, hexane/EtOAc=80/20) to give the product 152 (997 mg) as an oil. HPLC-MS $t_R$=2.11 min (UV254 nm); mass calculated for formula $C_{21}H_{30}BN_3O_4$, 399.2; observed MH+ LCMS 400.3(m/z).

Example 153

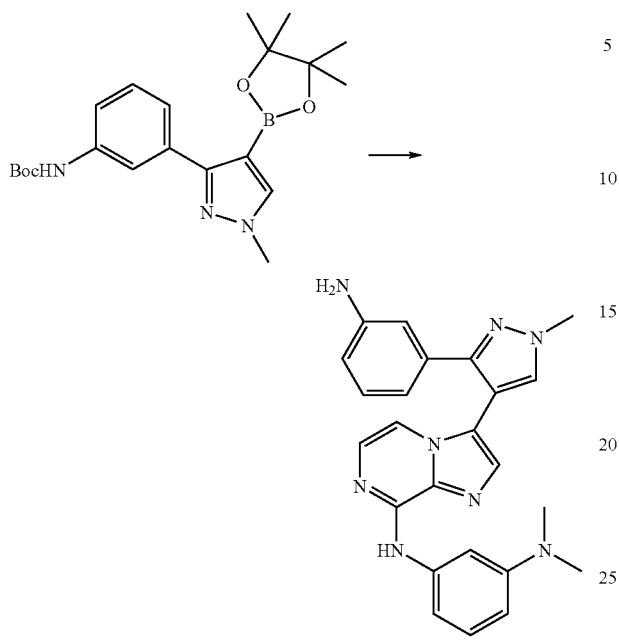

Under argon, the boronate compound 152 (120 mg, 0.3 mmol) in THF (3.0 mL, 5%, H₂O) was added to the flask which was charged with Pd(dppf)Cl₂ (8.0 mg, 10 mol %), K₂CO₃ (138 mg, 1.0 mmol), and 3-bromoimidazopyrazine 149 (51 mg, 0.15 mmol). The mixture was degassed thoroughly with argon. The resulting solution was heated up to 80° C. and stirred overnight. After cooling to room temperature, the mixture was diluted with EtOAc (50 mL) and the solid was removed by filter through Celite and washed with some EtOAc. Concentration resulted in a residue 153 and was used in the next step directly without further purification. HPLC-MS $t_R$=2.05 min (UV$_{254\ nm}$); mass calculated for formula $C_{29}H_{32}N_8O_2$; 524.3, observed MH⁺ (LCMS) 525.2.1 (m/z).

Example 154

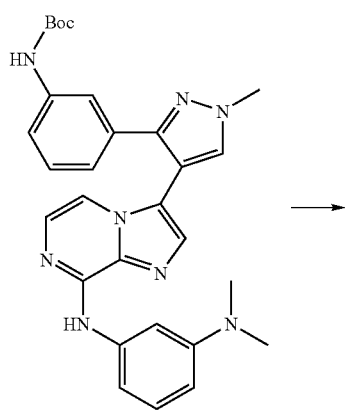

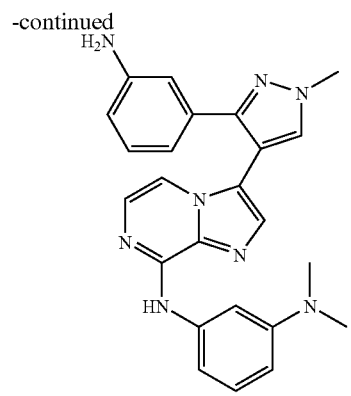

To the product from example 153 was added HCl (6 N, 3 mL), and the mixture was stirred at room temperature for 10 min. The reaction was concentrated, and the residue purified with HPLC to give the compound 154 (48 mg). HPLC-MS $t_R$=1.16 min (UV$_2$54 nm); mass calculated for formula $C_{24}H_{24}N_8$, 424.2; Observed MH⁺ (LCMS) 425.2 (m/z).

Example 155

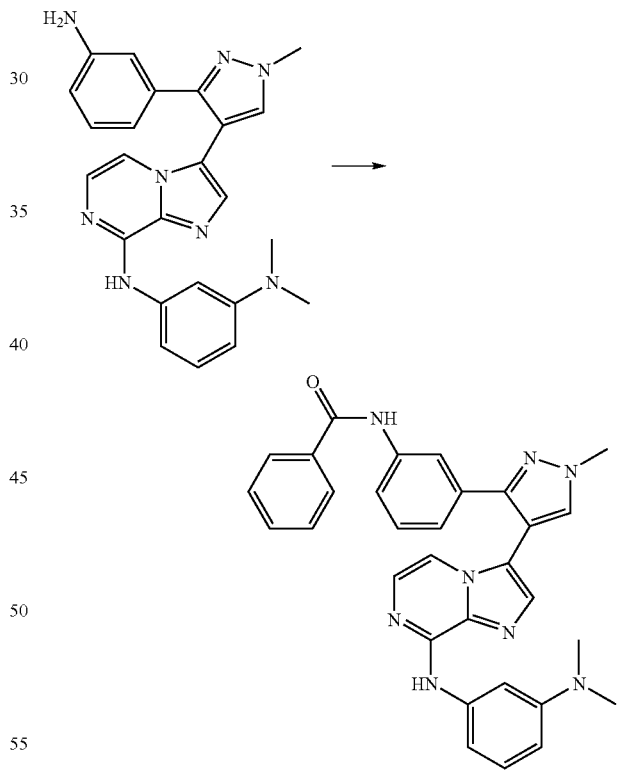

To a mixture of hydroxy benzotriazole (7 mg, 0.05 mmol and benzoic acid (6 mg, 0.05 mmol) in DMF (1 mL), EDC (10 mg, 0.05 mmol) was added and the mixture was stirred at room temperature for 10 min. Then product 154 (21 mg, 0.05 mmol) in DMF (1 mL) was added and the resulting mixture was heated up to 50° C. and stirred overnight. The mixture was diluted with EtOAc (50 mL), washed with H₂O, brine and dried over Na₂SO₄. After concentration the residue was purified by prep-LC to give the product 155. HPLC-MS $t_R$=1.54 min (UV$_{254\ nm}$); mass calculated for formula $C_{31}H_{28}N_8O$, 528.2; observed MH⁺ (LCMS) 529.3 (m/z).

Example 156

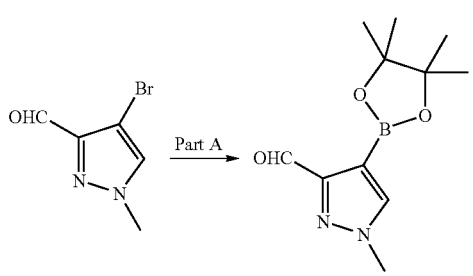

Compound 156 was prepared using the boronation conditions described in Example 152. HPLC-MS $t_R$=1.83 min (UV$_{254\ nm}$); mass calculated for formula $C_{11}H_{17}BN_2O_3$, 236.1; observed MH$^+$ (LCMS) 237.3 (m/z).

Example 157

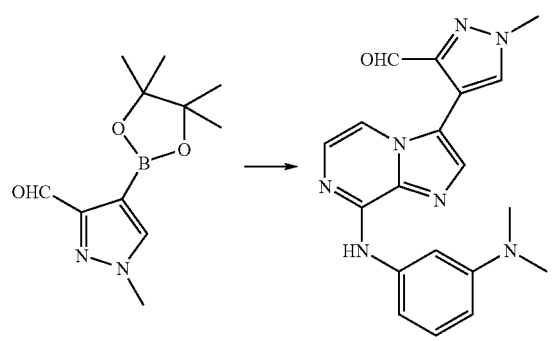

Compound 157 was prepared using the coupling conditions described in example 153. HPLC-MS $t_R$=1.18 min (UV$_{254\ nm}$); mass calculated for formula $C_{19}H_{19}N_7O$, 361.2; observed MH$^+$ (LCMS) 362.1 (m/z).

Example 158

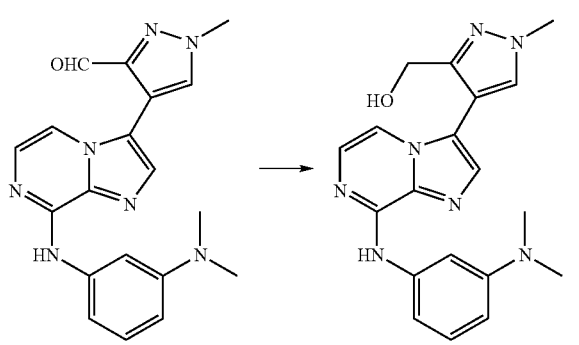

Product from example 157 (50 mg, 0.14 mmol) was dissolved in MeOH (5 mL) and the mixture cooled to 0° C. NaBH$_4$ (38 mg, 1.0 mmol) was added and the resulting mixture was stirred at 0° C. for 30 min. After concentration, the residue was purified with prep-LC gave the product 158. HPLC-MS $t_R$=0.92 min (UV$_{254\ nm}$); mass calculated for formula $C_{19}H_{21}N_7O$, 363.2; observed MH$^+$(LCMS) 364.3 (m/z).

Example 159

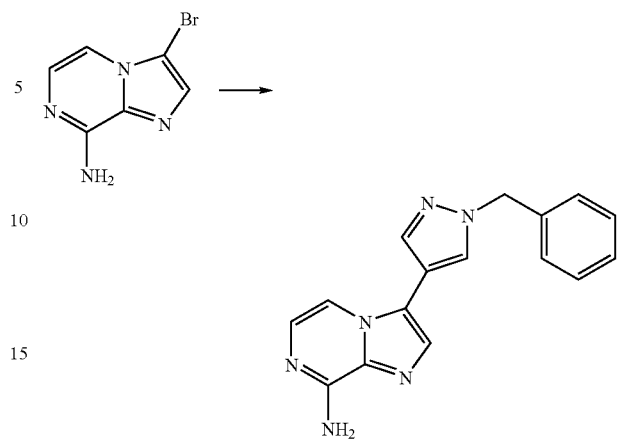

Product of example 159 was prepared using the coupling condition described in 153. HPLC-MS $t_R$=0.94 min (UV$_{254\ nm}$); mass calculated for formula $C_{16}H_{14}N_6$ 290.1, observed MH$^+$ (LCMS) 291.3 (m/z).

Example 160

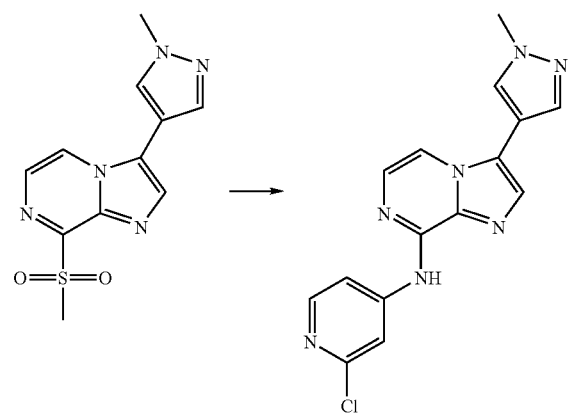

By essentially the same procedure given in example 106, combining the product from example 105 and 2-chloro-4-amino pyridine to give the product 160. HPLC tR=1.45 min. Calculated molecular weight, 325.1, observed MH$^+$(LCMS) 326.0(m/z).

Example 161

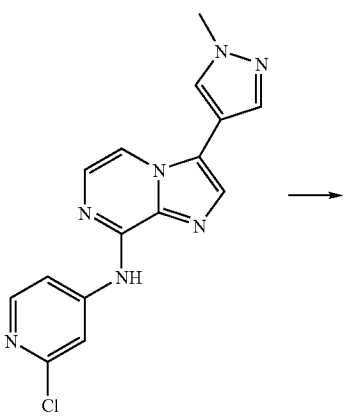

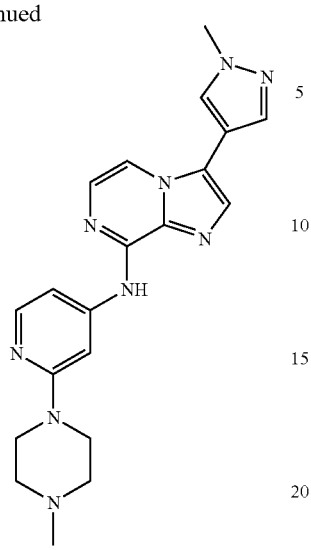

A mixture of the product from example 160, 1-methyl piperazine (excess) is stirred and heated at 100° C. for 72 hrs. The mixture poured in to 10% aqueous $Na_2CO_3$ and extracted with ethyl acetate. The extracts dried over sodium sulfate, filtered and evaporated. Preparative HPLC purification afford the product, HPLC $t_R$=1.92 min. Calculated molecular weight=389.5, observed $MH^+$ (LCMS) 390.30(m/z).

By essentially the same procedure given in example 161, combining intermediates from preparative example 160 with the amines given in column 1, compounds given in column 2 were prepared. The compounds obtained were purified by preparative HPLC. The purified products were treated with 4 N HCl in dioxane to remove the BOC protecting group. The volatiles were removed under vacuum. The product was dissolved in acetonitrile-water and lyophilized to give the product(s).

TABLE 14

| Example | Column 1 | Column 2 | MW | LCMS $MH^+$ m/z | HPLC MS $t_R$ |
|---|---|---|---|---|---|
| 163 | | | 375.1 | 376.1 | 0.75 |
| 164 | | | 389.2 | 390.2 | 0.75 |

TABLE 14-continued

| Example | Column 1 | Column 2 | MW | LCMS MH+ m/z | HPLC MS t_R |
|---------|----------|----------|------|--------------|-------------|
| 164-1   | Boc-piperazine | | 375.1 | 376.0 | 1.94 |

Example 165

Example 166

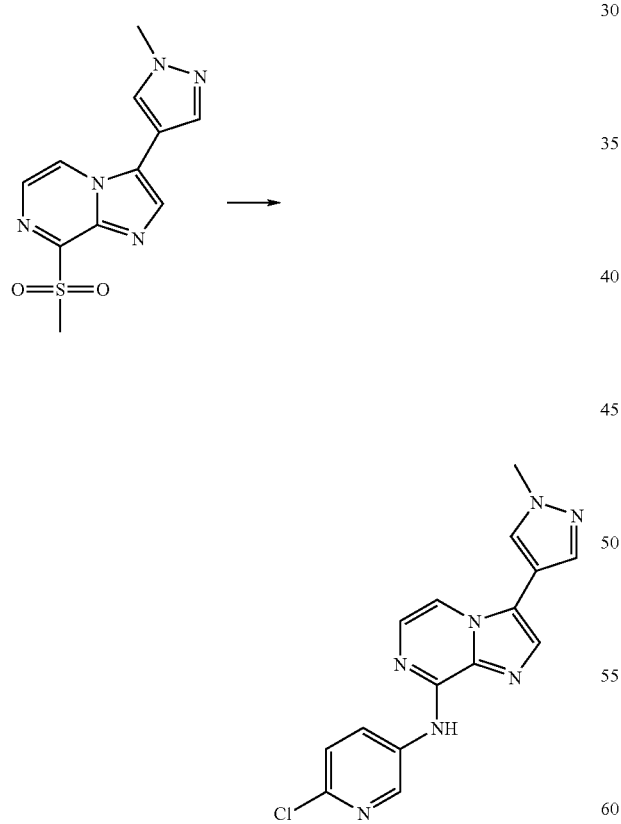

By essentially the same procedure given in example 106, combining the product from example 105 and 2-chloro-4-amino pyridine to give the product 165. HPLC tR=1.48 min. Calculated molecular weight, 325.1; observed MH+ (LCMS), 326.0(m/z).

A mixture of the product from example 165, 1-methyl piperazine (excess) is stirred and heated at 100° C. for 72 hrs. The mixture poured into 10% aqueous $Na_2CO_3$ and extracted with ethyl acetate. The extracts were dried over sodium sulfate, filtered and evaporated. Preparative HPLC purification afforded the product. HPLC tR=1.80 min. Calculated molecular weight, 389.5.1; observed MH+ (LCMS) 390.23 (m/z).

By essentially the same procedure given in example 161, combining intermediates from preparative example 160 with the amines given in column 1, compounds given in column 2 were prepared. The compounds obtained were purified by preparative HPLC. The purified products obtained were treated with 4 N HCl dioxane to remove the BOC protecting group and volatiles were removed under vacuum. The product was dissolved in acetonitrile-water and lyophilized to give the product(s).

TABLE 15

| Example | Column 1 | Column 2 | MW | LCMS MH+ m/z | HPLC MS $t_R$ |
|---------|----------|----------|------|--------|------|
| 167 | H₂N-CH₂CH₂-NH-Boc | [structure] | 349.1 | 350.1 | 0.50 |
| 168 | (3S)-3-(Boc-amino)pyrrolidine | [structure] | 375.4 | 376.2 | 0.80 |
| 169 | 4-(N-Boc-N-methylamino)piperidine | [structure] | 403.4 | 404.2 | 0.85 |

Example 170

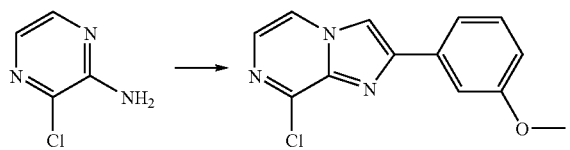

To a solution of 2-amino-3-chloropyrazine (0.20 g, 1.5 mmol, 1.00 equiv) and 3-methoxyphenacyl bromide (0.71 g, 3.1 mmol, 2.0 equiv) in dioxane (10 mL) was heated at 90° C. for 3 hr. The resulting mixture was cooled to rt and filtered. The filtrate was partitioned between 10% IPA/DCM and 1 N NaOH. The aqueous extract was washed with 10% IPA/DCM (2×) and the combined organic extracts were washed with brine and dried with sodium sulfate. Concentration afforded 8-chloro-2-(3-methoxy-phenyl)-imidazo[1,2-a]pyrazine (76 mg, 19%). MH+ (LCMS) 260.1 (m/z).

Example 171

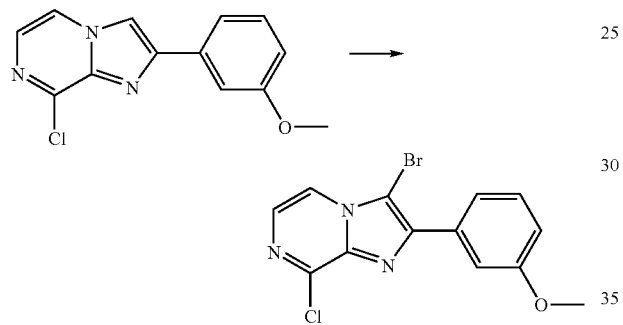

To the product from example 170 in acetic acid (10 mL) was added a solution of bromine in acetic acid (0.25 mmol, 1 mL). Concentration of the reaction mixture afforded crude 3-bromo-8-chloro-2-(3-methoxy-phenyl)-imidazo[1,2-a]pyrazine. MH+ (LCMS) 338.0(m/z).

Example 172

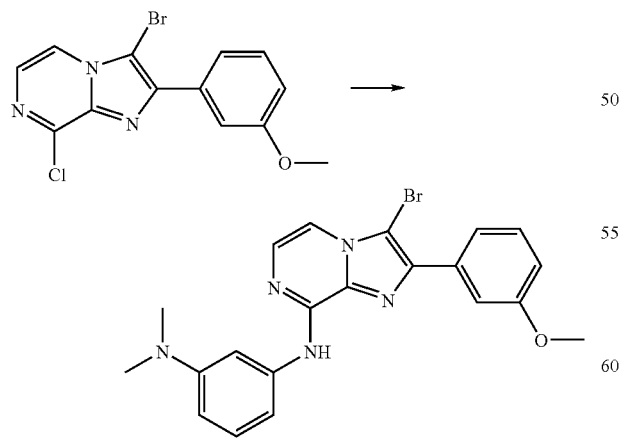

A solution of 3-bromo-8-chloro-2-(3-methoxy-phenyl)-imidazo[1,2-a]pyrazine (0.13 g, 0.38 mmol, 1.00 equiv) product from example 171, N,N-dimethyl-m-phenylenediamine hydrochloride (0.15 g, 0.71 mmol, 1.9 equiv) and N,N-diisopropylethylamine (0.33 mL, 1.9 mmol, 5.0 equiv) in NMP (2 mL) was heated at 140° C. for 20 h. Concentration and purification by chromatography (25% ethyl acetate in hexanes) afforded the title compound. MH+ (LCMS) 438.1 (m/z).

Example 173

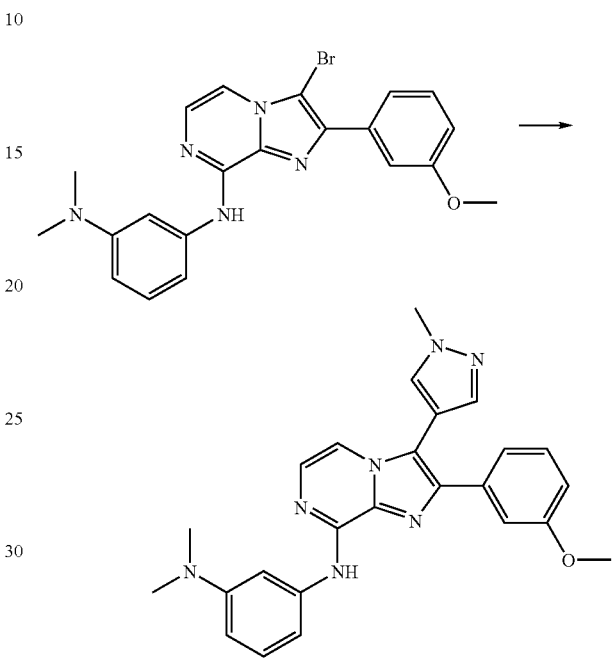

A suspension of 3-bromo-8-chloro-2-(3-methoxy-phenyl)-imidazo[1,2-a]pyrazine (38.2 mg, 0.0871 mmol, 1.00 equiv), [1,1'-bis(diphenylphosphino) ferrocene]dichloropalladium(II) (3 mg, 0.004 mmol, 5 mol %),1-methyl-4-(4,4,5,5-tetramethyl-1,3,2-dioxaborolan-2-yl)-1H-pyrazole (0.036 g, 0.17 mmol, 2.0 equiv) and sodium carbonate (0.028 g, 0.26 mmol, 3.0 equiv) in 1,2-dimethoxy ethane/water (0.4 mL/0.1 mL) was heated at 90° C. for 2.5 hr. The mixture was allowed to cool, filtered, concentrated and purified using chromatography (25% ethyl acetate in hexanes). The title compound was obtained as a colorless solid. HPLC $t_R$=1.68 min), MH+ (LCMS) 440.2 (m/z).

Example 174

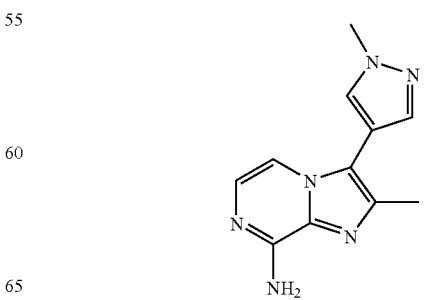

The title compound, example 174 was prepared by the same procedure set forth in the above example 173 HPLC ($t_R$=0.64 min).Calculated M.Wt. 228.1, observed MH+ (LCMS) 229.1 (m/z).

Example 175

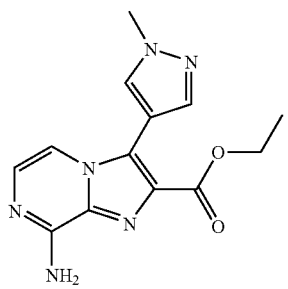

The title compound, example 175 was prepared by the same procedure set forth in the above example 173. HPLC ($t_R$=0.75 min).Calculated M.Wt. 286.2, observed MH+ (LCMS) 287.2 (m/z).

Example 176

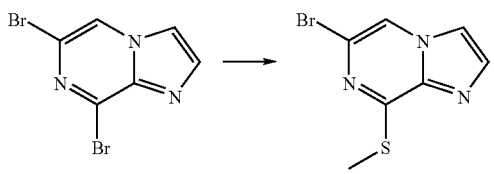

The dibromo compound 29 (2.16 g, 6.0 mmol) was dissolved in MeOH (20 mL). NaSMe (840 mg, 12 mmol) was added. The mixture was stirred for 2 hours at room temperature and concentrated. The residue was taken up in $H_2O$ (20 mL) and extracted with DCM/iso-PrOH (9/1) ( 50 mL, 3×). The combined organic layers were dried over $Na_2SO_4$ and concentrated. The crude compound was purified with column chromatography (silica gel, EtOAc/hexane=40/60 to 100% EtOAc) to give the pure compound 176 (1.12 g) as yellowish solid. $^1$H NMR (400 MHz, $CDCl_3$) δ 7.97 (s, 1H), 7.68 (d,1H), 7.57 (d, 1H), 2.66 (s, 3H). HPLC-MS $t_R$=1.40 min ($UV_{254\ nm}$); mass calculated for formula $C_7H_6BrN_3S$, 242.9; observed MH+ (LCMS) 244.1 (m/z).

Example 177 & 178

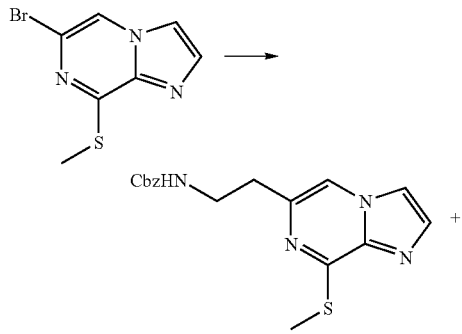

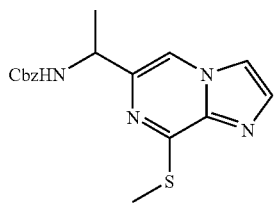

Under Ar, a solution of 9-BBN (10 mL, 0.5 M in THF) was added drop wise to the solution of benzyl N-vinylcarbamate (875 mg, 5.00 mmol) in THF (10 mL) at room temperature and stirred for 2 hours. The resulting mixture was transferred to another flask that was charged with product from example 176 (610 mg, 2.5 mmol), $K_3PO_4$ (850 mg, 4.0 mmol) and Pd(dppf)$Cl_2$ (160 mg, 0.2 mmol) in THF (20 mL, together with 1 mL of water) under Argon. The resulting mixture was heated to 60° C. and stirred overnight under Argon. The reaction was cooled to room temperature. EtOAc (200 mL) was added to the reaction mixture and filtered through celite. After concentration the residue was purified with column (silica gel, EtOAc/hexane=50/50) to give the product 177 (457 mg) and 178 A (150 mg) as oil.

177: $^1$H NMR (400 MHz, $CDCl_3$) δ 7.65 (s, 1H), 7.63 (d, 1H), 7.51 (d, 1H), 7.34 (m, 5H), 5.43 (s, 1H), 5.10(s, 2H), 3.64 (m, 2H), 2.89 (t, 2H), 2.62 (s, 3H). HPLC-MS $t_R$=1.59 min ($UV_{254\ nm}$); mass calculated for formula $C_{17}H_{18}N_4O_2S$ 342.1; observed MH+ (LCMS) 343.1 (m/z).

178: HPLC-MS $t_R$=1.50 min ($UV_{254\ nm}$); mass calculated for formula $C_{17}H_{18}N_4O_2S$, 342.1; observed MH+ (LCMS) 343.1 (m/z).

Example 179

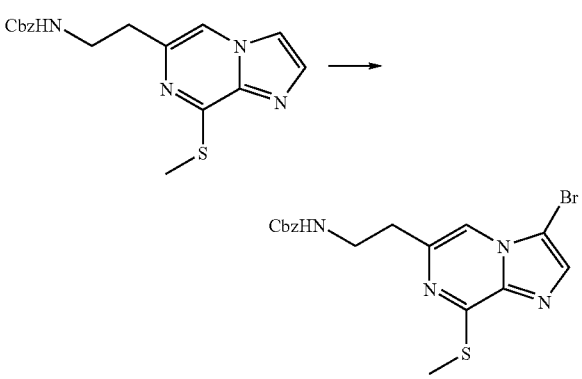

NBS (104 mg, 0.59 mmol) was added to a solution of compound 178 (200 mg, 0.59 mmol) in EtOH (10 mL), at room temperature. The mixture was stirred for 30 min and concentrated. The residue was diluted with EtOAc and washed with saturated.aq.$NaHCO_3$ (30 mL, 2×), brine and dried over $Na_2SO_4$. After concentrating, the crude product 179 was used in the next step directly without further purification. HPLC-MS $t_R$=1.88 min ($UV_{254\ nm}$); mass calculated for formula $C_{17}H_{17}BrN_4O_2S$, 420.0; observed MH+ (LCMS) 421.0 (m/z).

Example 180

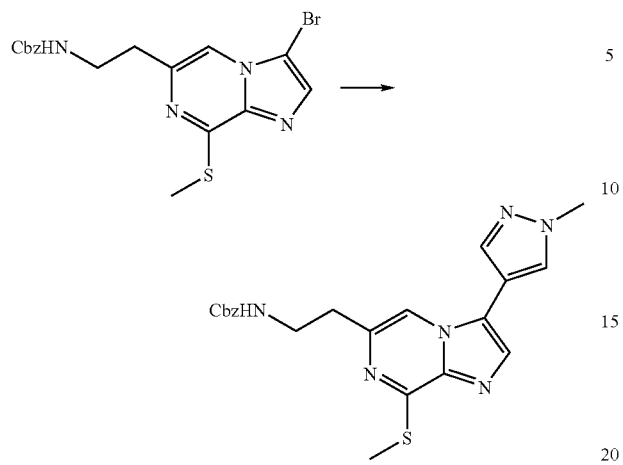

The boronate (122 mg, 0.585 mmol), was mixed with Pd(dppf)Cl$_2$ (50 mg, 0.06 mmol ), K$_3$PO$_4$(318 mg, 1.5 mmol), and the product from example 179 (246 mg, 0.585 mmol) in dioxane (5 mL) was added. The mixture was degassed thoroughly and kept under argon blanket. The resulting solution was heated at 80° C. and stirred overnight. After cooling to room temperature the mixture was diluted with EtOAc (50 mL). The solid was removed by filter through Celite and washed with EtOAc. The solvent was removed under reduced pressure and the resulting residue was purified with column chromatography (silica gel, EtOAc to MeOH/EtOAc=5/95) gave the product 180 (212 mg) as oil. HPLC-MS $t_R$=1.62 min (UV$_{254\ nm}$); mass calculated for formula C$_{21}$H$_{22}$N$_6$O$_2$S, 422.2; observed MH$^+$(LCMS) 423.3 (m/z).

Example 181

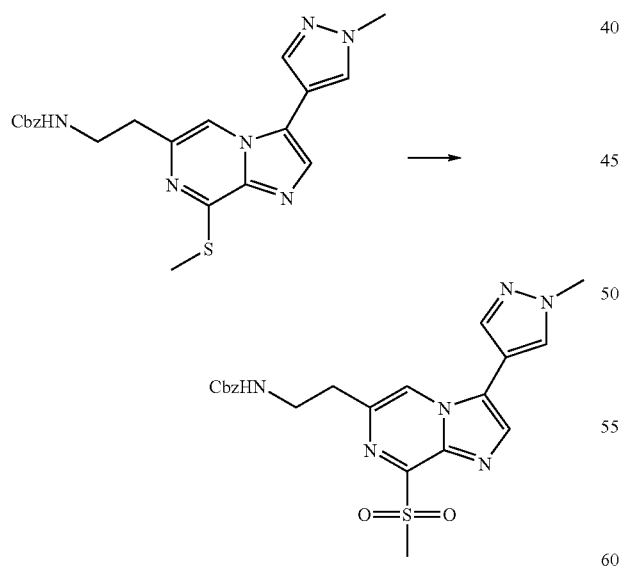

A mixture of compound 180 (212 mg, 0.5 mmol) and m-CPBA (224 mg, 77%, 1.0 mmol) in DCM (10 mL) was stirred at room temperature for 30 min then diluted with EtOAc (100 mL). The organics were washed with NaHCO$_3$ (sat. aq., 10 ml×2), brine and dried over Na$_2$SO$_4$. After concentration, the crude product 181 was used in the next step directly without further purification. HPLC-MS $t_R$=1.36 min (UV$_{254\ nm}$); mass calculated for formula C$_{21}$H$_{22}$N$_6$O$_4$S, 454.1; observed MH$^+$ (LCMS) 455.2 (m/z).

Example 182

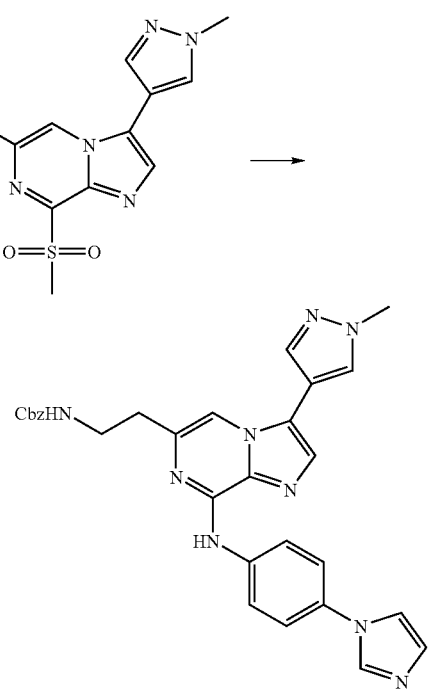

The aniline (16 mg, 0.21 mmol) was dissolved in dry DMSO (2 mL) with NaH (60% in oil, 4 mg, 0.1 mmol) under argon. The mixture was stirred for 10 min at room temperature and sulfone 181 (25 mg, 0.05 mmol) in dry DMSO (0.5 mL) was added. The reaction mixture was heated at 80° C. and stirred for 10 min. After cooling to room temperature, the mixture was purified by prep-LC to give the product 182 as a TFA salt. HPLC-MS $t_R$=1.15 min (UV$_{254\ nm}$); mass calculated for formula C$_{29}$H$_{27}$N$_9$O$_2$, 533.2; observed MH$^+$ (LCMS) 534.2 (m/z).

Example 183

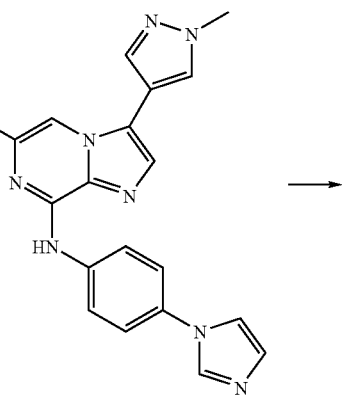

-continued

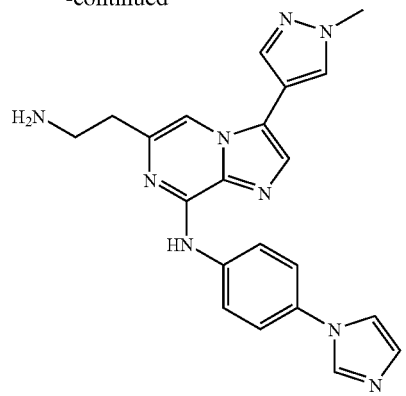

The TFA salt of compound 182 (20 mg, 0.038 mmol) was treated with 4 N HCl (2 mL) and the mixture was stirred at room temperature for 30 min. After concentration the residue was dried by lyophilization gave the final compound 183. HPLC-MS $t_R$=0.75 min (UV$_{254\ nm}$); mass calculated for formula $C_{21}H_{21}N_9$, 399.2; observed MH$^+$ (LCMS) 400.1 (m/z).

By essentially the same procedures given in examples 178-183 to give compound 184 and 185.

TABLE 16

| Example | Column 2 | MW | LCMS MH$^+$ m/z | HPLC MS $t_R$ |
|---|---|---|---|---|
| 184 | ![structure] | 354.1 | 355.1 | 0.87 |
| 185 | ![structure] | 354.1 | 355.1 | 0.90 |

Example 186

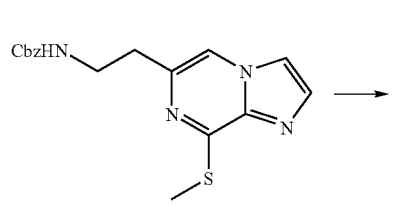

-continued

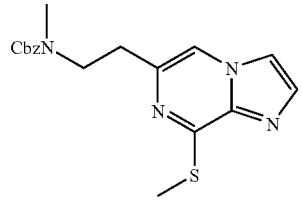

To a solution of NaH (24 mg, 60% in oil, 0.6 mmol), compound 178 (200 mg, 0.585 mmol) in dry DMF (5 mL) was added carefully. The mixture was stirred at room temperature for 10 min. Iodomethane (100 uL) was added to the above reaction mixture. The resulting mixture was stirred overnight, cooled to 0° C. and water was added carefully to quench the reaction. The aqueous was extracted with EtOAc and the organics was dried over Na$_2$SO$_4$. After concentration, the crude product was purified with column chromatography (silica gel, hexane/EtOAc=70/30) to give the product 186 (201 mg). HPLC-MS $t_R$=1.65 min (UV$_{254\ nm}$), mass calculated for formula $C_{18}H_{20}N_4O_2S$, 356.1; observed MH$^+$ (LCMS) 357.2 (m/z).

Example 187

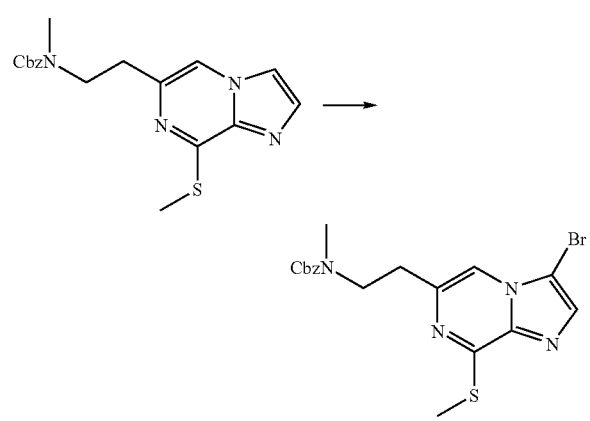

Compound 187 was prepared using the brominating conditions described in example 179. HPLC-MS $t_R$=2.01 min (UV$_{254\ nm}$); mass calculated for formula $C_{18}H_{19}BrN_4O_2S$, 434.0; observed MH$^+$ (LCMS) 435.1 (m/z).

Example 188

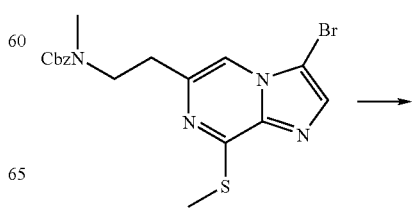

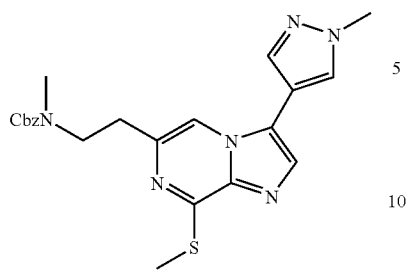

Compound 188 was synthesized using the same coupling condition described in example 180. HPLC-MS $t_R$=1.73 min (UV$_{254\ nm}$); mass calculated for formula $C_{22}H_{24}N_6O_2S$, 436.2; observed MH$^+$ (LCMS) 437.2 (m/z).

Example 189

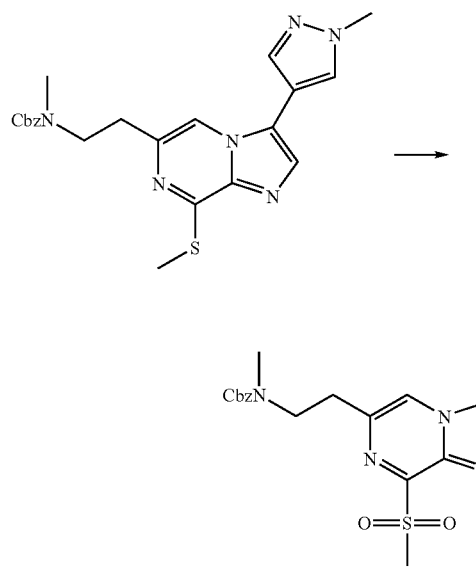

Compound 189 was prepared using the oxidation conditions described in example 181. HPLC-MS $t_R$=1.43 min (UV$_{254\ nm}$); mass calculated for formula $C_{22}H_{24}N_6O_4S$, 468.2; observed MH$^+$ (LCMS) 469.1 (m/z).

Example 190

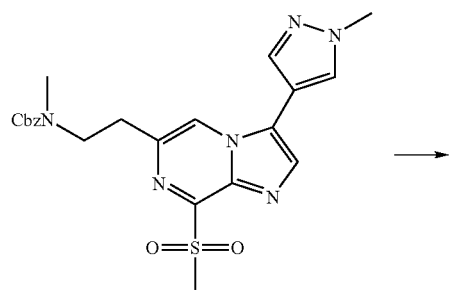

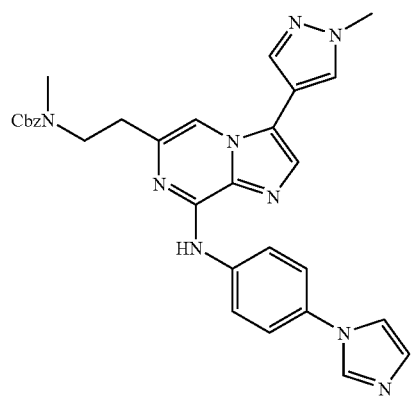

Compound 190 was prepared using the amination conditions described in example 182. HPLC-MS $t_R$=1.25 min (UV$_{254\ nm}$); mass calculated for formula $C_{30}H_{29}N_9O_2$, 547.2; observed MH$^+$ (LCMS) 548.2 (m/z).

Example 191

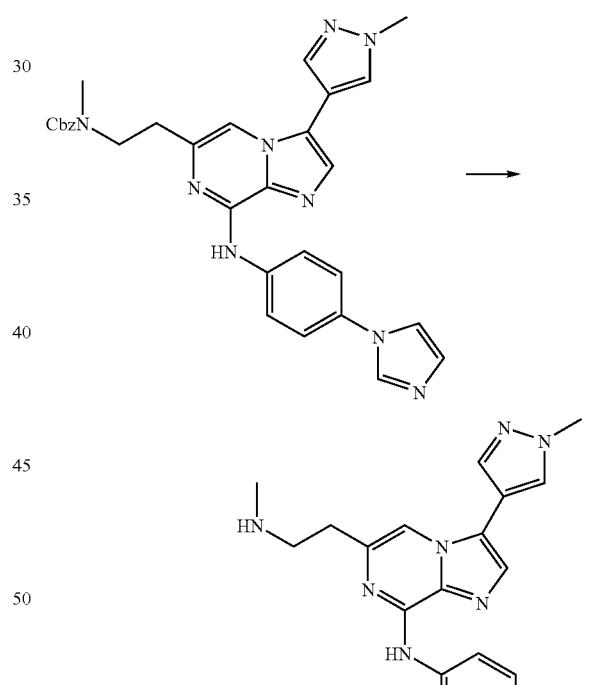

Compound 190 was synthesized using the deprotecting conditions described in example 183. HPLC-MS $t_R$=0.75 min (UV$_{254\ nm}$); mass calculated for formula $C_{22}H_{23}N_9$, 413.2; observed MH$^+$ (LCMS) 414.2 (m/z).

By essentially the same procedure given in Preparative Example 186-191, compounds given in Column 2 can be prepared from 183 and 185.

TABLE 17

| Example | Column 2 | MW | LCMS MH+ m/z | HPLC MS $t_R$ |
|---|---|---|---|---|
| 192 | | 368.2 | 355.1 | 0.87 |
| 193 | | 368.2 | 369.1 | 0.90 |
| 194 | | 413.2 | 414.2 | 0.78 |

Example 195

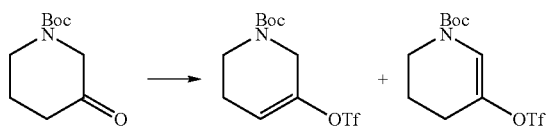

A solution of LDA (28.6 mmol) was prepared from iso-Pr$_2$NH (4.03 mL, 28.6 mmol) and n-BuLi (11.40 mL, 2.5 M in hexane, 28.6 mmol) in THF (50 mL). The solution was cooled at −78° C. and N-Boc-3-piperidone (4.0 g, 20 mmol) in THF (10 mL) was added with a syringe. After 15 min, N-phenyltriflimide (8.60 g, 24.0 mmol) in THF (20 mL) was added. The reaction mixture was then warmed up to room temperature slowly and stirred overnight. After evaporation, of the solvent under vacuum, the residue was dissolved in DCM (120 mL). The solution was then filtered on neutral alumina and evaporated. Flash chromatography (hexane/EtOAc 80/20) of the crude oil on silica gel gave products 195 and 196.

Product 195: HPLC-MS $t_R$=1.65 min (UV$_{254\ nm}$); mass calculated for formula C$_{11}$H$_{16}$F$_3$NO$_5$S, 231.1; observed MH+ (LCMS) 232.1 (m/z).

Product 196: HPLC-MS $t_R$=1.68 min (UV$_{254\ nm}$); mass calculated for formula C$_{11}$H$_{16}$F$_3$NO$_5$S, 231.1; observed MH+ (LCMS) 232.1 (m/z).

Example 197

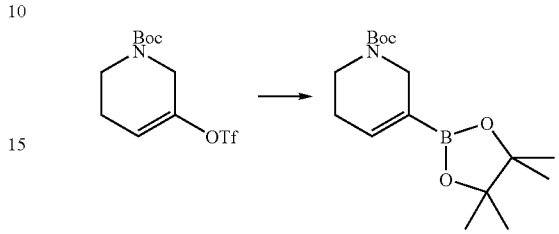

To a 25 mL round bottom flask charged with bis(pinacolato)diboron (1.50 g, 6 mmol), potassium acetate (1.5 g, 15 mmol), Pd(dppf)Cl$_2$ (408 mg, 0.5 mmol) and DPPF (277 mg, 0.5 mmol). Compound 195 (1.55 g, 5.0 mmol) in dioxane 20 mL) was added to the above mixture. The mixture was degassed thoroughly and placed under argon. This resulting mixture was then heated at 80° C. for overnight, diluted with EtOAc (40 mL) and filtered through celite. After concentration, the residue was purified with column chromatography (silica gel, Hexane/EtOAc=60/40) to give the product (832 mg) as an oil. HPLC-MS $t_R$=2.41 min (UV$_{254\ nm}$), mass calculated for formula C$_{16}$H$_{28}$BNO$_4$, 309.2; observed MH+;-t-Bu (LCMS) 254.2(m/z).

Example 198

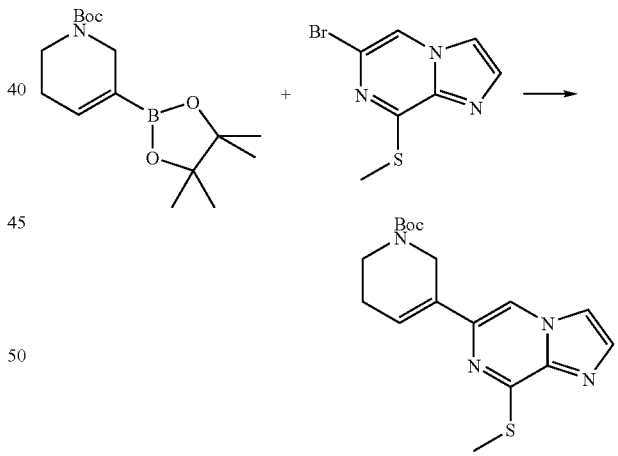

To a 25 mL round bottom flask charged with boronate 197 (456 mg, 1.5 mmol), K$_2$CO$_3$ (800 mg, 6 mmol), and Pd(dppf)Cl$_2$ (160 mg, 0.2 mmol) was added a solution of product from example 177(360 mg, 1.5 mmol) in DMF (10 mL). The mixture was degassed thoroughly and placed under argon. This resulting mixture was then heated at 80° C. overnight. The reaction mixture was diluted with EtOAc (40 mL) and filtered through Celite. After concentration, the residue was purified by column chromatography (silica gel, Hexane/EtOAc=60/40) to give the product 198 (258 mg) as an oil. HPLC-MS $t_R$=1.91 min (UV$_{254\ nm}$); mass calculated for formula C$_{17}$H$_{22}$N$_4$O$_2$S, 346.1; observed MH+ (LCMS) 347.2 (m/z).

Example 199

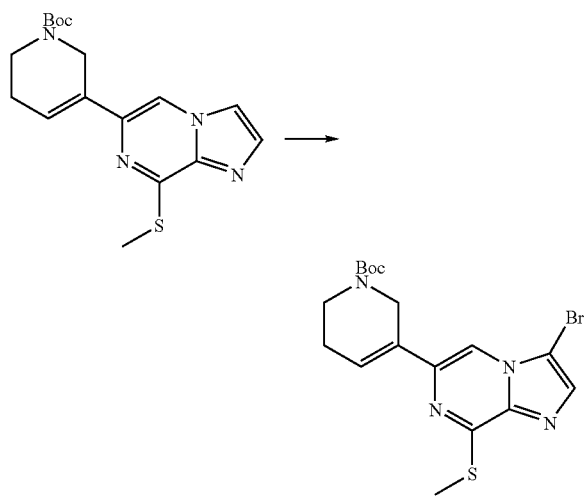

Compound 199 was prepared using brominating conditions described in example 179. HPLC-MS $t_R$=2.26 min (UV$_{254\ nm}$); mass calculated for formula $C_{17}H_{21}BrN_4O_2S$, 424.1; observed MH$^+$ (LCMS) 425.0 (m/z).

Example 200

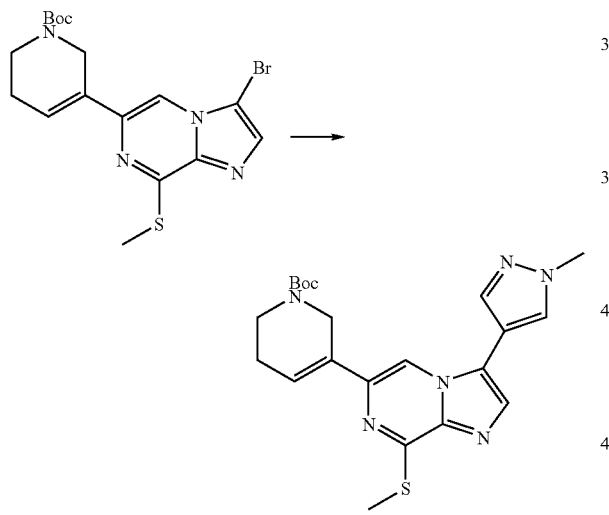

By essentially, example product 200 was synthesized using the same coupling conditions described in example 180. HPLC-MS $t_R$=1.96 min (UV$_{254\ nm}$); mass calculated for formula $C_{21}H_{26}N_6O_2S$, 426.2; observed MH$^+$ (LCMS) 427.1 (m/z).

Example 201

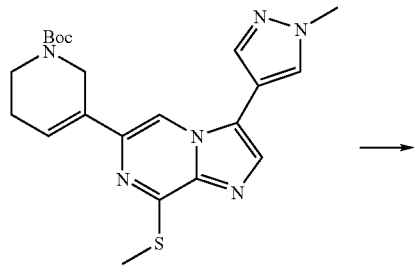

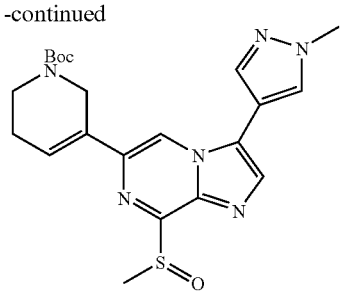

The mixture of compound 200 (130 mg, 0.305 mmol) and m-CPBA (68 mg, 77%, 0.305 mmol) in DCM (5 mL) was stirred at 0° C. for 30 min and then diluted with EtOAc (100 mL). The organics were washed with saturated aqueous NaHCO$_3$ (10 mL, 2×), brine, and dried over Na$_2$SO$_4$. After concentration the crude product 201 was used in the next step directly without further purification. HPLC-MS $t_R$=1.48 min (UV$_{254\ nm}$); mass calculated for formula C$_2$, H$_{26}$N$_6$O$_3$S, 442.2; observed MH$^+$ (LCMS) 443.2 (m/z).

Example 202

The product example 202 was prepared using the similar experimental conditions described in product example 182. HPLC-MS $t_R$=1.44 min (UV$_{254\ nm}$); mass calculated for formula $C_{29}H_{31}N_9O_2$, 537.3; observed MH$^+$ (LCMS) 538.3 m/z).

Example 203

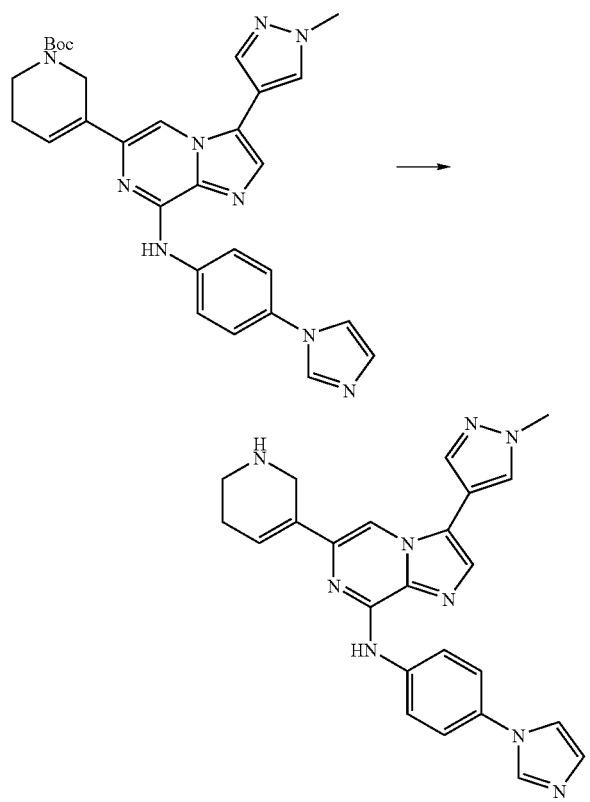

The product form example 202 (20 mg) was treated with 4 N HCl in dioxane (4 mL) and stirred at room temperature for 10 min. After concentration, the residue was dried by lyophilization gave compound 203. HPLC-MS $t_R$=0.75 min (UV$_{254\ nm}$); mass calculated for formula $C_{24}H_{23}N_9$, 437.2; observed MH⁺ (LCMS) 438.3 (m/z). 10 By essentially the same procedures given in Preparative Example 203, compounds given in Column 2 of Table 18 can be prepared from example 195 through 203.

TABLE 18

| Example | Column 2 | MW | LCMS MH⁺ m/z | HPLC MS $t_R$ |
|---|---|---|---|---|
| 204 | | 437.2 | 438.3 | 0.74 |
| 205 | | 392.2 | 393.1 | 0.97 |
| 206 | | 392.2 | 393.2 | 0.95 |

Example 207

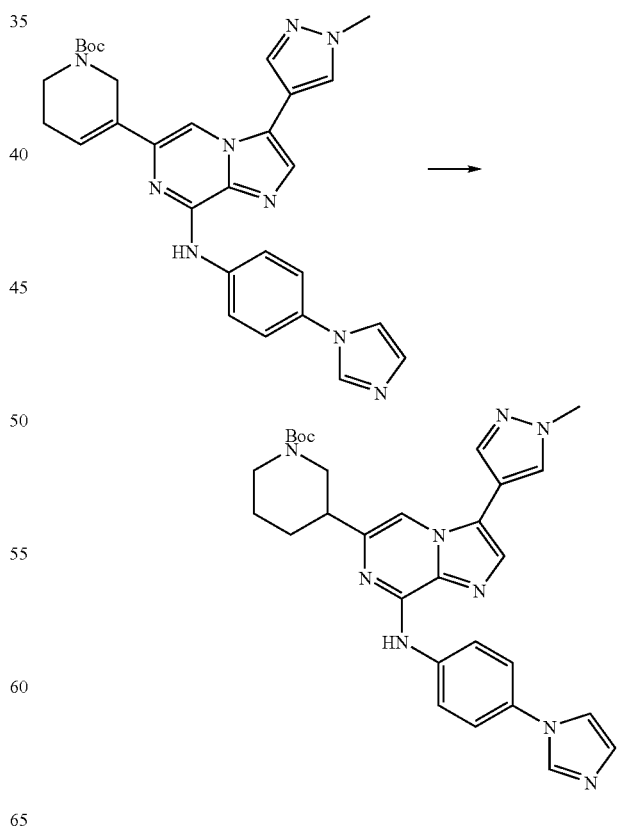

The product from example 202 (20 mg, TFA salt) was dissolved in THF (5 mL), and DIEA (500 uL) was added. To this mixture, 10% Pd/C (5 mg) was added and the resulting mixture was hydrogenated under H₂ atm. while stirring for overnight. After filtration and concentration the residue was purified by prep-LC to give the product 207. HPLC-MS $t_R$=1.45 min (UV$_{254\ nm}$); mass calculated for formula $C_{29}H_{33}N_9O_2$, 539.3; observed MH⁺ (LCMS) m/z 540.3 (m/z).

Example 208

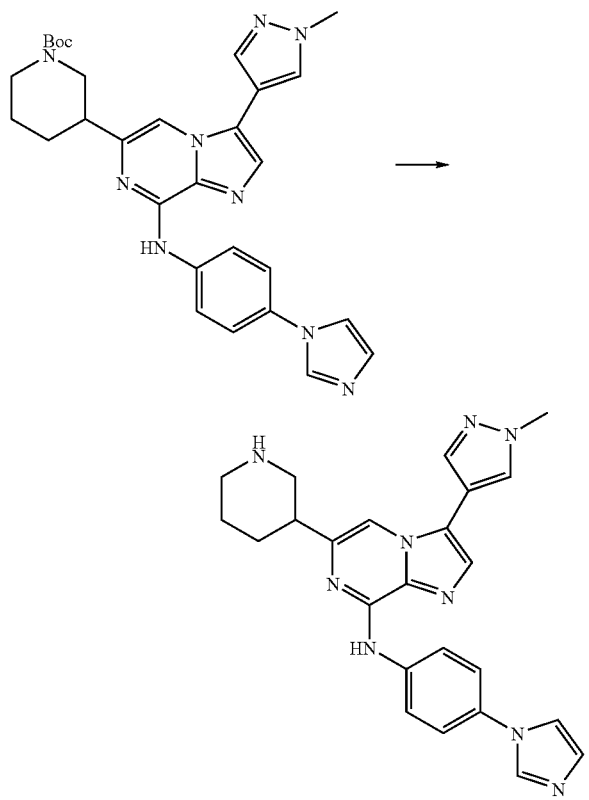

Product from example 207 was treated with was treated with 4 N HCl in dioxane (4 mL) and stirred at room temperature for 10 min. After concentration, the residue was dried with lyophilization to give 208. HPLC-MS $t_R$=0.80 min (UV$_{254\ nm}$); mass calculated for formula $C_{24}H_{25}N_9$, 439.2; observed MH⁺ (LCMS) 440.2 (m/z).

By essentially the same procedure given in Preparative Example 208, compounds given in Column 2 of Table 19 can be prepared.

TABLE 19

| Example | Column 2 | MW | LCMS MH⁺ m/z | HPLC MS $t_R$ |
|---|---|---|---|---|
| 209 | | 394.2 | 395.2 | 0.95 |

Example 210

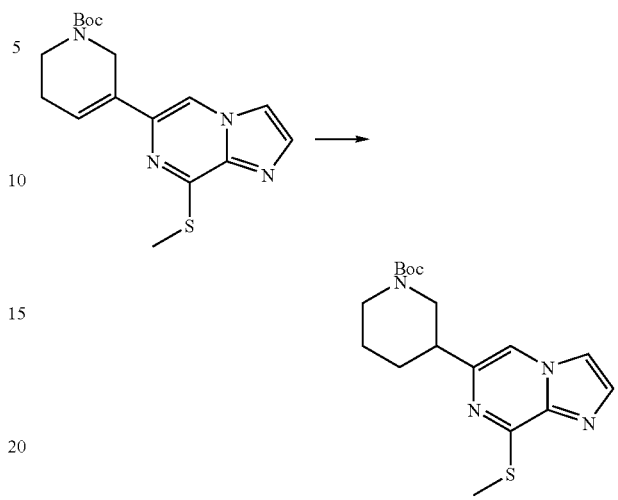

The product from example 198 (175 mg, 0.50 mmol) was dissolved in 20 mL of DME and 4 mL of water. To the mixture was added p-toluenesulfonyl hydrazide (1.86 g, 10 mmol). The mixture was heated up to 90° C. following the addition of NaOAc (1.64 g, 20.0 mmol) to the reaction. After stirring at reflux for 4 hours, additional p-toluenesulfonyl hydrazide (1.86 g, 10.0 mmol) and NaOAc (1.64 g, 20 mmol) were added. The mixture was at reflux overnight. After cooling to room temperature, the mixture was diluted with EtOAc (200 mL) and washed with H₂O, and brine. The organics were dried over Na₂SO₄ and concentrated. The resulting residue was purified by prep-LC to give the product 210. HPLC-MS $t_R$=1.92 min (UV$_{254\ nm}$); mass calculated for formula $C_{17}H_{24}N_4O_2S$, 348.2; observed MH⁺ (LCMS) 349.2 (m/z).

Example 211

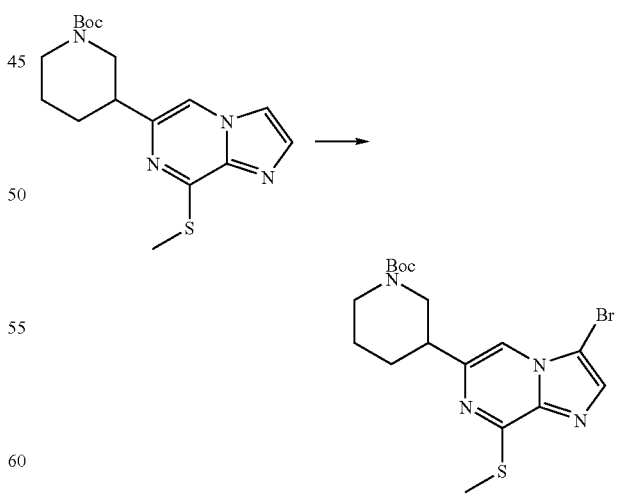

Product from example 211 was prepared using brominating conditions described in example 179. HPLC-MS $t_R$=5.89 min (UV$_{254\ nm}$); mass calculated formula $C_{17}H_{23}BrN_4O_2S$, 426.1; observed MH⁺ (LCMS) 427.0 (m/z).

Example 212

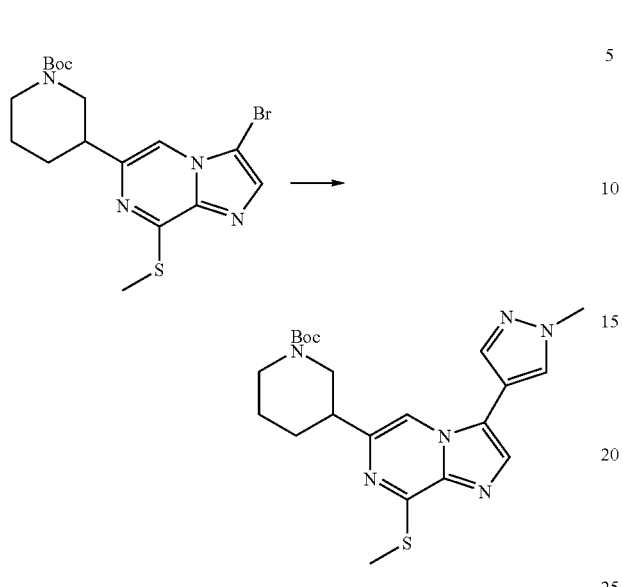

Compound 212 was synthesized using coupling conditions described in example 180. HPLC-MS $t_R$=1.99 min (UV$_{254\ nm}$); mass calculated for formula $C_{21}H_{28}N_6O_2S$, 428.2; observed MH$^+$ (LCMS) 429.2 (m/z).

Example 213

Compound 213 was synthesized using oxidation conditions described in example 181. HPLC-MS $t_R$=1.64 min (UV$_{254\ nm}$); mass calculated for formula $C_{21}H_{28}N_6O_4S$; 460.2, observed MH$^+$ (LCMS) 461.2 (m/z).

Example 214

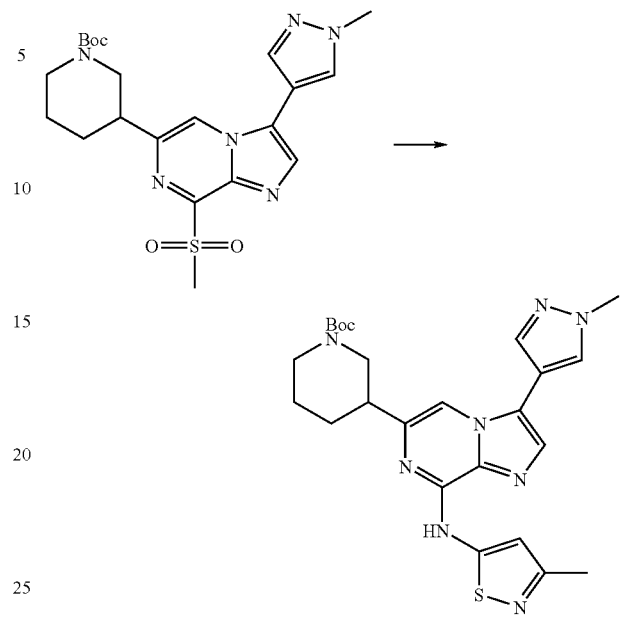

Compound 214 was prepared using the experimental condition described in example 182. HPLC-MS $t_R$=1.84 min (UV$_{254\ nm}$); mass calculated for formula $C_{24}H_{30}N_8O_2S$; 494.2, observed MH$^+$ (LCMS) 495.2 (m/z).

Example 215

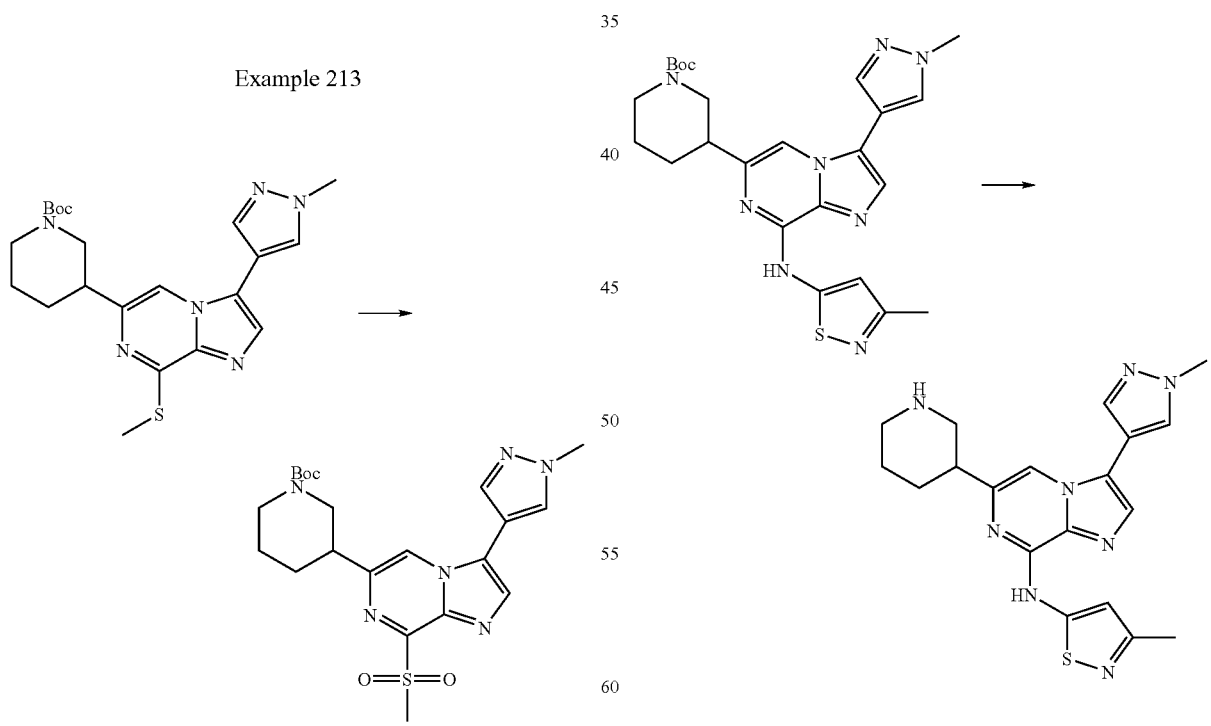

The compound 214 (20 mg) was treated with HCl (4 N in dioxane, 4 mL) and stirred at room temperature for 10 min. After concentrating, the residue was dried by lyophilization to give compound 215. HPLC-MS $t_R$=0.98 min (UV$_{254\ nm}$); mass calculated for formula $C_{19}H_{22}N_8S$, 394.2; observed MH$^+$ (LCMS) 395.2 (m/z).

Example 216

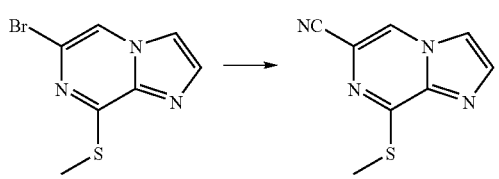

To a 25 mL round bottom flask charged with product from example 177 (486 mg, 2.0 mmol), $Pd_2(dba)_3$ (180 mg, 0.2 mmol), dppf (235 mg, 0.4 mmol), nd $Zn(CN)_2$ (500 mg, 4.2 mmol) was added DME (10 ml) as solvent. The mixture was degassed thoroughly and placed under argon. This resulting mixture was then heated at 80° C. overnight. The reaction was diluted with EtOAc (100 mL) and filtered through Celite. After concentrating, the residue was purified with column chromatography (silica gel, Hexane/EtOAc=60/40) to give the product 216 (399 mg) as yellowish solid. $^1$H NMR (400 MHz, $CDCl_3$) δ 8.31 (s, 1H), 7.80 (d, 1H), 7.69 (d, 1H), 2.66 (s, 3H). HPLC-MS $t_R$=1.15 min ($UV_{254\ nm}$); mass calculated for formula $C_8H_6N_4S$; 190.0, observed $MH^+$ (LCMS) 191.1 (m/z).

Example 217

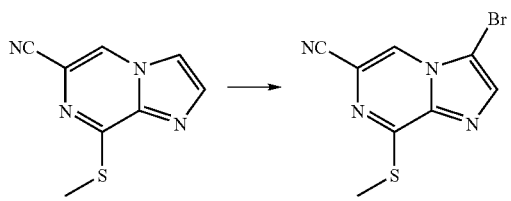

Product of the example 217 was prepared using brominating conditions described in example 179. HPLC-MS $t_R$=1.53 min ($UV_{254\ nm}$); mass calculated for formula $C_8H_5BrN_4S$, 267.9; observed $MH^+$ (LCMS) 269.0 (m/z).

Example 218

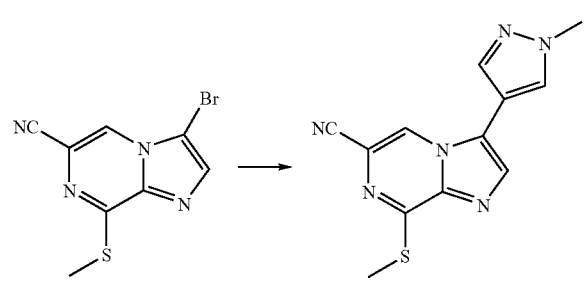

Compound 218 was synthesized using coupling condition described in example 180. HPLC-MS $t_R$=1.36 min ($UV_{254\ nm}$); mass calculated for formula $C_{12}H_{10}N_6S$, 270.1; observed $MH^+$ (LCMS) 271.0 (m/z).

Example 219, 220

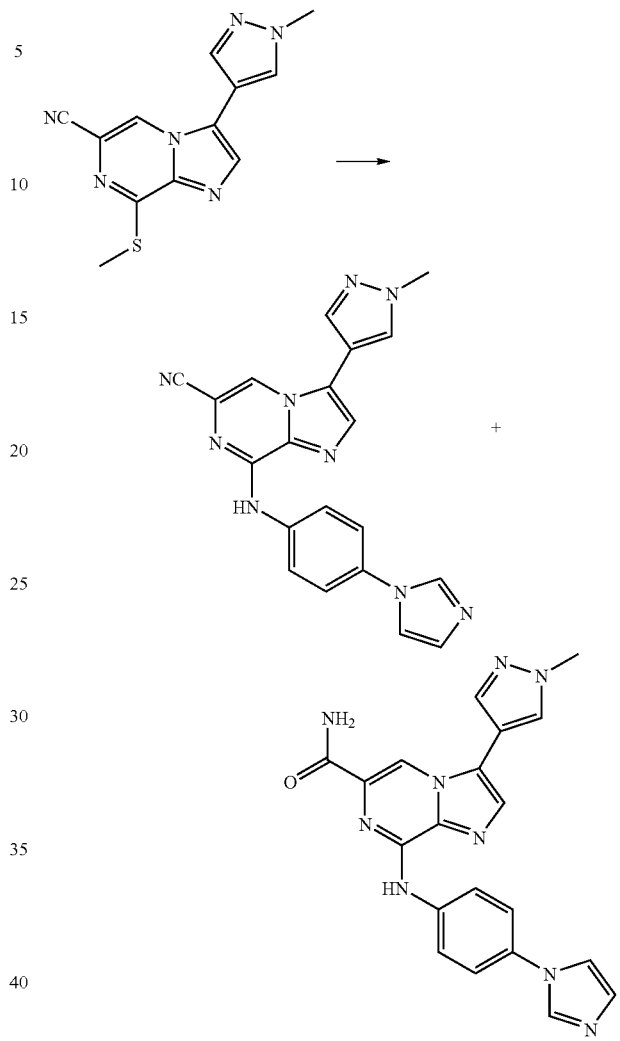

The aniline (32 mg, 0.42 mmol) was dissolved in dry DMSO (2 mL) and NaH (60% in oil, 8 mg, 0.2 mmol) was added under argon. The mixture was stirred for 10 min at room temperature then, sulfide 219 (27 mg, 0.1 mmol) in dry DMSO (0.5 mL) was added. The resulting mixture was heated up to 80° C. and stirred for 10 min. After cooling and LCMS analysis shown the formation of two products. The mixture was purified with Prep-LC to give the product 219 and 220 as TFA salt.

219: HPLC-MS $t_R$=0.77 min ($UV_{254\ nm}$); mass calculated for formula $C_{20}H_{15}N_9$, 381.1; observed $MH^+$ (LCMS) 382.1 (m/z).

220: HPLC-MS $t_R$=0.63 min ($UV_{254\ nm}$); mass calculated for formula $C_{20}H_{17}N_9O$ 399.2; observed $MH^+$ (LCMS) 400.1 (m/z).

Assay:

BACULOVIRUS CONSTRUCTIONS: Cyclins A and E were cloned into pFASTBAC (Invitrogen) by PCR, with the addition of a GluTAG sequence (EYMPME) at the amino-terminal end to allow purification on anti-GluTAG affinity columns. The expressed proteins were approximately 46 kDa (cyclin E) and 50 kDa (cyclin A) in size. CDK2 was also cloned into PFASTBAC by PCR, with the addition of a haemaglutinin epitope tag at the carboxy-terminal end (YD-VPDYAS). The expressed protein was approximately 34 kDa in size.

ENZYME PRODUCTION: Recombinant baculoviruses expressing cyclins A, E and CDK2 were infected into SF9 cells at a multiplicity of infection (MOI) of 5, for 48 hrs. Cells were harvested by centrifugation at 1000 RPM for 10 minutes. Cyclin-containing (E or A) pellets were combined with CDK2 containing cell pellets and lysed on ice for 30 minutes in five times the pellet volume of lysis buffer containing 50 mM Tris pH 8.0, 0.5% NP40, 1 mM DTT and protease/phosphatase inhibitors (Roche Diagnostics GmbH, Mannheim, Germany). Mixtures were stirred for 30-60 minutes to promote cyclin-CDK2 complex formation. Mixed lysates were then spun down at 15000 RPM for 10 minutes and the supernatant retained. 5 ml of anti-GluTAG beads (for one liter of SF9 cells) were then used to capture cyclin-CDK2 complexes. Bound beads were washed three times in lysis buffer. Proteins were competitively eluted with lysis buffer containing 100-200 ug/mL of the GluTAG peptide. Eluate was dialyzed overnight in 2 liters of kinase buffer containing 50 mM Tris pH 8.0, 1 mM DTT, 10 mM MgCl2, 100 uM sodium orthovanadate and 20% glycerol. Enzyme was stored in aliquots at −70° C.

IN VITRO KINASE ASSAY: CDK2 kinase assays (either cyclin A or E-dependent) were performed in low protein binding 96-well plates (Corning Inc, Corning, N.Y.). Enzyme was diluted to a final concentration of 50 ug/ml in kinase buffer containing 50 mM Tris pH 8.0, 10 mM $MgCl_2$, mM DTT, and 0.1 mM sodium orthovanadate. The substrate used in these reactions was a biotinylated peptide derived from Histone H1 (from Amersham, UK). The substrate was thawed on ice and diluted to 2 uM in kinase buffer. Compounds were diluted in 10% DMSO to desirable concentrations. For each kinase reaction, 20 μl of the 50 ug/ml enzyme solution (1 μg of enzyme) and 20 μl of the 1 μM substrate solution were mixed, then combined with 10 μl of diluted compound in each well for testing. The kinase reaction was started by addition of 50 μl of 4 μM ATP and 1 μCi of 33P-ATP (from Amersham, UK). The reaction was allowed to run for 1 hour at room temperature. The reaction was stopped by adding 200 μl of stop buffer containing 0.1% Triton X-100, 1 mM ATP, 5 mM EDTA, and 5 mg/ml streptavidine coated SPA beads (from Amersham, UK) for 15 minutes. The SPA beads were then captured onto a 96-well GF/B filter plate (Packard/Perkin Elmer Life Sciences) using a Filtermate universal harvester (Packard/Perkin Elmer Life Sciences.). Non-specific signals were eliminated by washing the beads twice with 2M NaCl then twice with 2 M NaCl with 1% phosphoric acid. The radioactive signal was then measured using a TopCount 96 well liquid scintillation counter (from Packard/Perkin Elmer Life Sciences).

$IC_{50}$ DETERMINATION: Dose-response curves were plotted from inhibition data generated, each in duplicate, from 8 point serial dilutions of inhibitory compounds. Concentration of compound was plotted against % kinase activity, calculated by CPM of treated samples divided by CPM of untreated samples. To generate $IC_{50}$ values, the dose-response curves were then fitted to a standard sigmoidal curve and $IC_{50}$ values were derived by nonlinear regression analysis. The thus-obtained $IC_{50}$ values for the compounds of the invention are shown in Table 7. These kinase activities were generated by using cyclin A or cyclin E using the above-described assay.

TABLE 7

| CMPD | $IC_{50}$ (μM) | % INH @ 0.05 ug/mL | % INH @ 0.5 ug/mL |
|---|---|---|---|
| (structure) | 15 | | |
| (structure) | 22.5 | | |
| (structure) | 4.18 | | |
| (structure) | 0.53 | | |

TABLE 7-continued

| CMPD | IC$_{50}$ (μM) | % INH @ 0.05 ug/mL | % INH @ 0.5 ug/mL |
|---|---|---|---|
| [6-(2-chlorophenyl)-3-bromo-imidazo[1,2-a]pyrazin-8-yl]-(pyridin-4-ylmethyl)amine | 0.49 | | |
| [6-(2-chlorophenyl)-3-bromo-imidazo[1,2-a]pyrazin-8-yl]-(pyridin-3-ylmethyl)amine | 0.24 | 47.4 | 88.6 |
| [6-(2-chlorophenyl)-3-iodo-imidazo[1,2-a]pyrazin-8-yl]-(pyridin-3-ylmethyl)amine | 0.23 | | |
| [6-(2-chlorophenyl)-3-chloro-imidazo[1,2-a]pyrazin-8-yl]-(pyridin-3-ylmethyl)amine | 0.43 | | |
| [6,3-diphenyl-imidazo[1,2-a]pyrazin-8-yl]-(pyridin-3-ylmethyl)amine | 6.7 | | |
| [6-phenyl-3-bromo-imidazo[1,2-a]pyrazin-8-yl]-(6-trifluoromethylpyridin-3-ylmethyl)amine | 4.551 | | |
| [6-phenyl-3-acetyl-imidazo[1,2-a]pyrazin-8-yl]-(pyridin-3-ylmethyl)amine | 4.7 | | |
| [6-(2-chlorophenyl)-3-bromo-imidazo[1,2-a]pyrazin-8-yl]-(1-hydroxymethyl-ethyl)amine | 0.2 | 63.0 | 92.7 |

TABLE 7-continued

| CMPD | IC$_{50}$ (μM) | % INH @ 0.05 ug/mL | % INH @ 0.5 ug/mL |
|---|---|---|---|
| 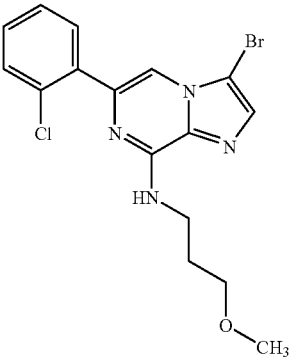 | | 30.7 | 71.5 |
| 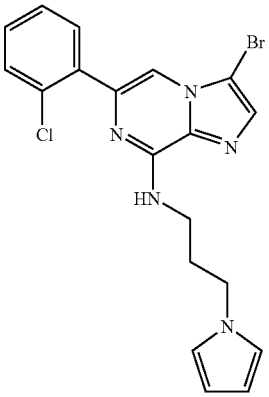 | | 42.2 | 48.8 |
| 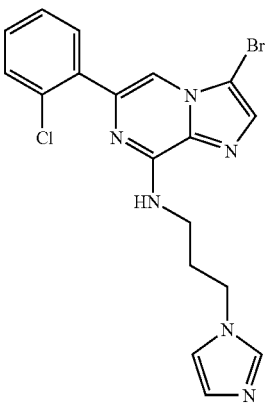 | | 37.5 | 29.4 |

TABLE 7-continued

| CMPD | IC$_{50}$ (μM) | % INH @ 0.05 ug/mL | % INH @ 0.5 ug/mL |
|---|---|---|---|
| 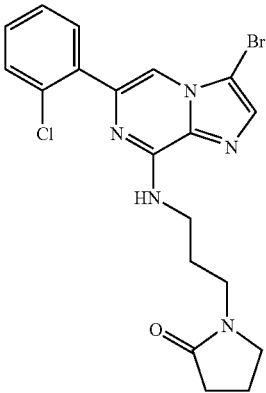 | | 30.7 | 67.8 |

As demonstrated above by the assay values, the compounds of the present invention exhibit excellent CDK inhibitory properties.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula:

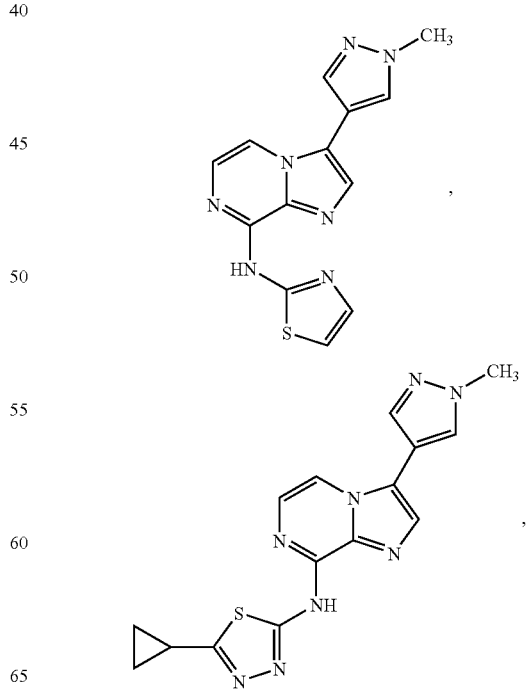

-continued
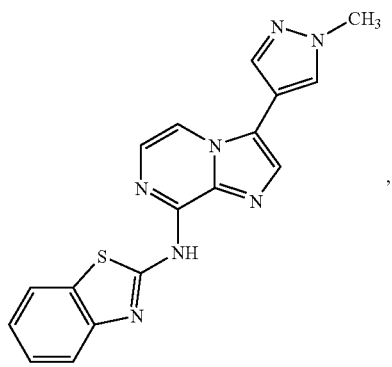
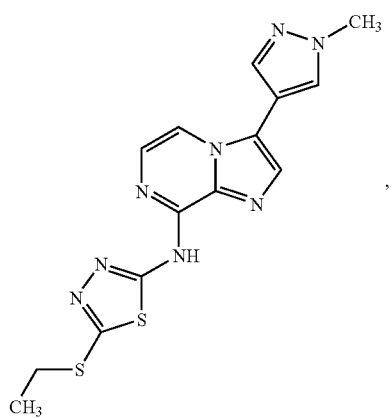
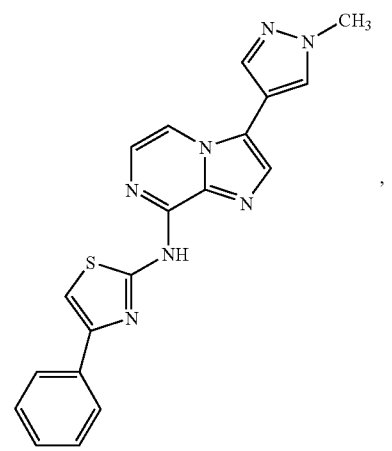
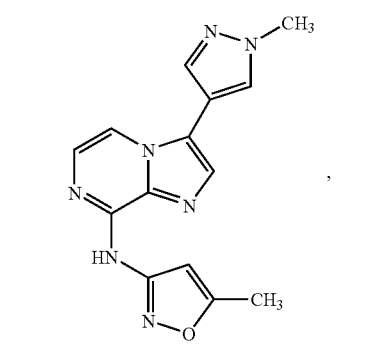
-continued
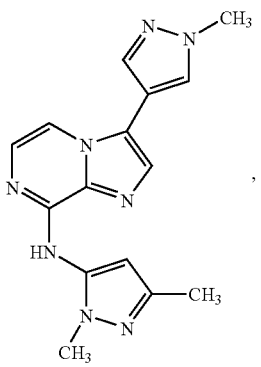
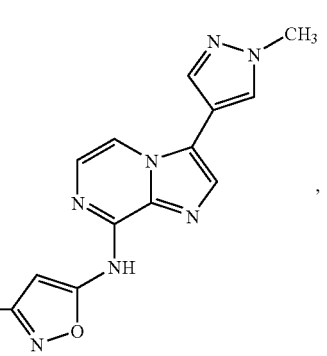
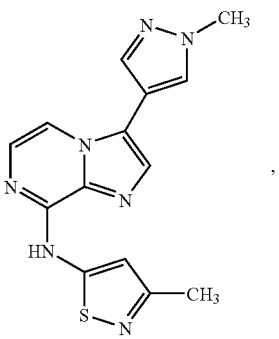
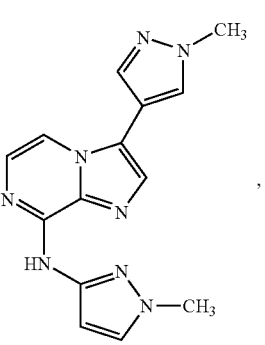

259 260
-continued
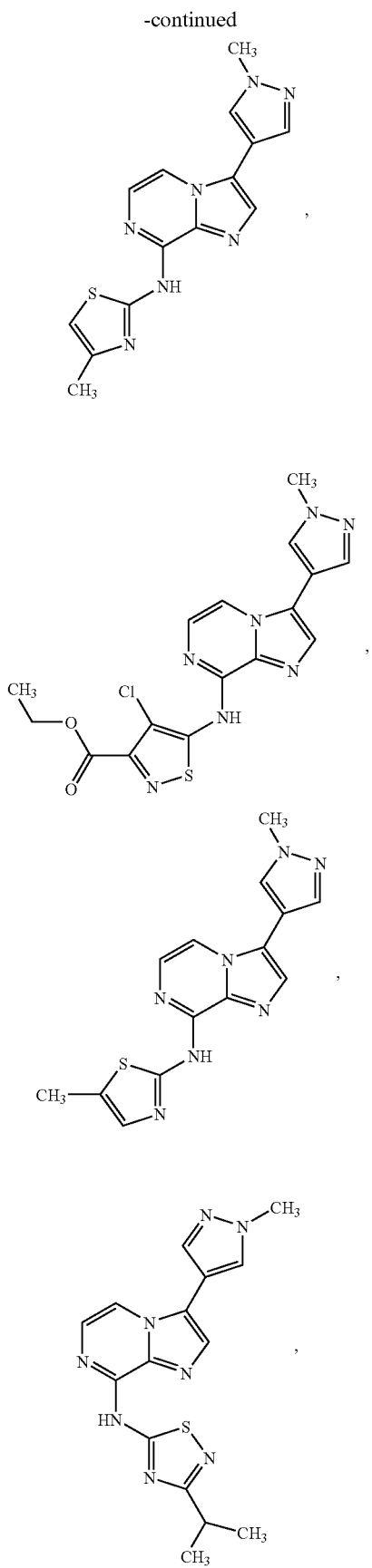
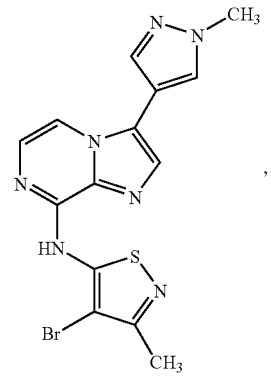
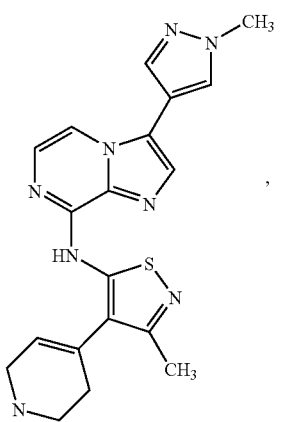
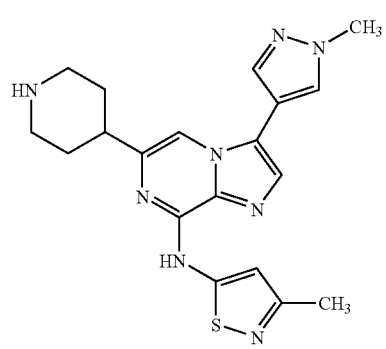

-continued
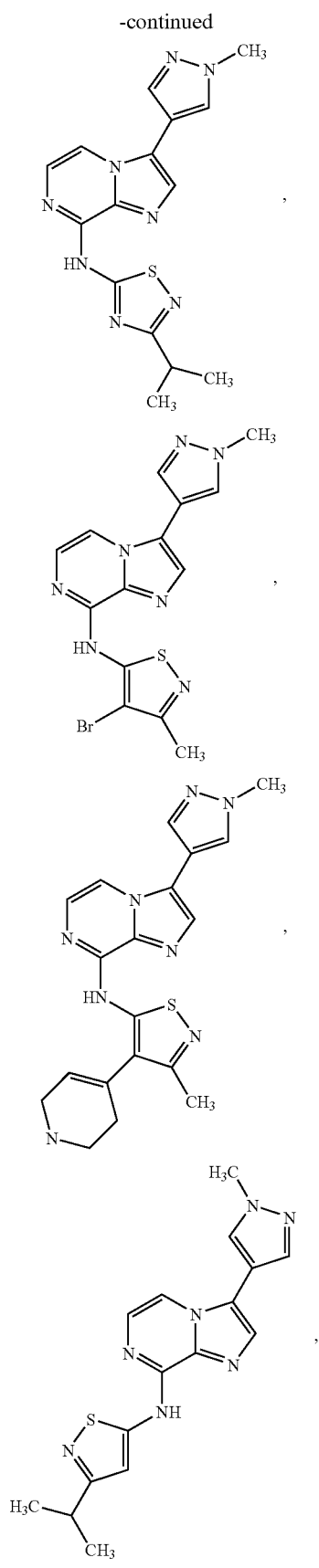
-continued
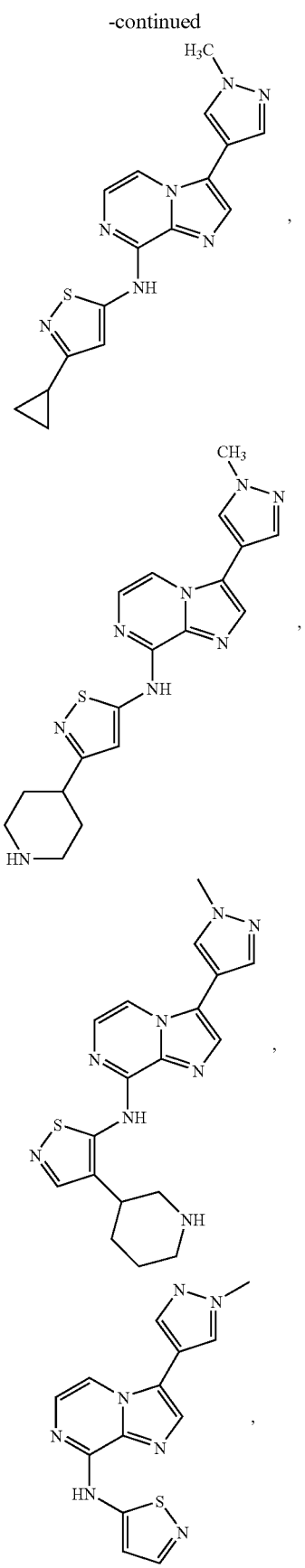

-continued

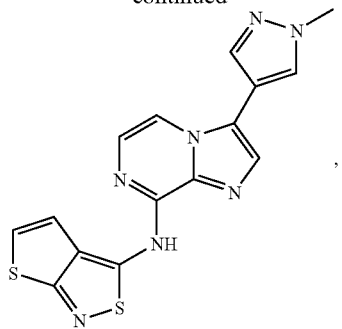

,

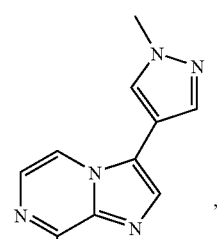

,

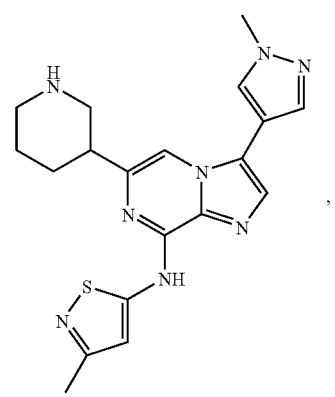

,

-continued

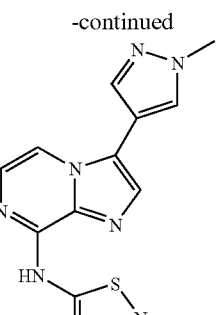

or

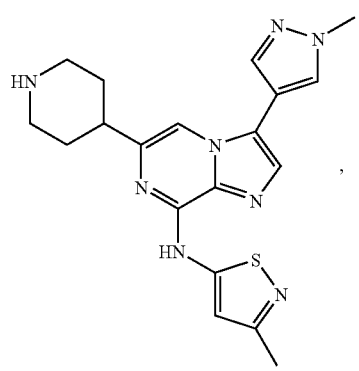

, or a pharmaceutically acceptable salt thereof.

2. A pharmaceutical composition comprising a therapeutically effective amount of at least one compound of claim 1, or a pharmaceutically acceptable salt thereof, in combination with at least one pharmaceutically acceptable carrier.

3. A compound of the formula:

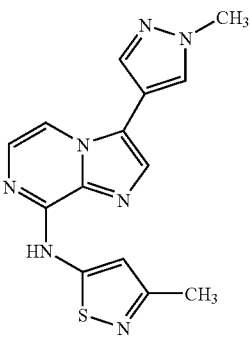

or a pharmaceutically acceptable salt thereof.

4. A compound of the formula:

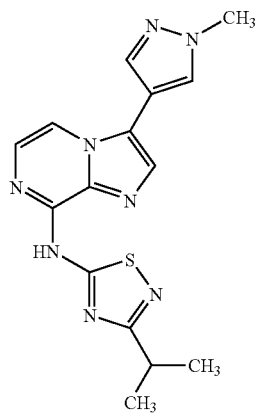

or a pharmaceutically acceptable salt thereof.

5. A compound of the formula:

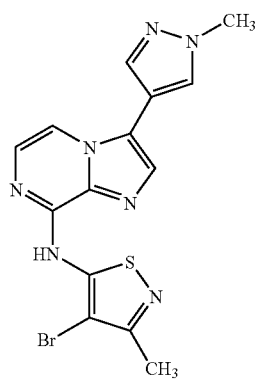

or a pharmaceutically acceptable salt thereof.

6. A compound of the formula:

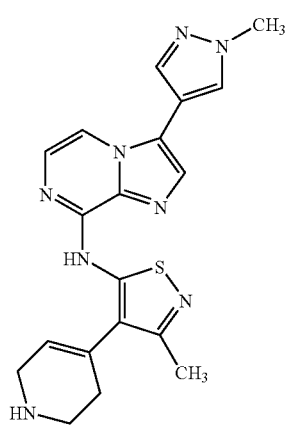

or a pharmaceutically acceptable salt thereof.

7. A compound of the formula:

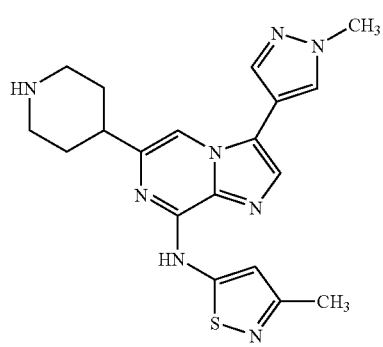

or a pharmaceutically acceptable salt thereof.

8. A compound of the formula:

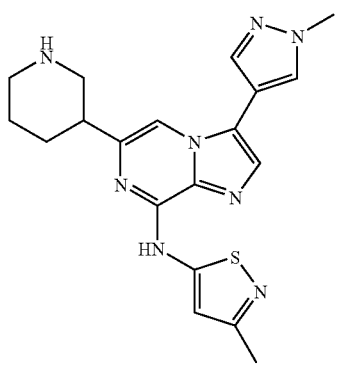

or a pharmaceutically acceptable salt thereof.

9. A compound of the formula:

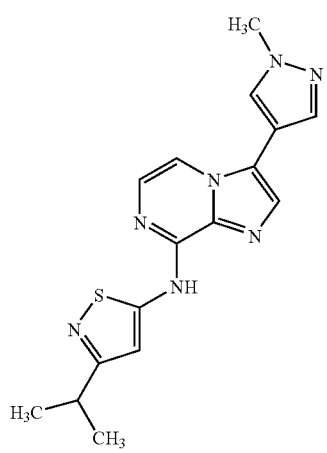

or a pharmaceutically acceptable salt thereof.

10. A compound of the formula:

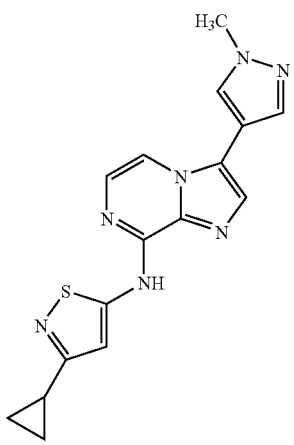

or a pharmaceutically acceptable salt thereof.

11. A compound of the formula:

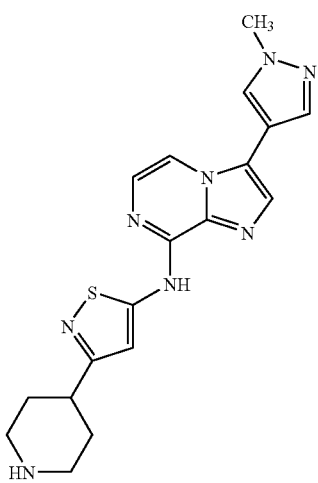

or a pharmaceutically acceptable salt thereof.

12. A compound of the formula:

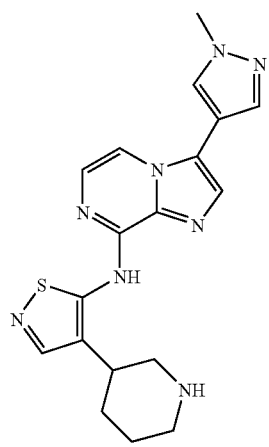

or a pharmaceutically acceptable salt thereof.

13. A compound of the formula:

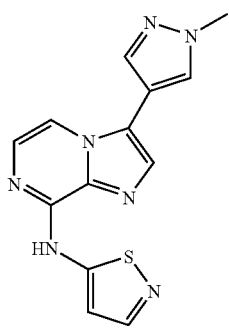

or a pharmaceutically acceptable salt thereof.

14. A compound of the formula:

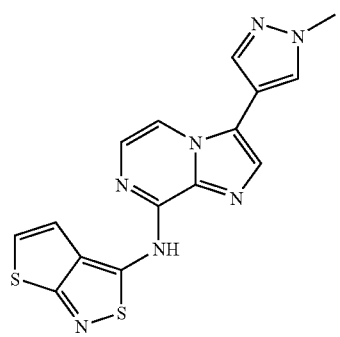

or a pharmaceutically acceptable salt thereof.

15. A compound of the formula:

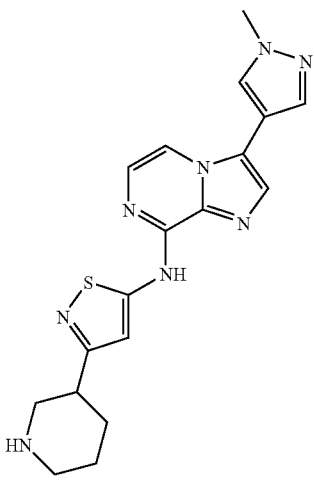

or a pharmaceutically acceptable salt thereof.

* * * * *